(12) United States Patent
Li et al.

(10) Patent No.: US 6,703,198 B1
(45) Date of Patent: Mar. 9, 2004

(54) METHODS OF DIAGNOSING ALAGILLE SYNDROME

(75) Inventors: Linheng Li, Seattle, WA (US); Leroy Hood, Seattle, WA (US); Ian D. Krantz, Philadelphia, PA (US); Nancy B. Spinner, Bala Cynwyd, PA (US)

(73) Assignees: The University of Washington, Seattle, WA (US); The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 09/566,047

(22) Filed: May 5, 2000

Related U.S. Application Data

(62) Division of application No. 08/882,046, filed on Jun. 25, 1997, now Pat. No. 6,136,952.

(51) Int. Cl.[7] .......................... C12Q 1/68; C07K 17/00; C07K 14/00; C07H 21/04

(52) U.S. Cl. ........................... 435/6; 435/7.1; 530/350; 530/300; 536/23.1; 536/23.5

(58) Field of Search ...................... 435/6, 7.1; 530/350, 530/300; 536/23.1, 23.5

(56) References Cited

U.S. PATENT DOCUMENTS

| | | |
|---|---|---|
| 5,869,282 A | 2/1999 | Ish-Horowicz et al. |
| 6,022,687 A * | 2/2000 | Letarte et al. |

FOREIGN PATENT DOCUMENTS

| | | |
|---|---|---|
| EP | 0861894 | 9/1998 |
| WO | WO 96/27610 | 9/1996 |
| WO | WO 97/11716 | 3/1997 |
| WO | WO 97/19172 | 5/1997 |
| WO | WO 97/45143 | 12/1997 |

OTHER PUBLICATIONS

Baker et al., "Spacing Differentiation in the Developing *Drosophila* Eye: A Fibrinogen–Related Lateral Inhibitor Encoded by *scabrous*," *Science* 250:1370–1377 (1990).
Corbin et al., "A Role for the Drosophila Neurogenic Genes in Mesoderm Differentiation," *Cell* 67:311–323 (1991).
Couso and Arias, "Notch is required for *wingless* Signaling in the Epidermis of Drosophila," *Cell* 79:259–272 (1994).
Deleuze et al., "Mapping of Microsatellite Markers in the Alagille Region and Screening of Microdeletions by Genotyping 23 Patients," *Eur. J. Hum. Genet.* 2:185–190 (1994).
Ellisen et al., "*TAN*–1, the Human Homolog of the Drosophila Notch Gene, Is Broken by Chromosomal Translocations in T Lymphoblastic Neoplasms," *Cell* 66:649–661 (1991).
Fuller et al., "Making Decisions: Role of Hematopoietic Growth Factors in Lineage Commitment and Maturation," *Hematopoiesis Keystone Symposia* (1997).

GenBank accession U61276 and statement from GenBank User Services regarding date of first public release (Jul. 23, 1996).
GenBank accession U77720 and statement from GenBank User Services regarding date of first public release (Nov. 25, 1996).
GenBank accession U77914 and statement from GenBank User Services regarding date of first public release (Nov. 25, 1996).
Henderson et al., "*lag*–2 may encode a signaling ligand for the GLP–1 and LIN–12 Receptors of *C. elegans*," *Development* 120:2913–2924 (1994).
Krantz et al., "Alagille syndrome," *J. Med. Genet.* 34:152–157 (1997).
Krantz et al., "Deletions of 20p12 in Alagille Syndrome: Frequency and Molecular Characterization," *Am. J. Med. Genet.* 70:80–86 (1997).
Li et al., "Alagille syndrome is caused by mutations in human *Jagged1*, which encodes a ligand for Notch1," *Nature Genetics* 16:243–251 (1997).
Li et al., "The Human Homolog of Rat *Jagged1* Expressed by Marrow Stroma Inhibits Differentiation of 32D cells through Interaction with Notch1," *Immunity* 8:43–55 (1998).
Lindsell et al., "Jagged: A Mammalian Ligand That Activates Notch1," *Cell* 80:909–917 (1995).
McAdams et al., "Hematopoietic cell culture therapies (Part 1) : cell culture considerations," *Trends in Biotech.* 14:341–349 (1996).
Milner et al., "A Human Homologue of the Drosophila Developmental Gene, *Notch*, Is Expressed in $CD34_+$ Hematopoietic Precursors," *Blood* 83 (8) : 2057–2062 (1994).
Milner et al., "Inhibition of granulocytic differentiation by *mNotch1*," *Proc. Natl. Acad. Sci.* 93:13014–13019 (1996).
Nye and Kopan, "Vertebrate ligands for Notch," *Current Biology* 5 (9) : 966–969 (1995).

(List continued on next page.)

Primary Examiner—Lorraine Spector
Assistant Examiner—Jegatheesan Seharaseyon
(74) Attorney, Agent, or Firm—McDermott, Will & Emery

(57) ABSTRACT

The present invention provides an isolated polypeptide exhibiting substantially the same amino acid sequence as JAGGED, or an active fragment thereof, provided that the polypeptide does not have the amino acid sequence of SEQ ID NO:5 or SEQ ID NO:6. The invention further provides an isolated nucleic acid molecule containing a nucleotide sequence encoding substantially the same amino acid sequence as JAGGED, or an active fragment thereof, provided that the nucleotide sequence does not encode the amino acid sequence of SEQ ID NO:5 or SEQ ID NO:6. Also provided herein is a method of inhibiting differentiation of hematopoietic progenitor cells by contacting the progenitor cells with an isolated JAGGED polypeptide, or active fragment thereof. The invention additionally provides a method of diagnosing Alagille Syndrome in an individual. The method consists of detecting an Alagille Syndrome disease-associated mutation linked to a JAGGED locus.

22 Claims, 31 Drawing Sheets

OTHER PUBLICATIONS

Nye et al., "An activated Notch suppresses neurogenesis and myogenesis but not gliogenesis in mammalian cells," *Development* 120:2421–2430 (1994).

Oda et al., "Mutations in the human Jagged1 gene are responsible for Alagille syndrome," *Nature Genetics* 16 : 235–242 (1997).

Oda et al., "Identification and cloning of the human homolog (JAG1) of the rat Jagged1 gene from the Alagille syndrome critical region at 20p12," *Genomics* 43 (3) :376–379 (1997).

Pollet et al., "Construction of a 3.7–Mb Physical Map within Human Chromosome 20p12 Ordering 18 Markers in the Alagille Syndrome Locus," *Genomics* 27:467–474 (1995).

Rand et al., "Molecular Analysis of 24 Alagille Syndrome Families Identifies a Single Submicroscopic Deletion and Further Localizes the Alagille Region within 20p12," *Am. J. Hum. Genet.* 57:1068–1073 (1995).

Robey et al., "An Activated Form of Notch Influences the Choice Between CD4 and CD8 T Cell Lineages," *Cell* 87:483–492 (1996).

Roecklein and Torok–Storb, "Functionally Distinct Human Marrow Stromal Cell Lines Immortalized by Transduction With the Human Papilloma Virus E6/E7 Genes," *Blood* 85 (4) :997–1005 (1995).

Schnittger et al., "Molecular and cytogenetic analysis of an Interstitial 20p deletion associated with syndromic intrahepatic ductular hypoplasia (Alagille syndrome) ," *Hum. Genet.* 83:239–244 (1989).

Shawber et al., "*Jagged2*: A Serrate–like Gene Expressed during Rat Embryogenesis," *Dev. Biol.* 180:370–376 (1996).

Simpson, "The Notch connection," *Nature* 375:736–737 (1995).

Spinner et al., "Cytologically Balanced t(2;20) in a Two–Generation Family with Alagille Syndrome: Cytogenetic and Molecular Studies," *Am. J. Hum. Genet.* 55:238–243 (1994).

Tax et al., "Sequence of *C. elegans* lag–2 reveals a cell–signaling domain shared with Delta and Serrate of Drosophilia," *Nature* 368:150–154 (1994).

Thiemann et al., "Retroviral Transduction of CD34+ Subpopulations on AFT024 Stroma," *Hematopoiesis Keystone Symposia* #419 (1997).

Zimrin et al., "An Antisense Oligonucleotide to the Notch Ligand Jagged Enhances Fibroblast Growth Factor–induced Angiogenesis in Vitro," *J. Biol. Chem.* 271(51) : 32499–32502 (1996).

* cited by examiner

```
     CTGCGGCCGGCCCGCGAGCTAGGCTGGGTTTTTTTTTTCTCCCCTCCCTCCCCCCTTTT
  1  ---------+---------+---------+---------+---------+---------+  60

TCCATGCAGCTGATCTAAAAGGGAATAAAAGGCTGCGCATAATCATAATAATAAAAGAAG
 61  ---------+---------+---------+---------+---------+---------+ 120

GGGAGCGCGAGAGAAGGAAAGAAAGCCGGGAGGTGGAAGAGGAGGGGGAGCGTCTCAAAG
121  ---------+---------+---------+---------+---------+---------+ 180

AAGCGATCAGAATAATAAAAGGAGGCCGGGCTCTTTGCCTTCTGGAACGGGCCGCTCTTG
181  ---------+---------+---------+---------+---------+---------+ 240

AAAGGGCTTTTGAAAAGTGGTGTTGTTTTCCAGTCGTGCATGCTCCAATCGGCGGAGTAT
241  ---------+---------+---------+---------+---------+---------+ 300

ATTAGAGCCGGGACGCGGCGGCCGCAGGGGCAGCGGCGACGGCAGCACCGGCGGCAGCAC
301  ---------+---------+---------+---------+---------+---------+ 360

CAGCGCGAACAGCAGCGGCGGCGTCCCGAGTGCCCGCGGCGCGCGGCGCAGCGATGCGTT
361  ---------+---------+---------+---------+---------+---------+ 420

M  R  S
     CCCCACGGACGCGCGGCCGGTCCGGGCGCCCCCTAAGCCTCCTGCTCGCCCTGCTCTGTG
421  ---------+---------+---------+---------+---------+---------+ 480

P  R  T  R  G  R  S  G  R  P  L  S  L  L  L  A  L  L  C  A
     CCCTGCGAGCCAAGGTGTGTGGGGCCTCGGGTCAGTTCGAGTTGGAGATCCTGTCCATGC
481  ---------+---------+---------+---------+---------+---------+ 540

L  R  A  K  V  C  G  A  S  G  Q  F  E  L  E  I  L  S  M  Q
     AGAACGTGAACGGGGAGCTGCAGAACGGGAACTGCTGCGGCGGCGCCCGGAACCCGGGAG
541  ---------+---------+---------+---------+---------+---------+ 600

N  V  N  G  E  L  Q  N  G  N  C  C  G  G  A  R  N  P  G  D
     ACCGCAAGTGCACCCGCGACGAGTGTGACACATACTTCAAAGTGTGCCTCAAGGAGTATC
601  ---------+---------+---------+---------+---------+---------+ 660

R  K  C  T  R  D  E  C  D  T  Y  F  K  V  C  L  K  E  Y  Q
     AGTCCCGCGTCACGGCCGGGGGGCCCTGCAGCTTCGGCTCAGGGTCCACGCCTGTCATCG
661  ---------+---------+---------+---------+---------+---------+ 720

```
     GGGGCAACACCTTCAACCTCAAGGCCAGCCGCGGCAACGACCGCAACCGCATCGTGCTGC
721  ---------+---------+---------+---------+---------+---------+  780
      G  N  T  F  N  L  K  A  S  R  G  N  D  R  N  R  I  V  L  P

CTTTCAGTTTCGCCTGGCCGAGGTCCTATACGTTGCTTGTGGAGGCGTGGGATTCCAGTA
781  ---------+---------+---------+---------+---------+---------+  840
      F  S  F  A  W  P  R  S  Y  T  L  L  V  E  A  W  D  S  S  N

ATGACACCGTTCAACCTGACAGTATTATTGAAAAGGCTTCTCACTCGGGCATGATCAACC
841  ---------+---------+---------+---------+---------+---------+  900
      D  T  V  Q  P  D  S  I  I  E  K  A  S  H  S  G  M  I  N  P

CCAGCCGGCAGTGGCAGACGCTGAAGCAGAACACGGGCGTTGCCCACTTTGAGTATCAGA
901  ---------+---------+---------+---------+---------+---------+  960
       S  R  Q  W  Q  T  L  K  Q  N  T  G  V  A  H  F  E  Y  Q  I

TCCGCGTGACCTGTGATGACTACTACTATGGCTTTGGCTGCAATAAGTTCTGCCGCCCCA
961  ---------+---------+---------+---------+---------+---------+  1020
       R  V  T  C  D  D  Y  Y  Y  G  F  G  C  N  K  F  C  R  P  R

GAGATGACTTCTTTGGACACTATGCCTGTGACCAGAATGGCAACAAAACTTGCATGGAAG
1021 ---------+---------+---------+---------+---------+---------+  1080
       D  D  F  F  G  H  Y  A  C  D  Q  N  G  N  K  T  C  M  E  G

GCTGGATGGGCCCCGAATGTAACAGAGCTATTTGCCGACAAGGCTGCAGTCCTAAGCATG
1081 ---------+---------+---------+---------+---------+---------+  1140
       W  M  G  P  E  C  N  R  A  I  C  R  Q  G  C  S  P  K  H  G

GGTCTTGCAAACTCCCAGGTGACTGCAGGTGCCAGTATGGCTGGCAAGGCCTGTACTGTG
1141 ---------+---------+---------+---------+---------+---------+  1200
       S  C  K  L  P  G  D  C  R  C  Q  Y  G  W  Q  G  L  Y  C  D

ATAAGTGCATCCCACACCCGGGATGCGTCCACGGCATCTGTAATGAGCCCTGGCAGTGCC
1201 ---------+---------+---------+---------+---------+---------+  1260
       K  C  I  P  H  P  G  C  V  H  G  I  C  N  E  P  W  Q  C  L
```

FIG. 1A-2

```
      TCTGTGAGACCAACTGGGGCGGCCAGCTCTGTGACAAAGATCTCAATTACTGTGGGACTC
1261  ---------+---------+---------+---------+---------+---------+  1320
        C  E  T  N  W  G  G  Q  L  C  D  K  D  L  N  Y  C  G  T  H

ATCAGCCGTGTCTCAACGGGGGAACTTGTAGCAACACAGGCCCTGACAAATATCAGTGTT
1321  ---------+---------+---------+---------+---------+---------+  1380
         Q  P  C  L  N  G  G  T  C  S  N  T  G  P  D  K  Y  Q  C  S

CCTGCCCTGAGGGGTATTCAGGACCCAACTGTGAAATTGCTGAGCACGCCTGCCTCTCTG
1381  ---------+---------+---------+---------+---------+---------+  1440
         C  P  E  G  Y  S  G  P  N  C  E  I  A  E  H  A  C  L  S  D

ATCCCTGTCACAACAGAGGCAGCTGTAAGGAGACCTCCCTGGGCTTTGAGTGTGAGTGTT
1441  ---------+---------+---------+---------+---------+---------+  1500
         P  C  H  N  R  G  S  C  K  E  T  S  L  G  F  E  C  E  C  S

CCCCAGGCTGGACCGGCCCCACATGCTCTACAAACATTGATGACTGTTCTCCTAATAACT
1501  ---------+---------+---------+---------+---------+---------+  1560
         P  G  W  T  G  P  T  C  S  T  N  I  D  D  C  S  P  N  N  C

GTTCCCACGGGGGCACCTGCCAGGACCTGGTTAACGGATTTAAGTGTGTGTGCCCCCCAC
1561  ---------+---------+---------+---------+---------+---------+  1620
         S  H  G  G  T  C  Q  D  L  V  N  G  F  K  C  V  C  P  P  Q

AGTGGACTGGGAAAACGTGCCAGTTAGATGCAAATGAATGTGAGGCCAAACCTTGTGTAA
1621  ---------+---------+---------+---------+---------+---------+  1680
         W  T  G  K  T  C  Q  L  D  A  N  E  C  E  A  K  P  C  V  N

ACGCCAAATCCTGTAAGAATCTCATTGCCAGCTACTACTGCGACTGTCTTCCCGGCTGGA
1681  ---------+---------+---------+---------+---------+---------+  1740
         A  K  S  C  K  N  L  I  A  S  Y  Y  C  D  C  L  P  G  W  M

TGGGTCAGAATTGTGACATAAATATTAATGACTGCCTTGGCCAGTGTCAGAATGACGCCT
1741  ---------+---------+---------+---------+---------+---------+  1800
         G  Q  N  C  D  I  N  I  N  D  C  L  G  Q  C  Q  N  D  A  S

CCTGTCGGGATTTGGTTAATGGTTATCGCTGTATCTGTCCACCTGGCTATGCAGGCGATC
1801  ---------+---------+---------+---------+---------+---------+  1860
         C  R  D  L  V  N  G  Y  R  C  I  C  P  P  G  Y  A  G  D  H
```

FIG. 1A-3

```
      ACTGTGAGAGAGACATCGATGAATGTGCCAGCAACCCCTGTTTGAATGGGGGTCACTGTC
1861  ------------------------------------------------------------  1920
        C   E   R   D   I   D   E   C   A   S   N   P   C   L   N   G   G   H   C   Q

AGAATGAAATCAACAGATTCCAGTGTCTGTGTCCCACTGGTTTCTCTGGAAACCTCTGTC
1921  ------------------------------------------------------------  1980
        N   E   I   N   R   F   Q   C   L   C   P   T   G   F   S   G   N   L   C   Q

AGCTGGACATCGATTATTGTGAGCCTAATCCCTGCCAGAACGGTGCCCAGTGCTACAACC
1981  ------------------------------------------------------------  2040
        L   D   I   D   Y   C   E   P   N   P   C   Q   N   G   A   Q   C   Y   N   R

TGAAAGACCACTGCCGCACGACCCCCTGTGAAGTGATTGACAGCTGCACAGTGGCCATGG
2041  ------------------------------------------------------------  2100
        A   S   D   Y   F   C   K   C   P   E   D   Y   E   G   K   N   C   S   H   L

TGAAAGACCACTGCCGCACGACCCCCTGTGAAGTGATTGACAGCTGCACAGTGGCCATGG
2101  ------------------------------------------------------------  2160
        K   D   H   C   R   T   T   P   C   E   V   I   D   S   C   T   V   A   M   A

CTTCCAACGACACACCTGAAGGGGTGCGGTATATTTCCTCCAACGTCTGTGGTCCTCACG
2161  ------------------------------------------------------------  2220
        S   N   D   T   P   E   G   V   R   Y   I   S   S   N   V   C   G   P   H   G

GGAAGTGCAAGAGTCAGTCGGGAGGCAAATTCACCTGTGACTGTAACAAAGGCTTCACGG
2221  ------------------------------------------------------------  2280
        K   C   K   S   Q   S   G   G   K   F   T   C   D   C   N   K   G   F   T   G

GAACATACTGCCATGAAAATATTAATGACTGTGAGAGCAACCCTTGTAGAAACGGTGGCA
2281  ------------------------------------------------------------  2340
        T   Y   C   H   E   N   I   N   D   C   E   S   N   P   C   R   N   G   G   T

CTTGCATCGATGGTGTCAACTCCTACAAGTGCATCTGTAGTGACGGCTGGGAGGGGGCCT
2341  ------------------------------------------------------------  2400
        C   I   D   G   V   N   S   Y   K   C   I   C   S   D   G   W   E   G   A   Y
```

FIG. 1A-4

```
       ACTGTGAAACCAATATTAATGACTGCAGCCAGAACCCCTGCCACAATGGGGGCACGTGTC
2401   ---------+---------+---------+---------+---------+---------+   2460
         C  E  T  N  I  N  D  C  S  Q  N  P  C  H  N  G  G  T  C  R

GCGACCTGGTCAATGACTTCTACTGTGACTGTAAAAATGGGTGGAAAGGAAAGACCTGCC
2461   ---------+---------+---------+---------+---------+---------+   2520
         D  L  V  N  D  F  Y  C  D  C  K  N  G  W  K  G  K  T  C  H

ACTCACGTGACAGTCAGTGTGATGAGGCCACGTGCAACAACGGTGGCACCTGCTATGATG
2521   ---------+---------+---------+---------+---------+---------+   2580
         S  R  D  S  Q  C  D  E  A  T  C  N  N  G  G  T  C  Y  D  E

AGGGGGATGCTTTTAAGTGCATGTGTCCTGGCGGCTGGGAAGGAACAACCTGTAACATAG
2581   ---------+---------+---------+---------+---------+---------+   2640
         G  D  A  F  K  C  M  C  P  G  G  W  E  G  T  T  C  N  I  A

CCCGAAACAGTAGCTGCCTGCCCAACCCCTGCCATAATGGGGGCACATGTGTGGTCAACG
2641   ---------+---------+---------+---------+---------+---------+   2700
         R  N  S  S  C  L  P  N  P  C  H  N  G  G  T  C  V  V  N  G

GCGAGTCCTTTACGTGCGTCTGCAAGGAAGGCTGGGAGGGGCCCATCTGTGCTCAGAATA
2701   ---------+---------+---------+---------+---------+---------+   2760
         E  S  F  T  C  V  C  K  E  G  W  E  G  P  I  C  A  Q  N  T

CCAATGACTGCAGCCCTCATCCCTGTTACAACAGCGGCACCTGTGTGGATGGAGACAACT
2761   ---------+---------+---------+---------+---------+---------+   2820
         N  D  C  S  P  H  P  C  Y  N  S  G  T  C  V  D  G  D  N  W

GGTACCGGTGCGAATGTGCCCCGGGTTTTGCTGGGCCCGACTGCAGAATAAACATCAATG
2821   ---------+---------+---------+---------+---------+---------+   2880
         Y  R  C  E  C  A  P  G  F  A  G  P  D  C  R  I  N  I  N  E

AATGCCAGTCTTCACCTTGTGCCTTTGGAGCGACCTGTGTGGATGAGATCAATGGCTACC
2881   ---------+---------+---------+---------+---------+---------+   2940
         C  Q  S  S  P  C  A  F  G  A  T  C  V  D  E  I  N  G  Y  R

GGTGTGTCTGCCCTCCAGGGCACAGTGGTGCCAAGTGCCAGGAAGTTTCAGGGAGACCTT
2941   ---------+---------+---------+---------+---------+---------+   3000
         C  V  C  P  P  G  H  S  G  A  K  C  Q  E  V  S  G  R  P  C
```

FIG. 1A-5

```
        GCATCACCATGGGGAGTGTGATACCAGATGGGGCCAAATGGGATGATGACTGTAATACCT
3001    ---------+---------+---------+---------+---------+---------+    3060
         I  T  M  G  S  V  I  P  D  G  A  K  W  D  D  D  C  N  T  C

GCCAGTGCCTGAATGGACGGATCGCCTGCTCAAAGGTCTGGTGTGGCCCTCGACCTTGCC
3061    ---------+---------+---------+---------+---------+---------+    3120
          Q  C  L  N  G  R  I  A  C  S  K  V  W  C  G  P  R  P  C  L

TGCTCCACAAAGGGCACAGCGAGTGCCCCAGCGGGCAGAGCTGCATCCCCATCCTGGACG
3121    ---------+---------+---------+---------+---------+---------+    3180
          L  H  K  G  H  S  E  C  P  S  G  Q  S  C  I  P  I  L  D  D

ACCAGTGCTTCGTCCACCCCTGCACTGGTGTGGGCGAGTGTCGGTCTTCCAGTCTCCAGC
3181    ---------+---------+---------+---------+---------+---------+    3240
          Q  C  F  V  H  P  C  T  G  V  G  E  C  R  S  S  L  Q  P

CGGTGAAGACAAAGTGCACCTCTGACTCCTATTACCAGGATAACTGTGCGAACATCACAT
3241    ---------+---------+---------+---------+---------+---------+    3300
           V  K  T  K  C  T  S  D  S  Y  Y  Q  D  N  C  A  N  I  T  F

TTACCTTTAACAAGGAGATGATGTCACCAGGTCTTACTACGGAGCACATTTGCAGTGAAT
3301    ---------+---------+---------+---------+---------+---------+    3360
           T  F  N  K  E  M  M  S  P  G  L  T  T  E  H  I  C  S  E  L

TGAGGAATTTGAATATTTTGAAGAATGTTTCCGCTGAATATTCAATCTACATCGCTTGCG
3361    ---------+---------+---------+---------+---------+---------+    3420
           R  N  L  N  I  L  K  N  V  S  A  E  Y  S  I  Y  I  A  C  E

AGCCTTCCCCTTCAGCGAACAATGAAATACATGTGGCCATTTCTGCTGAAGATATACGGG
3421    ---------+---------+---------+---------+---------+---------+    3480
           P  S  P  S  A  N  N  E  I  H  V  A  I  S  A  E  D  I  R  D

ATGATGGGAACCCGATCAAGGAAATCACTGACAAAATAATCGATCTTGTTAGTAAACGTG
3481    ---------+---------+---------+---------+---------+---------+    3540
           D  G  N  P  I  K  E  I  T  D  K  I  I  D  L  V  S  K  R  D

ATGGAAACAGCTCGCTGATTGCTGCCGTTGCAGAAGTAAGAGTTCAGAGGCGGCCTCTGA
3541    ---------+---------+---------+---------+---------+---------+    3600
           G  N  S  S  L  I  A  A  V  A  E  V  R  V  Q  R  R  P  L  K
```

FIG. 1A-6

```
      AGAACAGAACAGATTTCCTTGTTCCCTTGCTGAGCTCTGTCTTAACTGTGGCTTGGATCT
3601  ---------+---------+---------+---------+---------+---------+  3660
       N  R  T  D  F  L  V  P  L  L  S  S  V  L  T  V  A  W  I  C

GTTGCTTGGTGACGGCCTTCTACTGGTGCCTGCGGAAGCGGCGGAAGCCGGGCAGCCACA
3661  ---------+---------+---------+---------+---------+---------+  3720
       C  L  V  T  A  F  Y  W  C  L  R  K  R  R  K  P  G  S  H  T

CACACTCAGCCTCTGAGGACAACACCACCAACAACGTGCGGGAGCAGCTGAACCAGATCA
3721  ---------+---------+---------+---------+---------+---------+  3780
       H  S  A  S  E  D  N  T  T  N  N  V  R  E  Q  L  N  Q  I  K

AAAACCCCATTGAGAAACATGGGGCCAACACGGTCCCCATCAAGGATTACGAGAACAAGA
3781  ---------+---------+---------+---------+---------+---------+  3840
       N  P  I  E  K  H  G  A  N  T  V  P  I  K  D  Y  E  N  K  N

ACTCCAAAATGTCTAAAATAAGGACACACAATTCTGAAGTAGAAGAGGACGACATGGACA
3841  ---------+---------+---------+---------+---------+---------+  3900
       S  K  M  S  K  I  R  T  H  N  S  E  V  E  E  D  D  M  D  K

AACACCAGCAGAAAGCCCGGTTTGCCAAGCAGCCGGCGTATACGCTGGTAGACAGAGAAG
3901  ---------+---------+---------+---------+---------+---------+  3960
       H  Q  Q  K  A  R  F  A  K  Q  P  A  Y  T  L  V  D  R  E  E

AGAAGCCCCCCAACGGCACGCCGACAAAACACCCAAACTGGACAAACAAACAGGACAACA
3961  ---------+---------+---------+---------+---------+---------+  4020
       K  P  P  N  G  T  P  T  K  H  P  N  W  T  N  K  Q  D  N  R

GAGACTTGGAAAGTGCCCAGAGCTTAAACCGAATGGAGTACATCGTATAGCAGACCGCGG
4021  ---------+---------+---------+---------+---------+---------+  4080
       D  L  E  S  A  Q  S  L  N  R  M  E  Y  I  V  *

GCACTGCCGCCGCTAGGTAGAGTCTGAGGGCTTGTAGTTCTTTAAACTGTCGTGTCATAC
4081  ---------+---------+---------+---------+---------+---------+  4140

TCGAGTCTGAGGCCGTTGCTGACTTAGAATCCCTGTGTTAATTTAAGTTTTGACAAGCTG
4141  ---------+---------+---------+---------+---------+---------+  4200

GCTTACACTGGCAATGGTAGTTTCTGTGGTTGGCTGGGAAATCGAGTGCCGCATCTCACA
4201  ---------+---------+---------+---------+---------+---------+  4260
```

FIG. 1A-7

```
     GCTATGCAAAAAGCTAGTCAACAGTACCCTGGTTGTGTGTCCCCTTGCAGCCGACACGGT
4261 ---------+---------+---------+---------+---------+---------+ 4320

CTCGGATCAGGCTCCCAGGAGCCTGCCCAGCCCCTGGTCTTTGAGCTCCCACTTCTGCC
4321 ---------+---------+---------+---------+---------+---------+ 4380

AGATGTCCTAATGGTGATGCAGTCTTAGATCATAGTTTTATTTATATTTATTGACTCTTG
4381 ---------+---------+---------+---------+---------+---------+ 4440

AGTTGTTTTTGTATATTGGTTTTATGATGACGTACAAGTAGTTCTGTATTTGAAAGTGCC
4441 ---------+---------+---------+---------+---------+---------+ 4500

TTTGCAGCTCAGAACCACAGCAACGATCACAAATGACTTTATTATTTATTTTTTTAATTG
4501 ---------+---------+---------+---------+---------+---------+ 4560

TATTTTGTTGTTGGGGGAGGGGAGACTTTGATGTCAGCAGTTGCTGGTAAAATGAAGAA
4561 ---------+---------+---------+---------+---------+---------+ 4620

TTTAAAGAAAAAAATGTCAAAAGTAGAACTTTGTATAGTTATGTAAATAATTCTTTTTTA
4621 ---------+---------+---------+---------+---------+---------+ 4680

TTAATCACTGTGTATATTTGATTTATTAACTTAATAATCAAGAGCCTTAAAACATCATTC
4681 ---------+---------+---------+---------+---------+---------+ 4740

CTTTTTATTTATATGTATGTGTTTAGAATTGAAGGTTTTTGATAGCATTGTAAGCGTATG
4741 ---------+---------+---------+---------+---------+---------+ 4800

GCTTTATTTTTTTGAACTCTTCTCATTACTTGTTGCCTATAAGCCAAAATTAAGGTGTTT
4801 ---------+---------+---------+---------+---------+---------+ 4860

GAAAATAGTTTATTTTAAAACAATAGGATGGGCTTCTGTGCCCAGAATACTGATGGAATT
4861 ---------+---------+---------+---------+---------+---------+ 4920

TTTTTTGTACGACGTCAGATGTTTAAAACACCTTCTATAGCATCACTTAAAACACGTTTT
4921 ---------+---------+---------+---------+---------+---------+ 4980

AAGGACTGACTGAGGCAGTTTGAGGATTAGTTTAGAACAGGTTTTTTTGTTTGTTTGTTT
4981 ---------+---------+---------+---------+---------+---------+ 5040
```

FIG. 1A-8

```
5041  TTTGTTTTTCTGCTTTAGACTTGAAAAGAGACAGGCAGGTGATCTGCTGCAGAGCAGTAA
      ---------+---------+---------+---------+---------+---------+  5100

5101  GGGAACAAGTTGAGCTATGACTTAACATAGCCAAAATGTGAGTGGTTGAATATGATTAAA
      ---------+---------+---------+---------+---------+---------+  5160

5161  AATATCAAATTAATTGTGTGAACTTGGAAGCACACCAATCTGACTTTGTAAATTCTGATT
      ---------+---------+---------+---------+---------+---------+  5220

5221  TCTTTTCACCATTCGTACATAATACTGAACCACTTGTAGATTTGATTTTTTTTTAATCT
      ---------+---------+---------+---------+---------+---------+  5280

5281  ACTGCATTTAGGGAGTATTCTAATAAGCTAGTTGAATACTTGAACCATAAAATGTCCAGT
      ---------+---------+---------+---------+---------+---------+  5340

5341  AAGATCACTGTTTAGATTTGCCATAGAGTACACTGCCCTGCCTTAAGTGAGGAAATCAAG
      ---------+---------+---------+---------+---------+---------+  5400

5401  TGCTATTACGAAGTTCAAGATCAAAAAGGCTTATAAAACAGAGTAATCTTGTTGGTTCAC
      ---------+---------+---------+---------+---------+---------+  5460

5461  CATTGAGACCGTGAAGATACTTTGTATTGTCCTATTAGTGTTATATGAACATACAAATGC
      ---------+---------+---------+---------+---------+---------+  5520

5521  ATCTTTGATGTGTTGTTCTTGGCAATAAATTTTGAAAAGTAATATTTATTAAATTTTTTT
      ---------+---------+---------+---------+---------+---------+  5580

5581  GTATGAAAAC
      ---------+  5590
```

FIG. 1A-9

```
    CGGCCGCGTCGACGTGACGGCGACGGCCGGACAACGCGCGCGGGGGGCTGCGGCCACGAC
1   ---------+---------+---------+---------+---------+---------+   60

D  G  D  G  R  T  T  R  A  G  G  C  G  H  D

GAGTGCGACACGTACGTGCGCGTGTGCCTTAAGGAGTACCAGGCCAAGGTGACGCCCACG
61  ---------+---------+---------+---------+---------+---------+   120

E  C  D  T  Y  V  R  V  C  L  K  E  Y  Q  A  K  V  T  P  T

GGGCCCTGCAGCTACGGCCACGGCGCCACGCCCGTGCTGGGCGGCAACTCCTTCTACCTG
121 ---------+---------+---------+---------+---------+---------+   180

G  P  C  S  Y  G  H  G  A  T  P  V  L  G  G  N  S  F  Y  L

CCGCCGGCGGGCGCTGCGGGGGACCGAGCGCGGGCGCGGGCCCGGGCCGGCGGCGACCAG
181 ---------+---------+---------+---------+---------+---------+   240

P  P  A  G  A  A  G  D  R  A  R  A  R  A  R  A  G  G  D  Q

GACCCGGGCCTCGTCGTCATCCCCTTCCAGTTCGCCTGGCCGCGCTCCTTTACCCTCATC
241 ---------+---------+---------+---------+---------+---------+   300
                                                          GGAGTAG
    D  P  G  L  V  V  I  P  F  Q  F  A  W  P  R  S  F  T  L  I

GTGGAGGCCTGGGACTGGGACAACGATACCACCCCGAATGAGGAGCTGCTGATCGAGCGA
301 ---------+---------+---------+---------+---------+---------+   360

V  E  A  W  D  W  D  N  D  T  T  P  N  E  E  L  L  I  E  R

GTGTCGCATGCCGGCATGATCAACCCGGAGGACCGCTGGAAGAGCCTGCACTTCAGCGGC
361 ---------+---------+---------+---------+---------+---------+   420

V  S  H  A  G  M  I  N  P  E  D  R  W  K  S  L  H  F  S  G

CACGTGGCGCACCTGGAGCTGCAGATCCGCGTGCGCTGCGACGAGAACTACTACAGCGCC
421 ---------+---------+---------+---------+---------+---------+   480

H  V  A  H  L  E  L  Q  I  R  V  R  C  D  E  N  Y  Y  S  A

ACTTGCAACAAGTTCTGCCGGCCCCGCAACGACTTTTTCGGCCACTACACCTGCGACCAG
481 ---------+---------+---------+---------+---------+---------+   540

T  C  N  K  F  C  R  P  R  N  D  F  F  G  H  Y  T  C  D  Q

TACGGCAACAAGGCCTGCATGGACGGCTGGATGGGCAAGGAGTGCAAGGAAGCTGTGTGT
541 ---------+---------+---------+---------+---------+---------+   600

```
     AAACAAGGGTGTAATTTGCTCCACGGGGGATGCACCGTGCCTGGGGAGTGCAGGTGCAGC
601  ------------+---------+---------+---------+---------+---------+  660
     K  Q  G  C  N  L  L  H  G  G  C  T  V  P  G  E  C  R  C  S

TACGGCTGGCAAGGGAGGTTCTGCGATGAGTGTGTCCCCTACCCCGGCTGCGTGCATGGC
661  ------------+---------+---------+---------+---------+---------+  720
     Y  G  W  Q  G  R  F  C  D  E  C  V  P  Y  P  G  C  V  H  G

AGTTGTGTGGAGCCCTGGCAGTGCAACTGTGAGACCAACTGGGGCGGCCTGCTCTGTGAC
721  ------------+---------+---------+---------+---------+---------+  780
     S  C  V  E  P  W  Q  C  N  C  E  T  N  W  G  G  L  L  C  D

AAAGACCTGAACTACTGTGGCAGCCACCACCCCTGCACCAACGGAGGCACGTGCATCAAC
781  ------------+---------+---------+---------+---------+---------+  840
     K  D  L  N  Y  C  G  S  H  H  P  C  T  N  G  G  T  C  I  N

GCCGAGCCTGACCAGTACCGCTGCACCTGCCCTGACGGCTACTCGGGCAGGAACTGTGAG
841  ------------+---------+---------+---------+---------+---------+  900
     A  E  P  D  Q  Y  R  C  T  C  P  D  G  Y  S  G  R  N  C  E

AAGGCTGAGCACGCCTGCACCTCCAACCCGTGTGCCAACGGGGGCTCTTGCCATGAGGTG
901  ------------+---------+---------+---------+---------+---------+  960
     K  A  E  H  A  C  T  S  N  P  C  A  N  G  G  S  C  H  E  V

CCGTCCGGCTTCGAATGCCACTGCCCATCGGGCTGGAGCGGGCCCACCTGTGCCCTTGAC
961  ------------+---------+---------+---------+---------+---------+ 1020
     P  S  G  F  E  C  H  C  P  S  G  W  S  G  P  T  C  A  L  D

ATCGATGAGTGTGCTTCGAACCCGTGTGCGGCCGGTGGCACCTGTGTGGACCAGGTGGAC
1021 ------------+---------+---------+---------+---------+---------+ 1080
     I  D  E  C  A  S  N  P  C  A  A  G  G  T  C  V  D  Q  V  D

GGCTTTGAGTGCATCTGCCCCGAGCAGTGGGTGGGGGCCACCTGCCAGCTGGACGTCAAC
1081 ------------+---------+---------+---------+---------+---------+ 1140
     G  F  E  C  I  C  P  E  Q  W  V  G  A  T  C  Q  L  D  V  N

GACTGTCGCGGGCAGTGTCAGCATGGGGGCACCTGCAAGGACCTGGTGAACGGGTACCAG
1141 ------------+---------+---------+---------+---------+---------+ 1200
     D  C  R  G  Q  C  Q  H  G  G  T  C  K  D  L  V  N  G  Y  Q
```

FIG. 1B-2

```
      TGTGTGTGCCCACGGGGCTTCGGAGGCCGGCATTGCGAGCTGGAACGAGACAAGTGTGCC
1201  ---------+---------+---------+---------+---------+---------+  1260
      C  V  C  P  R  G  F  G  G  R  H  C  E  L  E  R  D  K  C  A

AGCAGCCCCTGCCACAGCGGCGGCCTCTGCGAGGACCTGGCCGACGGCTTCCACTGCCAC
1261  ---------+---------+---------+---------+---------+---------+  1320
      S  S  P  C  H  S  G  G  L  C  E  D  L  A  D  G  F  H  C  H

TGCCCCCAGGGCTTCTCCGGGCCTCTCTGTGAGGTGGATGTCGACCTTTGTGAGCCAAGC
1321  ---------+---------+---------+---------+---------+---------+  1380
      C  P  Q  G  F  S  G  P  L  C  E  V  D  V  D  L  C  E  P  S

CCCTGCCGGAACGGCGCTCGCTGCTATAACCTGGAGGGTGACTATTACTGCGCCTGCCCT
1380  ---------+---------+---------+---------+---------+---------+  1440
      P  C  R  N  G  A  R  C  Y  N  L  E  G  D  Y  Y  C  A  C  P

GATGACTTTGGTGGCAAGAACTGCTCCGTGCCCCGCGAGCCGTGCTGGCGGGGCCTGCAG
1441  ---------+---------+---------+---------+---------+---------+  1500
      D  D  F  G  G  K  N  C  S  V  P  R  E  P  C  W  R  G  L  Q

AGTGATCGATGGCTGCGGGTCAGACGCGGGGCCTGGGATGCCTGGCACAGCACGTCCGGC
1501  ---------+---------+---------+---------+---------+---------+  1560
      S  D  R  W  L  R  V  R  R  G  A  W  D  A  W  H  S  T  S  G

GTGTGTGGCCCCCATGGACGCTGCGTCAGCCAGCCAGGGGGCAACTTTTCCTGCATCTGT
1561  ---------+---------+---------+---------+---------+---------+  1620
      V  C  G  P  H  G  R  C  V  S  Q  P  G  G  N  F  S  C  I  C

GACAGTGGCTTTACTGGCACCTACTGCCATGAGAACATTGACGACTGCCTGGGCCAGCCC
1621  ---------+---------+---------+---------+---------+---------+  1680
      D  S  G  F  T  G  T  Y  C  H  E  N  I  D  D  C  L  G  Q  P

TGCCGCAATGGGGGCACATGCATCGATGAGGTGGACGCCTTCCGCTGCTTCTGCCCCAGC
1681  ---------+---------+---------+---------+---------+---------+  1740
      C  R  N  G  G  T  C  I  D  E  V  D  A  F  R  C  F  C  P  S

GGCTGGGAGGGCGAGCTCTGCGACACCAATCCCAACGACTGCCTTCCCGATCCCTGCCAC
1741  ---------+---------+---------+---------+---------+---------+  1800
      G  W  E  G  E  L  C  D  T  N  P  N  D  C  L  P  D  P  C  H
```

FIG. 1B-3

```
1801  AGCCGCGGCCGCTGCTACGACCTGGTCAATGACTTCTACTGTGCGTGCGACGACGGCTGG  1860
       ---------+---------+---------+---------+---------+---------+
       S  R  G  R  C  Y  D  L  V  N  D  F  Y  C  A  C  D  D  G  W

1861  AAGGGCAAGACCTGCCACTCACGCGAGTTCCAGTGCGATGCCTACACCTGCAGCAACGGT  1920
       ---------+---------+---------+---------+---------+---------+
       K  G  K  T  C  H  S  R  E  F  Q  C  D  A  Y  T  C  S  N  G

1921  GGCACCTGCTACGACAGCGGCGACACCTTCCGCTGCGCCTGCCCCCCCGGCTGGAAGGGC  1980
       ---------+---------+---------+---------+---------+---------+
       G  T  C  Y  D  S  G  D  T  F  R  C  A  C  P  P  G  W  K  G

1981  AGCACCTGCGCCGTCGCCAAGAACAGCAGCTGCCTGCCCAACCCCTGTGTGAATGGTGGC  2040
       ---------+---------+---------+---------+---------+---------+
       S  T  C  A  V  A  K  N  S  S  C  L  P  N  P  C  V  N  G  G

2041  ACCTGCGTGGGCAGCGGGGCCTCCTTCTCCTGCATCTGCCGGGACGGCTGGGAGGGTCGT  2100
       ---------+---------+---------+---------+---------+---------+
       T  C  V  G  S  G  A  S  F  S  C  I  C  R  D  G  W  E  G  R

2101  ACTTGCACTCACAATACCAACGACTGCAACCCTCTGCCTTGCTACAATGGTGGCATCTGT  2160
       ---------+---------+---------+---------+---------+---------+
       T  C  T  H  N  T  N  D  C  N  P  L  P  C  Y  N  G  G  I  C

2161  GTTGACGGCGTCAACTGGTTCCGCTGCGAGTGTGCACCTGGCTTCGCGGGGCCTGACTGC  2220
       ---------+---------+---------+---------+---------+---------+
       V  D  G  V  N  W  F  R  C  E  C  A  P  G  F  A  G  P  D  C

2221  CGCATCAACATCGACGAGTGCCAGTCCTCGCCCTGTGCCTACGGGGCCACGTGTGTGGAT  2280
       ---------+---------+---------+---------+---------+---------+
       R  I  N  I  D  E  C  Q  S  S  P  C  A  Y  G  A  T  C  V  D

2281  GAGATCAACGGGTATCGCTGTAGCTGCCCACCCGGCCGAGCCGGCCCCCGGTGCCAGGAA  2340
       ---------+---------+---------+---------+---------+---------+
       E  I  N  G  Y  R  C  S  C  P  P  G  R  A  G  P  R  C  Q  E

2341  GTGATCGGGTTCGGGAGATCCTGCTGGTCCCGGGGCACTCCGTTCCCACACGGAAGCTCC  2400
       ---------+---------+---------+---------+---------+---------+
       V  I  G  F  G  R  S  C  W  S  R  G  T  P  F  P  H  G  S  S
```

FIG. 1B-4

```
       TGGGTGGAAGACTGCAACAGCTGCCGCTGCCTGGATGGCCGCCGTGACTGCAGCAAGGTG
2401   ---------+---------+---------+---------+---------+---------+   2460
       W   V   E   D   C   N   S   C   R   L   D   G   R   R   D   C   S   K   V

TGGTGCGGATGGAAGCCTTGTCTGCTGGCCGGCCAGCCCGAGGCCCTGAGCGCCCAGTGC
2461   ---------+---------+---------+---------+---------+---------+   2520
       W   C   G   W   K   P   C   L   L   A   G   Q   P   E   A   L   S   A   Q   C

CCACTGGGGCAAAGGTGCCTGGAGAAGGCCCCAGGCCAGTGTCTGCGACCACCCTGTGAG
2521   ---------+---------+---------+---------+---------+---------+   2580
       P   L   G   Q   R   C   L   E   K   A   P   G   Q   C   L   R   P   P   C   E

GCCTGGGGGGAGTGCGGCGCAGAAGAGCCACCGAGCACCCCCTGCCTGCCACGCTCCGGC
2581   ---------+---------+---------+---------+---------+---------+   2640
       A   W   G   E   C   G   A   E   E   P   P   S   T   P   C   L   P   R   S   G

CACCTGGACAATAACTGTGCCCGCCTCACCTTGCATTTCAACCGTGACCACGTGCCCCAG
2641   ---------+---------+---------+---------+---------+---------+   2700
       H   L   D   N   N   C   A   R   L   T   L   H   F   N   R   D   H   V   P   Q

GGCACCACGGTGGGCGCCATTTGCTCCGGGATCCGCTCCCTGCCAGCCACAAGGGCTGTG
2701   ---------+---------+---------+---------+---------+---------+   2760
       G   T   T   V   G   A   I   C   S   G   I   R   S   L   P   A   T   R   A   V

GCACGGGACCGCCTGCTGGTGTTGCTTTGCGACCGGGCGTCCTCGGGGGCCAGTGCCGTG
2761   ---------+---------+---------+---------+---------+---------+   2820
       A   R   D   R   L   L   V   L   L   C   D   R   A   S   S   G   A   S   A   V

GAGGTGGCCGTGTCCTTCAGCCCTGCCAGGGACCTGCCTGACAGCAGCCTGATCCAGGGC
2821   ---------+---------+---------+---------+---------+---------+   2880
       E   V   A   V   S   F   S   P   A   R   D   L   P   D   S   S   L   I   Q   G

GCGGCCCACGCCATCGTGGCCGCCATCACCCAGCGGGGGAACAGCTCACTGCTCCTGGCT
2881   ---------+---------+---------+---------+---------+---------+   2940
       A   A   H   A   I   V   A   A   I   T   Q   R   G   N   S   S   L   L   L   A

GTCACCGAGGTCAAGGTGGAGACGGTTGTTACGGGCGGCTCTTCCACAGGTCTGCTGGTG
2941   ---------+---------+---------+---------+---------+---------+   3000
```

FIG. 1B-5

```
            V  T  E  V  K  V  E  T  V  V  T  G  G  S  S  T  G  L  L  V
          CCTGTGCTGTGTGGTGCCTTCAGCGTGCTGTGGCTGGCGTGCGTGGTCCTGTGCGTGTGG
     3001 ---------+---------+---------+---------+---------+---------+ 3060
            P  V  L  C  G  A  F  S  V  L  W  L  A  C  V  V  L  C  V  W

TGGACACGCAAGCGCAGGAAAGAGCGGGAGAGGAGCCGGCTGCCGCGGGAGGAGAGCGCC
     3061 ---------+---------+---------+---------+---------+---------+ 3120
            W  T  R  K  R  R  K  E  R  E  R  S  R  L  P  R  E  E  S  A

AACAACCAGTGGGCCCCGCTCAACCCCATCCGCAACCCCATCGAGCGGCCGGGGGGCCAC
     3121 ---------+---------+---------+---------+---------+---------+ 3180
            N  N  Q  W  A  P  L  N  P  I  R  N  P  I  E  R  P  G  G  H

AAGGACGTGCTCTACCAGTGCAAGAACTTCACGCCGCCGCCGCGCAGGGCGGACGAGGCG
     3181 ---------+---------+---------+---------+---------+---------+ 3240
            K  D  V  L  Y  Q  C  K  N  F  T  P  P  P  R  R  A  D  E  A

CTGCCCGGGCCGGCGCGCCACGCGGCCGTCAGGGAGGATGAGGAGGACGAGGATCTGGGC
     3241 ---------+---------+---------+---------+---------+---------+ 3300
            L  P  G  P  A  R  H  A  A  V  R  E  D  E  E  D  E  D  L  G

CGCGGTGAGGAGGACTCCCTGGAGGCGGAGAAGTTCCTCTCACACAAATTCACCAAAGAT
     3301 ---------+---------+---------+---------+---------+---------+ 3360
            R  G  E  E  D  S  L  E  A  E  K  F  L  S  H  K  F  T  K  D

CCTGGCCGCTCGCCGGGGAGGCCCGCCCACTGGCCTCAGGCCCCAAAGTGGACAACCGCG
     3361 ---------+---------+---------+---------+---------+---------+ 3420
            P  G  R  S  P  G  R  P  A  H  W  P  Q  A  P  K  W  T  T  A

CGGTCAGGAGCATCAATGAGGCCCTACGCCGGCAAGGAGTAGGGGCGGCTGCCAGCTGGG
     3421 ---------+---------+---------+---------+---------+---------+ 3480
            R  S  G  A  S  M  R  P  Y  A  G  K  E  *

CCGGGACCCAGGGCCCTCGGTGGGAGCCATGCCGTCTGCCGGACCCGGAGGCCGAGGCCA
     3481 ---------+---------+---------+---------+---------+---------+ 3540

TGTGCATAGTTTCTTTATTTTGTGTAAAAAAACCACCAAAAACAAAAACCAAATGTTTAT
     3541 ---------+---------+---------+---------+---------+---------+ 3600

TTTCTACGTTTCTTTAACCTTGTATAAATTATTCAGTAACTGTCAGGCTGAAAACAATGG
     3601 ---------+---------+---------+---------+---------+---------+ 3660

AGTATTCTCGGATAGTTGCTATTTTTGTAAAGTTTCCGTGCGTGGCACTCGCTGTATGAA
     3661 ---------+---------+---------+---------+---------+---------+ 3720
```

FIG. 1B-6

```
       AGGAGAGAGCAAAGGGTGTCTGCGTCGTCACCAAATCGTAGCGTTTGTTACCAGAGGTTG
3721   ---------+---------+---------+---------+---------+---------+   3780

TGCACTGTTTACAGAATCTTCCTTTTATTCCTCACTCGGGTTTCTCTGTGGCTCCAGGCC
3781   ---------+---------+---------+---------+---------+---------+   3840

AAAGTGCCGGTGAGACCCATGGCTGTGTTGGTGTGGCCCATGGCTGTTGGTGGGACCCGT
3841   ---------+---------+---------+---------+---------+---------+   3900

GGCTGATGGTGTGGCCTGTGGCTGTCGGTGGGACTCGTGGCTGTCAATGGGACCTGTGGC
3901   ---------+---------+---------+---------+---------+---------+   3960

TGTCGGTGGGACCTACGGTGGTCGGTGGGACCCTGGTTATTGATGTGGCCCTGGCTGCCG
3961   ---------+---------+---------+---------+---------+---------+   4020

GCACGGCCCGTGGCTGTTGACGCACCTGTGGTTGTTAGTGGGGCCTGAGGTCATCGGCGT
4021   ---------+---------+---------+---------+---------+---------+   4080

GGCCCAAGGCCGGCAGGTCAACCTCGCGCTTGCTGGCCAGTCCACCCTGCCTGCCGTCTG
4081   ---------+---------+---------+---------+---------+---------+   4140

TGCTTCCTCCTGCCCAGAACGCCCGCTCCAGCGATCTCTCCACTGTGCTTTCAGAAGTGC
4141   ---------+---------+---------+---------+---------+---------+   4200

CCTTCCTGCTGCGAAGTTCTCCCATCCTGGGACGGCGGCAGTATTGAAGCTCGTGACAAG
4201   ---------+---------+---------+---------+---------+---------+   4260

TGCCTTCACACAGAACCCTCGGAACTGTCCACGCGTTCCGTGGGAACAAGGGGTT
4261   ---------+---------+---------+---------+------             4315
```

FIG. 1B-7

```
hjgl    1     MRSPRTRGRSGRPLSLLLALLCALRAKVCGASGQFELEILSMQNVNGELQNGNCCGGARN  60
rjg           ::::P::::P:::::::::::::::::::::::::::::::::::::::::::AEPGT hjgl   61     PGDR-KCTRDECDTYFKVCLKEYQSRVTAGGPCSFGSGSTPVIGGNTFNLKASRGNDRNR 120
rjg           LVRPY::::::::::::::::C::::::::::::::::::::::::::::::::::::::

hjgl  121     IVLPFSFAWPRSYTLLVEAWDSSNDTVQPDSIIEKASHSGMINPSRQWQTLKQNTGVAHF 180
rjg           ::::::::::::::::::::::::::G:::::I:::::::::::::::::::::::I:::

hjgl  181     EYQIRVTCDDYYYGFGCNKFCRPRDDFFGHYACDQNGNKTCMEGWMGPECNRAICRQGCS 240
rjg           ::::::::::H:::P:::::::::::::::::::::::::::::::::::::K:::::::

hjgl  241     PKHGSCKLPGDCRCQYGWQGLYCDKCIPHPGCVHGICNEPWQCLCETNWGGQLCDKDLNY 300
rjg           :::::::::::::::::::::::::::::::::T::::::::::::::::::::::::::

hjgl  301     CGTHQPCLNGGTCSNTGPDKYQCSCPEGYSGPNCEIAEHACLSDPCHNRGSCKETSLGFE 360
rjg           ::::::::::R:::::::::::::::::::::::::::::::::::::::::::S:::::

hjgl  361     CECSPGWTGPTCSTNIDDCSPNNCSHGGTCQDLVNGFKCVCPPQWTGKTCQLDANECEAK 420
rjg           ::::::::::::::::::::::::::::::::::::::::::::::::::::::::::::

hjgl  421     PCVNAKSCKNLIASYYCDCLPGWMGQNCDININDCLGQCQNDASCRDLVNGYRCICPPGY 480
rjg           :::::R:::V::::::::::::::::::::::::::::::::::::::::::::::::::

hjgl  481     AGDHCERDIDECASNPCLNGGHCQNEINRFQCLCPTGFSGNLCQLDIDYCEPNPCQNGAQ 540
rjg           ::::::::::::::::::::::::::::::::::::::::::::::::::::::::::::

hjgl  541     CYNRASDYFCKCPEDYEGKNCSHLKDHCRTTPCEVIDSCTVAMASNDTPEGVRYISSNVC 600
rjg           ::::::::::::::::::::::::::::::::::::::::::::::::::::::::::::

hjgl  601     GPHGKCKSQSGGKFTCDCNKGFTGTYCHENINDCESNPCRNGGTCIDVNSYKCICSDGW  660
rjg           ::::::::E:::::::::::::::::::::ECG:::T:::::::::::::::::::::::

hjgl  661     EGAYCETNINDCSQNPCHNGGTCRDLVNDFYCDCKNGWKGKTCHSRDSQCDEATCNNGGT 720
rjg           :::H::N:::::::::::Y:::::::::::::::::::::::::::::::::::::::::

hjgl  721     CYDEGDAFKCMCPGGWEGTTCNIARNSSCLPNPCHNGGTCVVNGESFTCVCKEGWEGPIC 780
rjg           ::::V:T::::::::::::::::::::::CP:::::::::D:::::::::::::::::::

hjgl  781     AQNTNDCSPHPCYNSGTCVDGDNWYRCECAPGFAGPDCRININECQSSPCAFGATCVDEI 840
rjg           T::::::::::::::Q::::::::::::::::::::::::::::::::::::::::::::

hjgl  841     NGYRCVCPPGHSGAKCQEVSGRP CITMGSVIPDGAKWDDDCNTCQCLNGRIACSKVWCGP 900
rjg           :::Q:I:::::::::::H::C:S:::::R::L:::::-:::::V:S::::::::::::::

hjgl  901     RPCLLHKGHSECPSGQSCIPILDDQCFVHPCTGVGECRSSSLQPVKTKCTSDSYYQDNCA 960
rjg           :::R:::::G:::N:::::V:::::::R:::A::::::::::::::::::::::::::::

hjgl  961     NITFTFNKEMMSPGLTTEHICSELRNLNILKNVSAEYSIYIACEPSPSANNEIHVAISAE 1020
rjg           :::::::::::::::::::::::::::::L::::::::::::::::::::::::::::::

hjgl 1021     DIRDDGNPIKEITDKIIDLVSKRDGNSSLIAAVAEVRVQRRPLKNRTDFLVPLLSSVLTV 1080
rjg           ::::::::V:::::::::::::::::::::::::::::::::::::::::::::::::::

hjgl 1081     AWICCLVTAFYWCLRK-RRKPGSHTHSASEDNTTNNVREQLNQIKNPIEKHGANTVPIKD 1140
rjg           ::V:::::::::V::R:::S:::::P:::::::::D::::::::::::::::::::::::

hjgl 1141     YENKNSKMSKIRTHNSEVEEDDMDKHQQKARFAKQPAYTLVDREEKPPNGTPTKHPNWTN 1200
rjg           ::::::::::::::::::::::::::V:::::V:::::::V:QR::::::::::::::::

hjgl 1201     KQDNRDLESAQSLNRMEYIV 1220
rjg           ::::::::::::::::::::
```

FIG. 2A

```
Jagged2         MRARGWGRLPRRLLLLVLCVQATRPMGYFELQLSALRNVNGELLSGACCDGDGRTTRAGGCGRDECDTYVRVCLKEYQAKVTPTGPCSYGYGA
Jagged1         MRSPRTRGRPGRPLSLLLALLCALRAKVCGASGQFELEILSMQNVNGELQNGNCC..GGARNPGDRKCTRDECDTYFKVCLKEYQSRVTAGGPCSFGSGS 95   TPVLGSNSFYLPPAGAAGDRARARSRTGGHQDPGLVVIPFQFAWPRSFTLIVEAWDWDNDTTPDEELLIERVSHAGMINPEDRWKSLHFSGHVAHLELQI
 99   TPVIGGNTFNL.KASRGNDRNR.........IVLPFSFAWPRSYTLLVEAWDSSNDTIQPDS.IIEKASHSGMINPSRQWQTLKQNTGIAHFEYQI
                                                                                                        2

195   RVRCDENYYSATCNKFCRPRNDFFGHYTCDQYGNKACMDGWMGKECKEAVCKQGCNLLHGGCTVPGECRCSYGWQGKFCDECVPYPGCVHGSCVEPWHCD
184   RVTCDDHYYGFGCNKFCRPRDFFGHYACDQNGNKTCMEGWMGPECNKAICRQGCSPKHGSCKLPDCRCQYGWQGLYCDKCIPHPGCVHGTCNEPWQCL
               3                                  4                                              5

295   CETNWGGLLCDKDLNYCGSHHPCVNGGTCINAEPDQYLCACPDGYLGKNCERAEHACASNPCANGGSCHEVLSGFECHCPSGWSGPTCALDIDECASNPC
284   CETNWGGQLCDKDLNYCGTHQPCLNRGTCSNTGPDKYQCSCPEGYSGPNCEIAEHACLSDPCHNRGSCKETSSGFECECSPGWTGPTCSTNIDDCSPNNC
                                                                              6                                7

395   AAGGTCVDQVDGFECICPEQWVGATCQLDANECEGKPCLNAFSCKNLIGGYYCDLPGWKGANCHININDCHGQCQHGGTCKDLVNGYQCVCPRGFGGRH
384   SHGGTCQDLVNGFKCVCPPQWTGKTCQLDANECEAKPCVNARSCKNLIASYYCDCLPGWMGQNCDININDCLGQCQNDASCRDLVNGYRCICPYGADH
          8                                       9                                        10

495   CELEYYKCASSPCRRGGICEDLVDGFRCHCPRGLSGPLCEVDVDLWCEPNPCLNGARCYNLEDDYYCACPEDFGGKNCSVPRETCPGGACRVIDGCFEA
484   CERDIDECASNPCLNGGHCQNEINRFQCLCPTGFSGNLCQLDID.YCEPNPCQNGAQCYNRASDYFCKCPEDYEGKNCSHLKDHCRTTPCEVIDSCTVAM
                                                                11                                        12

595   GSRAHGAA....PSGVCGPHGHCVSLPGGNFSCICDSGFTCGTYCHENIDDCMGQPCRNGGTCIDEVDSFACFCPSGWEGELCDINPNDCLPDPCHSRGRC
583   ASNDTPEGVRYISSNVCGPHGKCKSESGGKFTCDCNKGFTGTYCHENINDCEGNPCTNGGTCIDGVNSYKCICSDGWEGAHCENNINDCSQNPCHYGGTC
```

FIG. 2B-1

```
                    13                                                            14
 691  YDLVNDFYCVCDDGWKDKTCHSREFQCDAYTCSNGGTCYDSGDTFRCACPPGWKGSTCTIAKNSSCVPNPCVNGGTCVGSGDSFSCICRDGWEGRTCTHN
 683  RDLVNDFYCDCKNGWKGKTCHSRDSQCDEATCNNGGTCYDEVDTFKCMCPGGWEGTTCNIARNSSCLPNPCHNGGTCVVNGDSFTCVCKEGWEGPICTQN
                    15                                                            16
 791  TNDCNPLPCYNGGICVDGVNWFRCECAPGFAGPDCRINIDECQSSPCAYGATCVDEINGYRCSCPPGRSGPRCQEVVIFTRPCWSRGVSFPHGSSWEDC
 783  TNDCSPHPCYNSGTCVDGDNWYRCECAPGFAGPDCRININECQSSPCAFGATCVDEINGYQCICPPGHSGAKCHEVS..GRSCITMGRVILDGAKWDDDC
 891  NSCRCLDGHRDCSKVWCGWKPCLLSPQPSALSAQCPPGQQCREKAMGQCLQPPCENWGECTAEDPLPPSTPCLPRTTHLDNNCARLTLHFNRDQVPGTT
 881  NTCQCLNGRVACSKVWCGPRPCRLHKGH...GECPNGQSCIPVLDDQCFVRPCTGAGECRSSLQPVKTKC.TSDSYYQDNCANITFTFNKEMMSPGLT
 991  VGAICSGIRALPATRAAARDRLLLLCDRASSGASAVEVAVSFSPARDLPDSSLIQSTAHAIVAAITQR.GNSSLLLAVTEVKVETVVMGGSSTGLLVPV
 976  TEHICSELRNLNILKNVSAEYSIYIACEPSLSANNEIHVAISAEDIRD..DGNPVKEITDKIIDLVSKRDGNSSLIAAVAEVRVQRRPLKN.RTDFLVPL
1090  LCSVFSVLWLACMVICVWWTRKRRKERERSR...LPRDESANNQWAPLNPIRNPIERPGSSGLGTGGHKDVLYQCKNFTPPRRAGEALPGPASHGAGE
1073  LSSVLTVAWCCLVTAFYWCVRKRRRKPSSHTHSAPEDNTTNNVREQLNQIKNPIEKHGANTVPIKD....YENKNSKMSKIRTHNS..........
1187  DEEDEELSRGDGRLSRSREVPLTQIHQRPQLLPGKASLLAP..GPKVDNRAVRSTKDVRCAGRE  1248
1156  EVEEDDMDKHQQKVRFAKQPVYTLV.DREEKVPQRTPTKHPNWTNKQDNRDLESAQSLNRMEYIV  1219
```

FIG. 2B-2

Table 1 • The Exon/Intron Boundary Sequences of JAG1

| Exon Number | intron/EXON...EXON/intron | JAG1 cDNA (bp) | Exon Length(bp) |
|---|---|---|---|
| Exons 1,2 | not available | 801-852 | 52 |
| Exon 3 | gttcgtgcag/AGGTCCTACA(28)...GACACCGTTC/gtcagtatcg (29) | 853-1107 | 255 |
| Exon 4 | ttgtcttcag/AACCTGACAG(30)...TGTAACAGAG/gtatgtgtgt (31) | 1108-1168 | 61 |
| Exon 5 | tttttacag/CTATTGCCG(32)...GTGACTGCAG/g (33) | 1169-1299 | 131 |
| Exon 6 | gtgtctccag/GTGCCAGTAT(34)...TGTGACAAAG/gtatggccct (35) | 1300-1419 | 120 |
| Exon 7 | tttttggcag/ATCTCAATTA(36)...TGTGAAATTG/gtaagtggtc (37) | 1420-1533 | 114 |
| Exon 8 | gtttttgcag/CTGAGCAGC(38)...TGCTCTACAA/gtaagtccaa (39) | 1534-1647 | 114 |
| Exon 9 | tgttgaccag/ACATTGATGA(40)...TGCCAGTTAG/gtaagaacat (41) | 1648-1761 | 114 |
| Exon 10 | ctcctttcag/ATGCAAATGA(42)...TGTGACATAA/gtgagtgact (43) | 1762-1808 | 47 |
| Exon 11 | tattttttag/ATATTAATGA (44)...CTCCTGTCGG/gtatgtaaat (45) | 1809-1982 | 174 |
| Exon 12 | cctcttctag/GATTTGGTTA (46)...CCTCTGTCAG/gtgagtggtg (47) | 1983-2133 | 151 |
| Exon 13 | atatttgcag/CTGGACATCG (48)...CCCTGTGAAG/gtacctccct (49) | 2134-2298 | 165 |
| Exon 14 | tatctttctag/TGATTGACAG (50)...TGCCATGAAG/gtaagactcc (51) | 2299-2412 | 114 |
| Exon 15 | tgtttatag/ATATTAATGA (52)...TGTGAAACCA/aagagtgtgc (53) | 2413-2526 | 114 |
| Exon 16 | ttgattcttag/GTGACAGTCA (54)...GGCCACTCAC/gtaagtggta (55) | 2527-2640 | 114 |
| Exon 17 | ttttcctccag/CCCGAAACAG (56)...TGTAACATAG/gtaactttat (57) | 2641-2757 | 117 |
| Exon 18 | tctttatag/CCCGAAACAG (58)...TGTGCTCAGA/gtgagtgtcc (59) | 2758-2785 | 28 |
| Exon 19 | ttctttgcag/ATACCAATGA (60)...CTCATCCCTG/gtaagtgtga (61) | 2786-2871 | 86 |
| Exon 20 | gctttcttag/TTACAACAGC (62)...TGCAGAATAA/gtaaggactg (63) | 2872-2985 | 114 |
| Exon 21 | ttttcctag/ACATCAATGA (64)...TGCCAGGAAG/gtatgtgtgc (65) | 2986-3095 | 110 |
| Exon 22 | cacctgtcag/TTTCAGGGAG (66)...CTGCTCAAAG/gtaggacatg (67) | 3096-3329 | 234 |
| Exon 23 | ttttcctccag/GTCTGGTGTG (68)...GATGTCACCA/gtatgtaaca (69) | 3330-3461 | 132 |
| Exon 24 | atcgttttag/GGTCTTACTA(70)...TGTGGCCATT/gtaatgtataa (71) | 3462-3612 | 151 |
| Exon 25 | gtttttccag/TCTGCTGAAG (72)...AACAGAACAG/gtaggtgtca(73) | 3613-4404+ | 792+ |
| Exon 26 | tgccttacag/ATTTCCTTGT (74)... | | |

FIG. 6B

FIG. 7B AGS Family 1

FIG. 7C AGS Family 2

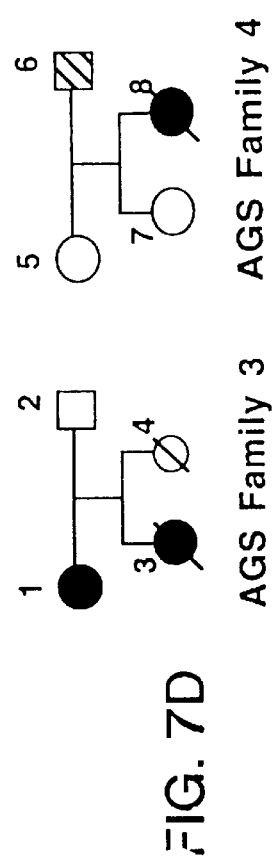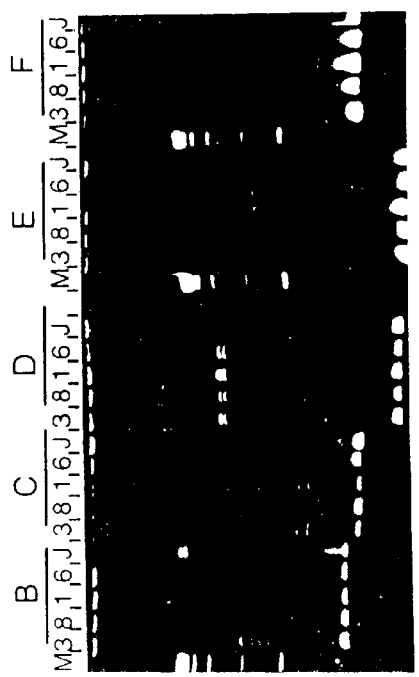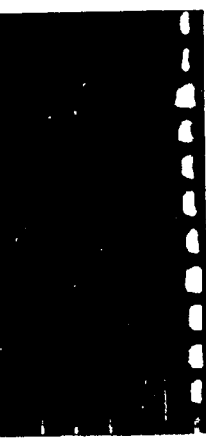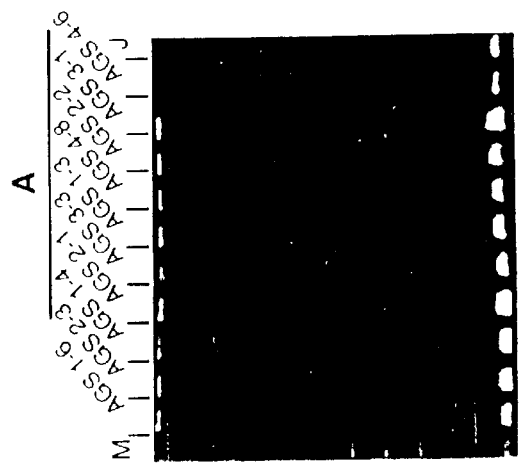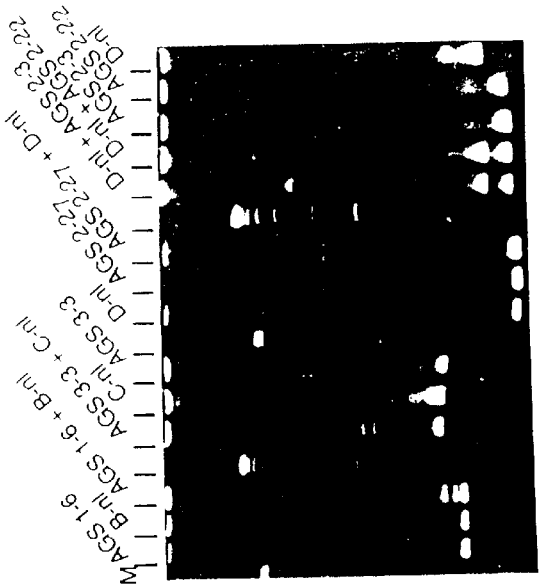
FIG. 7D
FIG. 7E
FIG. 7F

| Individuals | cDNA Mutations | EXONS/ Nucleotide Changes | Amino Acid Mutations | | Predicted Translation Products |
|---|---|---|---|---|---|
| AGS Family 1 | 1104delAG | Exon 4 del AG | Amino Acid Change After 230 | Normal: CN(230)RAICRQGCS<br>Mutant: CN(230)SYLPTRLQS* | 1 230 240(stop) |
| AGS Family 2 | 3102 ins5 | Exon 23 ins GTGGC | Amino Acid Change After 898 | Normal: WCG(898)PRPCL....<br>Mutant: WCG(898)VALDL.... | 1 898 945 (Stop) |
| AGS Family 3 | 2531 del4 | Exon 17 del CAGT | Amino Acid Change After 708 | Normal: DS(708)QCD....<br>Mutant: DS(708)VMR.... | 1 708 741 (Stop) |
| AGS Family 4 | 2066delC | Exon 13 del C | Amino Acid Change After 553 | Normal: FCKCP(553)ED....<br>Mutant: FCKCP(553)RT.... | 1 553 563 (Stop) |

FIG. 9

METHODS OF DIAGNOSING ALAGILLE SYNDROME

This application is a divisional of application Ser. No. 08/882,046, filed Jun. 25, 1997, now U.S. Pat. No. 6,136,952.

This invention was supported by grant numbers P30HD28834, P50HL54881, DK34431, DK51417, CA18221, HL36444, 1R01DK53104-01, DK02338-03 and 5P30HD288215 awarded by the National Institute of Health, USPHS Grant CA58207 and contract DE-AC-03-76SF00098 from the U.S. Department of Energy. The United States Government has certain rights in this invention.

BACKGROUND OF THE INVENTION

This invention relates to polypeptides and peptides for regulating stem cell differentiation and renewal and to the molecular defects involved in Alagille Syndrome.

Hematopoiesis involves a delicate balance between progenitor cell self-renewal and differentiation. Self-renewal generates additional progenitor cells through cell division, and differentiation produces specialized cell types such as red blood cells or lymphocytes. The ability to reliably reproduce hematopoietic differentiation and expansion in vitro would greatly facilitate the development of clinical therapeutic treatments based on blood products and cell transplantation. For example, the ability to modulate hematopoietic differentiation and expansion would promote the production of mature blood cells for transfusion therapies and the production of mature dendritic cells for immunotherapy. In addition, the ability to manipulate a hematopoietic cell population to maintain a large number of progenitor cells would greatly improve ex vivo retroviral gene therapy since cell proliferation is required for retroviral gene transduction.

The ability to maintain the survival and proliferation of hematopoietic progenitor cells and to inhibit their differentiation would also improve cell transplantation following tumor purging. In high-dose chemotherapy, doses of toxic drugs are escalated to destroy aggressive malignancies such as hematologic, breast, testicular and ovarian cancers. These high doses also destroy many of the rapidly cycling cells of the hematopoietic system, rendering a patient vulnerable to infection. The ability to promote the survival and expansion of a limited number of remaining hematopoietic progenitor cells would increase neutrophil and platelet recovery times and reduce the danger associated with tumor purging and hematopoietic cell transplantation. However, current technology cannot effectively regulate the balance of hematopoietic progenitor cell survival and differentiation.

During embryogenesis in Drosophila, the Notch receptor plays a central role in cell fate specification during development of the central and peripheral nervous systems, eye, mesoderm, wing, bristles and ovaries. The Notch family of cell-cell signaling receptors is highly conserved in fly, worm, frog as well as higher vertebrates, and functions to determine cell fate through the transduction of signals between cells in direct contact with each other.

In higher vertebrates, the process of cell-fate determination is integral to hematopoiesis, where the balance between stem cell or progenitor cell self-renewal and differentiation is carefully regulated. Notch homologues can play a role in determining cell fate in hematopoietic cells, as evidenced by the expression of Notch1 RNA in immature hematopoietic precursor cells from adult human bone marrow. Notch homologues are implicated in T lymphocyte development since the human Notch homologue, TAN-1 (hNotch1), was isolated from a T-cell leukemia containing a translocation between Notch and the T cell receptor (TCR)-β gene. In addition, Notch1 can influence the CD4/CD8 cell-fate decision. Because an activated form of Notch1 can inhibit G-CSF-induced granulocytic differentiation of 32D myeloid progenitors, Notch also can play a role in mediating cell-fate decisions in the myeloid lineage.

The evolutionary conservation of Notch is reflected in the corresponding conservation of Notch ligands. Several Notch ligands have been identified thus far, including Delta and Serrate in Drosophila; LAG-2 and APX-1 in *C. elegans*; X-Delta-1 in Xenopus; C-Delta-1 and C-Serrate-1 in the chick; Delta-like-1 (Dll1) in the mouse; and Jagged1 and Jagged2 in the rat. Each of these Notch ligands share two important extracellular features: the DSL domain, defined by a conserved region among Delta Serrate, and LAG-2, and tandem epidermal growth factor (EGF) repeats. Delta and Serrate have been shown to interact with Notch in Drosophila, and fibroblasts expressing rat Jagged1 inhibit muscle cell differentiation of Notch1-expressing C2C12 cells. These results indicate that DSL family polypeptides including Drosophila Delta and Serrate and rat Jagged can function as Notch ligands.

However, a human Notch ligand, which would be useful in manipulating the balance of hematopoietic progenitor cell renewal and differentiation, has not yet been identified. Thus, there is a need for a human Notch ligand and for methods of using the ligand to maintain and expand hematopoietic progenitor cells to make clinical blood products and progenitor cells for transplantation. The present invention satisfies this need by providing human JAGGED1 polypeptides and provides related advantages as well.

The invention also relates to Alagille Syndrome, which is an autosomal dominant, developmental disorder affecting the liver, heart, skeleton, eye, face and kidneys. The course and prognosis of Alagille Syndrome, which occurs at a minimum estimated frequency of 1 in 70,000 live births, varies widely. This multi-system disorder traditionally has been defined by a paucity of intrahepatic bile ducts in association with several of the main clinical abnormalities, which are cholestasis, cardiac disease, skeletal abnormalities, ocular abnormalities and a characteristic facial phenotype. Fifteen percent of Alagille Syndrome patients will require liver transplantation, and seven to ten percent of patients will have severe congenital heart disease.

Unfortunately, the available therapies for Alagille Syndrome are few, and both diagnosis and treatment have been hampered by a lack of knowledge regarding the molecular defect underlying the disease. In a relatively small number of patients, gross chromosomal deletions of chromosome 20 appear to be inherited with the disorder. However, for the large majority of patients lacking such gross chromosomal abnormalities, the genetic defect responsible for Alagille Syndrome has eluded discovery. Identification of the molecular defect responsible for Alagille Syndrome would be useful in the early diagnosis and prenatal testing of individuals at risk for the disorder. In addition, knowledge of mutations resulting in Alagille Syndrome would facilitate the development of new therapies for treating the disorder. Thus, there is a need for identifying the mutations responsible for Alagille Syndrome and for methods of diagnosing the disorder by analyzing the genetic defect responsible for the disorder. The present invention satisfies this need and also provides related advantages.

SUMMARY OF THE INVENTION

The present invention provides an isolated polypeptide exhibiting substantially the same amino acid sequence as JAGGED, or an active fragment thereof, provided that the polypeptide does not have the amino acid sequence of SEQ ID NO:5 or SEQ ID NO:6. The invention further provides an isolated nucleic acid molecule containing a nucleotide sequence encoding substantially the same amino acid sequence as JAGGED, or an active fragment thereof, provided that the nucleotide sequence does not encode the amino acid sequence of SEQ ID NO:5 or SEQ ID NO:6. Also provided herein is a method of inhibiting differentiation of hematopoietic progenitor cells by contacting the progenitor cells with an isolated JAGGED polypeptide, or active fragment thereof. The invention additionally provides a method of diagnosing Alagille Syndrome in an individual. The method consists of detecting an Alagille Syndrome disease-associated mutation linked to a JAGGED locus.

BRIEF DESCRIPTION OF THE DRAWINGS

FIG. 2. (A) Alignment of hJAGGED1 (hJg1) and rjagged1 (rJg) amino acid sequences. The peptide signal sequence (residues 1 to 21), EGF-like repeats (residues 234 to 862), and transmembrane domain (residues 1077 to 1091) are shown in bold type. The DSL domain (residues 185 to 239) and the cysteine-rich region (residues 863 to 1012) are underlined. (B) Alignment of rat Jagged1 amino acid sequence SEQ ID NO:5 and rat Jagged2 amino acid sequence SEQ ID NO:6.

FIG. 9. Summary of the mutations identified in Alagille Syndrome individuals and the corresponding predicted translation products. For each of four Alagille Syndrome mutations, the position of the, mutation within the hJAGGED1 cDNA and gene are provided, as well as the predicted amino acid mutations and size of the truncated hJAGGED1 polypeptide.

DETAILED DESCRIPTION OF THE INVENTION

The present invention is directed to the discovery of human Notch ligands, designated JAGGED. The polypeptides of the invention are transmembrane proteins that share several structural features with other Notch ligands, including a DSL (Delta/Serrate/Lag-2) domain characteristic of these ligands and tandem epidermal growth factor (EGF)-like repeats. Provided herein are exemplary JAGGED polypeptides, human JAGGED1 (hJAGGED1) and human JAGGED2 (hJAGGED2). hJAGGED1 is expressed in bone marrow stromal cells, and a stromal cell line expressing hJAGGED1 permits survival and proliferation of hematopoietic progenitor cells expressing Notch but inhibits granulocytic differentiation. As disclosed herein, a JAGGED-derived peptide can mimic the function of an intact JAGGED molecule by inhibiting the differentiation of Notch-expressing progenitor cells (Example II). Thus, the JAGGED polypeptides and peptides of the invention can be used, for example, in ex vivo therapy for inhibiting differentiation and maintaining the proliferative potential of progenitor cells such as hematopoietic stem cells.

Thus, the present invention provides an isolated JAGGED polypeptide. An isolated JAGGED polypeptide of the invention can have substantially the same amino acid sequence as the hJAGGED1 sequence SEQ ID NO:2 shown in FIG. 1A or substantially the same amino acid sequence as the hJAGGED2 sequence SEQ ID NO:4 shown in FIG. 1B, provided that the polypeptide does not have the amino acid sequence of SEQ ID NO:5 or SEQ ID NO:6.

Figure 1C:
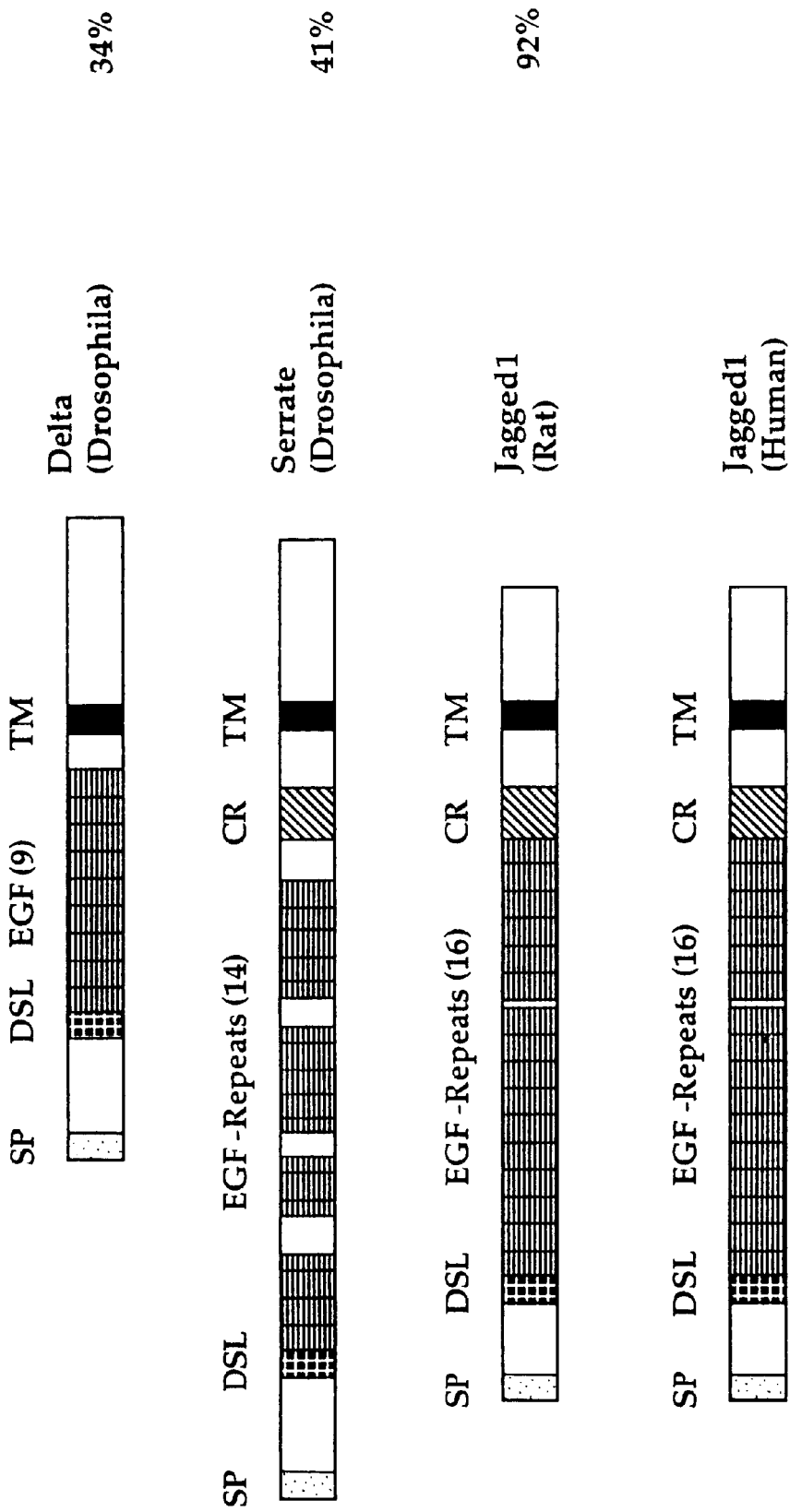
FIG. 1. (A) Nucleotide sequence SEQ ID NO:1 and amino acid sequence SEQ ID NO:2 of the human JAGGED1 (hJAGGED1) cDNA. (B) Partial nucleotide sequence SEQ ID NO:3 and amino acid sequence SEQ ID NO:4 of the human Jagged 2 (hJAGGED2) cDNA. (C) Diagram showing the protein structure of hJAGGED1 in alignment with the Drosophila Delta, Drosophila Serrate and rat Jagged1 proteins. The signal peptide region is indicated SP. DSL is a domain unique to Notch ligands, shared by Drosophila Delta and Serrate and the C. elegans protein LAG-2. Also indicated are the epidermal growth factor-like repeats (EGF-like repeats); cysteine-rich region (CR) and transmembrane domain (TM). The percent amino acid identity to hJAGGED1 is shown at the right.

As used herein, the term "JAGGED" means a JAGGED polypeptide and includes polypeptides having substantially the same amino acid sequence as the hJAGGED1 polypeptide (SEQ ID NO:2) shown in FIG. 1A or the hJAGGED2 polypeptide (SEQ ID NO:4) shown in FIG. 1B, provided that the polypeptide does not have the amino acid sequence of SEQ ID NO:5 or SEQ ID NO:6. hJAGGED1 exhibits an apparent molecular weight of about 150 kDa on SDS-PAGE and is a 1219 amino acid polypeptide having the sequence shown in FIG. 1A. As illustrated in FIG. 1C, hJAGGED1 is a membrane-bound ligand with a large extracellular domain and a very short intracellular domain. The hJAGGED1 polypeptide shares structural features with the Drosophila polypeptides Delta and Serrate and with the rat Jagged1 polypeptide (see FIG. 1C). In particular, hJAGGED1 has a DSL domain, which is a region conserved among the Notch ligands Delta, Serrate and LAG-2. In addition, the extracellular domain of hJAGGED1 contains EGF repeats. A cysteine-rich domain is also present in hJAGGED1, as in Serrate and rat Jagged1. The DSL and EGF-repeat domains can be involved in interaction with the Notch receptor (Henderson et al., *Devel.* 120:2913–2924 (1994); Lieber et al., *Neuron* 9:847–859 (1992); and Rebay et al., *Cell* 67:687–699 (1991), each of which are incorporated herein by reference).

hJAGGED2 is a polypeptide of more than 1150 amino acids and includes the amino acid sequence shown in FIG. 1B. Like hJAGGED1, hJAGGED2 is a membrane-bound ligand with a large extracellular domain and a relatively short intracellular domain. The hJAGGED2 polypeptide also has a DSL domain, 15 EGF-like repeats and a transmembrane domain characteristic of membrane-bound Notch ligands.

As disclosed in Example I, hJAGGED1 is widely expressed in a variety of human tissues. However, in bone marrow, hJAGGED1 expression is restricted to a subpopulation of stromal cells. hJAGGED1 is also expressed in the HS-27a cell line, which is a line of spindle-shaped human stromal cells that do not support differentiation of hematopoietic progenitor cells but support the maintenance of immature progenitors for five to eight weeks. The expression of hJAGGED1 in these cells is consistent with a role for JAGGED polypeptides in regulating hematopoietic progenitor cell survival and differentiation.

Co-culture of myeloid progenitor 32D cells expressing full-length Notch with HS-27a cells, which express hJAGGED1, inhibits G-CSF induced granulocytic differentiation of the 32D cells (see Example II). As disclosed herein, a peptide corresponding to part of the hJAGGED1 DSL domain (residues 188 to 204; SEQ ID NO:9) also inhibits differentiation of Notch-expressing 32D cells in the presence of G-CSF. Thus, the present invention provides JAGGED polypeptides and peptides useful for maintaining the proliferative potential and inhibiting differentiation of progenitor cells such as hematopoietic progenitor cells.

The term JAGGED encompasses a polypeptide having the sequence of the naturally occurring hJAGGED1 polypeptide (SEQ ID NO:2) or the sequence of the naturally occurring hJAGGED2 polypeptide (SEQ ID NO:4) and is intended to include related polypeptides having substantial amino acid sequence similarity to hJAGGED1 (SEQ ID NO:2) or hJAGGED2 (SEQ ID NO:4), provided that the polypeptide does not have the amino acid sequence of SEQ ID NO:5 or SEQ ID NO:6. Such related polypeptides exhibit greater sequence similarity to hJAGGED1 or hJAGGED2 than to other DSL-containing polypeptides or EGF-repeat containing polypeptides and include alternatively spliced forms of hJAGGED1 or hJAGGED2 and isotype variants of the amino acid sequences shown in FIGS. 1A and 1B, provided that the polypeptides do not have the amino acid sequence of SEQ ID NO:5 or SEQ ID NO:6. The hJAGGED1 and hJAGGED2 polypeptides disclosed herein have about 54% identity to each other at the amino acid level. As used herein, the term JAGGED describes polypeptides generally having an amino acid sequence with greater than about 50% identity, preferably greater than about 60% identity, more preferably greater than about 70% identity, and can be a polypeptide having greater than about 80%, 90%, 95%, 97%, or 99% amino acid sequence identity with hJAGGED1 (SEQ ID NO:2) or hJAGGED2 (SEQ ID NO:4), provided that the polypeptide does not have the amino acid sequence of SEQ ID NO:5 or SEQ ID NO:6.

A JAGGED polypeptide can be more closely related to hJAGGED1, for example, than to hJAGGED2. Thus, a JAGGED polypeptide can be a member of the JAGGED1 subfamily or a member of the JAGGED2 subfamily. A member of the JAGGED1 subfamily is a polypeptide having substantially the same amino acid sequence as hJAGGED1 (SEQ ID NO:2), or an active fragment thereof, provided that the polypeptide does not have the amino acid sequence of SEQ ID NO:5. A member of the JAGGED1 subfamily generally has an amino acid sequence with greater than about 50% identity, preferably greater than about 60% identity, more preferably greater than about 70% identity, and can be a polypeptide having greater than about 80%, 90%, 95%, 97%, or 99% amino acid identity with hJAGGED1 (SEQ ID NO:2), provided that the polypeptide does not have the amino acid sequence of SEQ ID NO:5.

Similarly, a member of the JAGGED2 subfamily is a polypeptide having substantially the same amino acid sequence as hJAGGED2 (SEQ ID NO:4), or an active fragment thereof, provided that the polypeptide does not have the amino acid sequence of SEQ ID NO:6. A member of the JAGGED2 subfamily generally has an amino acid sequence with greater than about 50% identity, preferably greater than about 60% identity, more preferably greater than about 70% identity, and can be a polypeptide having greater than about 80%, 90%, 95%, 97%, or 99% amino acid identity with hJAGGED2 (SEQ ID NO:4), provided that the polypeptide does not have the amino acid sequence of SEQ ID NO:6.

As used herein, the term "substantially the same amino acid sequence," when used in reference to a JAGGED amino acid sequence, is intended to mean the sequence shown in FIG. 1A or FIG. 1B, or a similar, non-identical sequence that is considered by those skilled in the art to be a functionally equivalent amino acid sequence, provided that the amino acid sequence is not the amino acid sequence of SEQ ID NO:5 or SEQ ID NO:6. For example, an amino acid sequence that has substantially the same amino acid sequence as JAGGED can have one or more modifications such as amino acid additions, deletions or substitutions relative to the amino acid sequence of hJAGGED1 (SEQ ID NO:2) or hJAGGED2 (SEQ ID NO:4), provided that the modified polypeptide retains substantially at least one biological activity of hJAGGED1 or hJAGGED2, such as substantially the ability to bind and activate a Notch receptor or substantially the ability to inhibit progenitor cell differentiation, provided that the modified polypeptide does not have the amino acid sequence of SEQ ID NO:5 or SEQ ID NO:6. Comparison of sequences for substantial similarity can be performed between two sequences of any length and usually is performed with nucleotide sequences of between 5 and 3500 nucleotides, preferably between about 10 and 300 nucleotides and more preferably between about 15 and 50 nucleotides. Comparison for substantial similarity between amino acid sequences is usually performed with sequences between about 6 and 1200 residues, preferably between about 10 and 100 residues and more preferably between about 25 and 35 residues. Such comparisons for substantial similarity are performed using methodology routine in the art.

Therefore, it is understood that limited modifications can be made without destroying the biological function of a JAGGED polypeptide and that only a portion of the entire primary sequence can be required in order to effect activity. For example, minor modifications of hJAGGED1 (SEQ ID NO:2) or hJAGGED2 (SEQ ID NO:4) that do not destroy polypeptide activity also fall within the definition of JAGGED and within the definition of the polypeptide claimed as such, provided that such modifications do not produce a polypeptide having the amino acid sequence of SEQ ID NO:5 or SEQ ID NO:6. Also, for example, genetically engineered fragments of JAGGED either alone or fused to heterologous proteins such as fragments or fusion proteins that retain measurable activity in binding and activating Notch or a Notch homologue, in inhibiting progenitor cell differentiation, or other inherent biological activity of JAGGED fall within the definition of the polypeptide claimed as such.

It is understood that minor modifications of primary amino acid sequence can result in polypeptides which have substantially equivalent or enhanced function as compared to the hJAGGED1 sequence set forth in FIG. 1A or the hJAGGED2 sequence set forth in FIG. 1B. These modifications can be deliberate, as through site-directed mutagenesis, or can be accidental such as through mutation in hosts harboring a JAGGED encoding nucleic acid. All such modified polypeptides are included in the definition of a JAGGED polypeptide as long as at least one biological function of JAGGED is retained, provided that the polypeptide does not have the amino acid sequence of SEQ ID NO:5 or SEQ ID NO:6. Further, various molecules can be attached to a JAGGED polypeptide including, for example, other polypeptides, carbohydrates, lipids, or chemical moieties. Such modifications are included within the definition of a JAGGED polypeptide.

Several Notch ligands have been identified including ligands from Drosophila, C. elegans, Xenopus, mouse and rat. Known Notch ligands include Delta and Serrate in Drosophila (Baker et al., Science 250:1370–1377 (1990); Cuoso et al., Cell 67:311–323 (1994)); LAG-2 and APX-1 in C. elegans (Mello et al., Cell 77:95–106 (1994); Tax et al., Nature 368:150–154 (1994); Henderson et al., Develop. 120:2913–2924 (1994)); X-Delta-1 in Xenopus (Chitnis et al., Nature 375:761–766 (1995)); C-Delta-1 (Henrique et al., 1995) and C-Serrate-1 in the chick (Myat et al., Dev. Biol. 174:233–247 (1996); Delta-like-1 (Dll1) in the mouse (Bettenhausen et al., Devel. 121:2407–2418 (1995)); and Jagged1 and Jagged2 in the rat (Lindsell et al., Cell 80:909–917 (1995); Shawber et al., Dev. Biol. 370–376 (1996)). However, these Notch ligands are not JAGGED polypeptides as defined herein. The rat Jagged1 polypeptide (SEQ ID NO:5) and rat Jagged2 polypeptide (SEQ ID NO:6) are explicitly excluded from the definition of a JAGGED polypeptide as defined herein. Other Notch ligands described above, which may share the ability to activate Notch or a Notch homologue, lack substantial amino acid sequence similarity with hJAGGED1 (SEQ ID NO:2) or hJAGGED2 (SEQ ID NO:4) and, thus, are not JAGGED polypeptides as defined herein.

In one embodiment, the invention provides an isolated JAGGED polypeptide including substantially the same amino acid sequence as JAGGED, or an active fragment thereof, provided that said polypeptide does not have the amino acid sequence of SEQ ID NO:5, the amino acid sequence of SEQ ID NO:6, the amino acid sequence designated by GenBank accession number U61276, the amino acid sequence designated by GenBank accession number U77720, or the amino acid sequence designated by GenBank accession number U77914.

The present invention also provides active fragments of a JAGGED polypeptide. As used herein, the term "active fragment" means a polypeptide fragment having substantially the same amino acid sequence as a portion of a JAGGED polypeptide, provided that the JAGGED fragment retains at least one biological activity of JAGGED. An active fragment can have, for example, substantially the same amino acid sequence as a portion of hJAGGED1 (SEQ ID NO:2) or substantially the same amino acid sequence as a portion of hJAGGED2 (SEQ ID NO:4). A biological activity of JAGGED can be, for example, the ability to bind and activate Notch or a Notch homologue, the ability to inhibit differentiation of a hematopoietic progenitor cell or the ability to maintain or increase the proliferative potential of a hematopoietic progenitor cell. Examples of active fragments are provided herein as SEQ ID NO:7, which is a soluble active fragment of hJAGGED1 containing residues 1 to 1010, and SEQ ID NO:8, which is a soluble active fragment of hJAGGED1 containing residues 178 to 240. As disclosed in Example II, these soluble JAGGED fragments have activity in inhibiting granulocytic differentiation of primary mouse hematopoietic cells or in increasing their proliferative potential. Explicitly excluded from the definition of an active fragment are polypeptide portions of SEQ ID NO:5 and SEQ ID NO:6.

The term "isolated," as used herein in reference to a polypeptide, peptide or nucleic acid molecule of the invention, means a polypeptide, peptide or nucleic acid molecule that is in a form that is relatively free from contaminating lipids, polypeptides, nucleic acids or other cellular material normally associated with the polypeptide, peptide or nucleic acid molecule in a cell.

A modified JAGGED polypeptide, or fragment thereof, can be assayed for activity using one of the assays described in Example II or using another assay for measuring progenitor cell differentiation or the maintenance of proliferative potential known in the art. For example, a retroviral expression vector containing a nucleic acid molecule encoding a modified hJAGGED1 or hJAGGED2 polypeptide, or fragment thereof, can be introduced into HS-23 cells, and the transduced cells assayed for the ability to inhibit differentiation of progenitor cells, such as 32D myeloid progenitor cells expressing full-length Notch, in the presence of a differentiating agent such as G-CSF. A soluble JAGGED polypeptide or fragment thereof can be assayed, for example, by introducing an expression vector containing a nucleic acid molecule encoding the soluble JAGGED polypeptide or fragment into a cell and subsequently assaying the culture supernatant for the ability to inhibit hematopoietic progenitor cell differentiation as described in Example II.

The nucleic acid to be assayed can encode an amino acid sequence corresponding to a portion of native hJAGGED1 (SEQ ID NO:2) or native hJAGGED2 (SEQ ID NO:4) or can be modified to encode one or more amino acid substitutions, deletions or insertions, provided that the nucleic acid molecule does not encode the amino acid sequence of SEQ ID NO:5 or SEQ ID NO:6. One or more point mutations can be introduced into the nucleic acid encoding the modified JAGGED polypeptide or fragment to be assayed using, for example, site-directed mutagenesis (see Wu (Ed.), *Meth. In Enzymol.* Vol. 217, San Diego: Academic Press (1993); Chapter 22 of Innis et al. (Ed.), *PCR Protocols*, San Diego: Academic Press, Inc. (1990), each of which is incorporated herein by reference). Such mutagenesis can be used to introduce a specific, desired amino acid substitution, deletion or insertion; alternatively, a nucleic acid sequence can be synthesized having random nucleotides at one or more predetermined positions to generate random amino acid substitutions. Scanning mutagenesis also can be useful in generating nucleic acid molecules encoding JAGGED polypeptides or fragments that are modified throughout the entire polypeptide or fragment sequence. Such modified fragments can be screened for the ability to inhibit Notch-expressing 32D cell differentiation as described in Example II; for the ability to increase the self-renewal capacity of hematopoietic progenitor cells (Example II); or using another assay for measuring progenitor cell differentiation or the maintenance of progenitor cell proliferative potential that is known in the art.

If desired, a pool of modified JAGGED polypeptides or JAGGED fragments can be assayed for activity en masse. For example, to identify an active fragment of hJAGGED1 or hJAGGED2, pools of synthetic JAGGED fragments or pools of cell supernatants can be assayed for the ability to inhibit the differentiation of 32D cells expressing Notch; subsequently, pools of fragments or supernatants with activity can be subdivided, and the assay repeated in order to isolate the active modified hJAGGED1 or hJAGGED2 polypeptide or fragment from the active pool.

An isolated JAGGED polypeptide, or active fragment thereof, can be obtained by a variety of methods known within the art, including biochemical, recombinant and chemical synthesis methods. Biochemical methods for isolating a JAGGED polypeptide, or active fragment thereof, include preparative gel electrophoresis, gel filtration, affinity chromatography, ion exchange and reversed phase chromatography, chromatofocusing, isoelectric focusing and sucrose or glycerol density gradients (see, for example, Chapter 38 of Deutscher, *Methods in Enzymology: Guide to Protein Purification*, Vol. 182, Academic Press, Inc., San Diego (1990) and Chapter 8 of Balch et al., *Methods in Enzymology*, Vol. 257, Academic Press, Inc., San Diego (1995), each of which is incorporated herein by reference in its entirety). For example, as disclosed herein in Example I, hJAGGED1 RNA is expressed in a variety of human tissues, including stomach, thyroid, spinal cord, lymph node, trachea, adrenal gland, and bone marrow, and in the human bone marrow stromal cell line HS-27a (Roecklein and Torok-Storb, *Blood* 85:997–1005 (1995), which is incorporated herein by reference). From these results, one skilled in the art knows that one of these tissues or the HS-27a cell line can be used as a source of material for isolating a hJAGGED1 polypeptide.

Preparative gel electrophoresis can be useful in preparing an isolated JAGGED polypeptide or active fragment of the invention. For example, a JAGGED polypeptide, or active fragment thereof, can be isolated by preparative polyacrylamide gel electrophoresis and elution of the polypeptide or fragment by diffusion or electroelution (see, for example, Chapter 33 of Deutscher, supra, 1990). Continuous elution gel electrophoresis using a system such as the Model 491 Prep Cell (BioRad, Hercules, Calif.) can be used to purify a JAGGED polypeptide, or active fragment thereof. If desired, continuous elution gel electrophoresis can be combined with further purification steps such as liquid phase preparative isoelectric focusing using, for example, the Rotofor system (BioRad).

Affinity chromatography is particularly useful in preparing an isolated JAGGED polypeptide or active fragment of the invention. A polypeptide that interacts with a JAGGED polypeptide, for example, a Notch polypeptide, can be useful as an affinity matrix for isolating a JAGGED polypeptide or active fragment of the invention. One skilled in the art understands that polypeptide fragments such as fragments of Notch also can be useful affinity matrices for isolating a JAGGED polypeptide or active fragment of the invention.

Immunoaffinity chromatography can be particularly useful in isolating a JAGGED polypeptide or active fragment thereof. For example, immunoprecipitation or column chromatography with an antibody that selectively binds JAGGED can be used to isolate a JAGGED polypeptide or active fragment thereof. An anti-JAGGED monoclonal or polyclonal antibody that selectively binds JAGGED can be prepared using an immunogen such as the sequence shown as SEQ ID NO:2, or a synthetic peptide fragment thereof, as described further below. One skilled in the art understands that a particularly useful immunogen can be a synthetic peptide fragment of SEQ ID NO:2 or SEQ ID NO:4 having a sequence that is relatively unique to JAGGED. Thus, in selecting an immunogen, one can exclude, if desired, regions of SEQ ID NO:2 or SEQ ID NO:4 which are conserved among other proteins. Methods of affinity chromatography are well known in the art and are described, for example, in Chapters 29, 30 and 38 of Deutscher, supra, 1990, which has been incorporated herein by reference.

Recombinant methods for producing a polypeptide through expression of a nucleic acid sequence in a suitable host cell also are well known in the art and are described, for example, in Sambrook et al., Molecular Cloning: A Laboratory Manual, 2nd Ed, Vols 1 to 3, Cold Spring Harbor Laboratory Press, New York (1989), which is incorporated herein by reference. Nucleic acids for expression of a JAGGED polypeptide are provided herein as SEQ ID NO:1 and SEQ ID NO:3. The production of recombinant hJAGGED1 polypeptide is illustrated in Example II.

A recombinant JAGGED polypeptide or active fragment of the invention can be expressed as a fusion protein with a heterologous "tag" for convenient isolation from bacterial or mammalian host proteins. For example, histidine-tagged recombinant JAGGED can be isolated by nickel-chelate chromatography. Similarly, a glutathione-S-transferase tag or an antigenic tag such as "FLAG," "AU" or a myc epitope tag also can be included in a recombinant JAGGED polypeptide or active fragment of the invention (Sambrook et al., supra, 1989). The use of the PinPoint™ expression system for expression of the hJAGGED1 active fragment SEQ ID NO:8 as a fusion protein with a heterologous biotinylated peptide is illustrated in Example II.

A JAGGED polypeptide fragment or a JAGGED peptide of the invention can be produced by chemical synthesis, for example, by the solid phase peptide synthesis method of Merrifield et al., *J. Am. Chem. Soc.* 85:2149 (1964), which is incorporated herein by reference. Standard solution methods well known in the art also can be used to synthesize a peptide or polypeptide fragment useful in the invention (see, for example, Bodanszky, *Principles of Peptide Synthesis*, Springer-Verlag, Berlin (1984) and Bodanszky, *Peptide Chemistry*, Springer-Verlag, Berlin (1993), each of which is incorporated herein by reference). A newly synthesized peptide or polypeptide fragment can be purified, for example, by high performance liquid chromatography (HPLC) and can be characterized using mass spectrometry or amino acid sequence analysis.

A JAGGED polypeptide of the invention is useful for preparing an antibody that selectively binds a JAGGED polypeptide such as hJAGGED1 (SEQ ID NO:2) or hJAGGED2 (SEQ ID NO:4). An antibody that selectively binds a JAGGED polypeptide can be useful, for example, in purifying a JAGGED polypeptide by immunoaffinity chromatography. Such an antibody also can be useful in diagnosing Alagille Syndrome in an individual by detecting reduced expression of a JAGGED polypeptide or by detecting an abnormal JAGGED gene product such as a truncated hJAGGED1 gene product. A particularly useful diagnostic antibody can be, for example, an antibody that selectively binds a C-terminal epitope of hJAGGED1, such that the amount of full-length hJAGGED1 polypeptide in a sample can be analyzed.

As used herein, the term antibody is used in its broadest sense to include polyclonal and monoclonal antibodies, as well as polypeptide fragments of antibodies that retain selective binding activity for a JAGGED polypeptide of at least about $1 \times 10^5$ M$^{-1}$. One skilled in the art would know that anti-JAGGED antibody fragments such as Fab, F(ab')$_2$ and Fv fragments can retain selective binding activity for a JAGGED polypeptide and, thus, are included within the definition of an antibody. In addition, the term antibody as used herein includes naturally occurring antibodies as well as non-naturally occurring antibodies and fragments that have binding activity such as chimeric antibodies or humanized antibodies. Such non-naturally occurring antibodies can be constructed using solid phase peptide synthesis or produced recombinantly. Such non-naturally occurring antibodies also can be obtained, for example, by screening combinatorial libraries consisting of variable heavy chains and variable light chains as described by Borrebaeck (Ed.), *Antibody Engineering* (Second edition) New York: Oxford University Press (1995), which is incorporated herein by reference.

An antibody selective for a polypeptide, or that selectively binds a polypeptide, binds with substantially higher affinity to that polypeptide than to an unrelated polypeptide. An antibody selective for a polypeptide also can be selective for a related polypeptide. For example, an antibody selective for human JAGGED1 (SEQ ID NO:2) also can be selective for hJAGGED2 (SEQ ID NO:4) or for JAGGED1 homologs from other species.

An anti-JAGGED antibody can be prepared, for example, using a JAGGED fusion protein or a synthetic peptide encoding a portion of JAGGED such as hJAGGED1 (SEQ ID NO:2) or hJAGGED2 (SEQ ID NO:4) as an immunogen. One skilled in the art would know that a purified JAGGED polypeptide, which can be prepared from natural sources or produced recombinantly as described above, or fragments of JAGGED, including a peptide portion of JAGGED such as a synthetic peptide, can be used as an immunogen. Non-immunogenic fragments or synthetic peptides of JAGGED can be made immunogenic by coupling the hapten to a carrier molecule such as bovine serum albumin (BSA) or keyhole limpet hemocyanin (KLH). In addition, various other carrier molecules and methods for coupling a hapten to a carrier molecule are well known in the art and described, for example, by Harlow and Lane, *Antibodies: A Laboratory Manual* (Cold Spring Harbor Laboratory Press, 1988), which is incorporated herein by reference.

The present invention also provides an isolated nucleic acid molecule that contains a nucleotide sequence encoding substantially the same amino acid sequence as JAGGED, or an active fragment thereof, provided that the nucleic acid molecule does not encode the amino acid sequence of SEQ ID NO:5 or SEQ ID NO:6. An isolated nucleic acid molecule of the invention can have a nucleotide sequence encoding the same amino acid sequence as hJAGGED1 (SEQ ID NO:2) or hJAGGED2 (SEQ ID NO:4) or can encode an amino acid sequence with substantial similarity to SEQ ID NO:2 or SEQ ID NO:4, provided that the nucleic acid molecule does not encode the amino acid sequence of SEQ ID NO:5 or SEQ ID NO:6. An isolated nucleic acid molecule of the invention can have, for example, a nucleotide sequence encoding the amino acid sequence of SEQ ID NO:2 or SEQ ID NO:4. Such isolated nucleic acid molecules are exemplified herein as SEQ ID NO:1 and SEQ ID NO:3.

In one embodiment, the invention provides an isolated nucleic acid molecule that contains a nucleotide sequence encoding substantially the same amino acid sequence as JAGGED, or an active fragment thereof, provided that nucleic acid sequence does not encode the amino acid sequence of SEQ ID NO:5, the amino acid sequence of SEQ ID NO:6, the amino acid sequence designated by GenBank accession number U61276, the amino acid sequence designated by GenBank accession number U77720, or the amino acid sequence designated by GenBank accession number U77914.

As used herein, the term "isolated nucleic acid molecule" means a nucleic acid molecule that is in a form that is relatively free from contaminating lipids, polypeptides, unrelated nucleic acids and other cellular material normally associated with a nucleic acid molecule in a cell.

An isolated nucleic acid molecule of the invention can be, for example, a nucleic acid molecule encoding an alternatively spliced JAGGED variant, a polymorphic variant, a nucleic acid molecule that is related, but different, and encodes the same JAGGED polypeptide due to the degeneracy of the genetic code, or a nucleic acid molecule that is related, but different and encodes a different JAGGED polypeptide that exhibits at least one biological activity of JAGGED, provided that the nucleic acid molecule does not encode the amino acid sequence of SEQ ID NO:5 or SEQ ID NO:6.

The present invention also provides a cell containing a recombinant nucleic acid molecule having a nucleotide sequence encoding substantially the same amino acid as JAGGED, or active fragment thereof, provided that the nucleotide sequence does not encode the amino acid sequence of SEQ ID NO:5 or SEQ ID NO:6. The encoded JAGGED polypeptide can be, for example, hJAGGED1 (SEQ ID NO:2) or hJAGGED2 (SEQ ID NO:4), or an active fragment thereof, including soluble active fragments and membrane-bound active fragments. The cell can be a prokaryotic cell or a eukaryotic cell such as an HS-23 human stromal cell, COS cell or BHK cell.

An HS-23 cell can be particularly useful for expressing a recombinant nucleic acid molecule encoding a membrane-bound form of a JAGGED polypeptide. HS-23 cells can be transduced with retroviral vectors to express membrane-bound JAGGED variants and can be used as a stromal cell layer for maintaining hematopoietic progenitor cells and inhibiting their differentiation. As described in Example II, a COS or BHK cell can be particularly useful for expressing a recombinant nucleic acid molecule encoding a soluble form of JAGGED, such as an active fragment having hJAGGED1 amino acids 1 to 1010 (SEQ ID NO:7) or an active fragment having hJAGGED1 amino acids 178 to 240 (SEQ ID NO:8). The supernatant from such a COS or BHK cell has the activity of the soluble active JAGGED fragment and can be used in crude form to inhibit the differentiation of hematopoietic progenitor cells or as a source for purifying the soluble active JAGGED fragment.

The present invention also provides an isolated JAGGED peptide having at most about 40 amino acids and including substantially the same amino acid sequence as SEQ ID NO:9. A JAGGED peptide of the invention can be, for example, a peptide of up to about forty amino acids including the amino acid sequence SEQ ID NO:9, or a substantially similar sequence. A JAGGED peptide can have, for example, about 20, 25, 30, 35 or 40 amino acids including the amino acid sequence of SEQ ID NO:9 or a substantially similar sequence. Provided herein is an example of an isolated JAGGED peptide, which has the amino acid sequence Cys-Asp-Asp-Tyr-Tyr-Tyr-Gly-Phe-Gly-Cys-Asn-Lys-Phe-Cys-Arg-Pro-Arg (SEQ ID NO:9).

Figure 4:
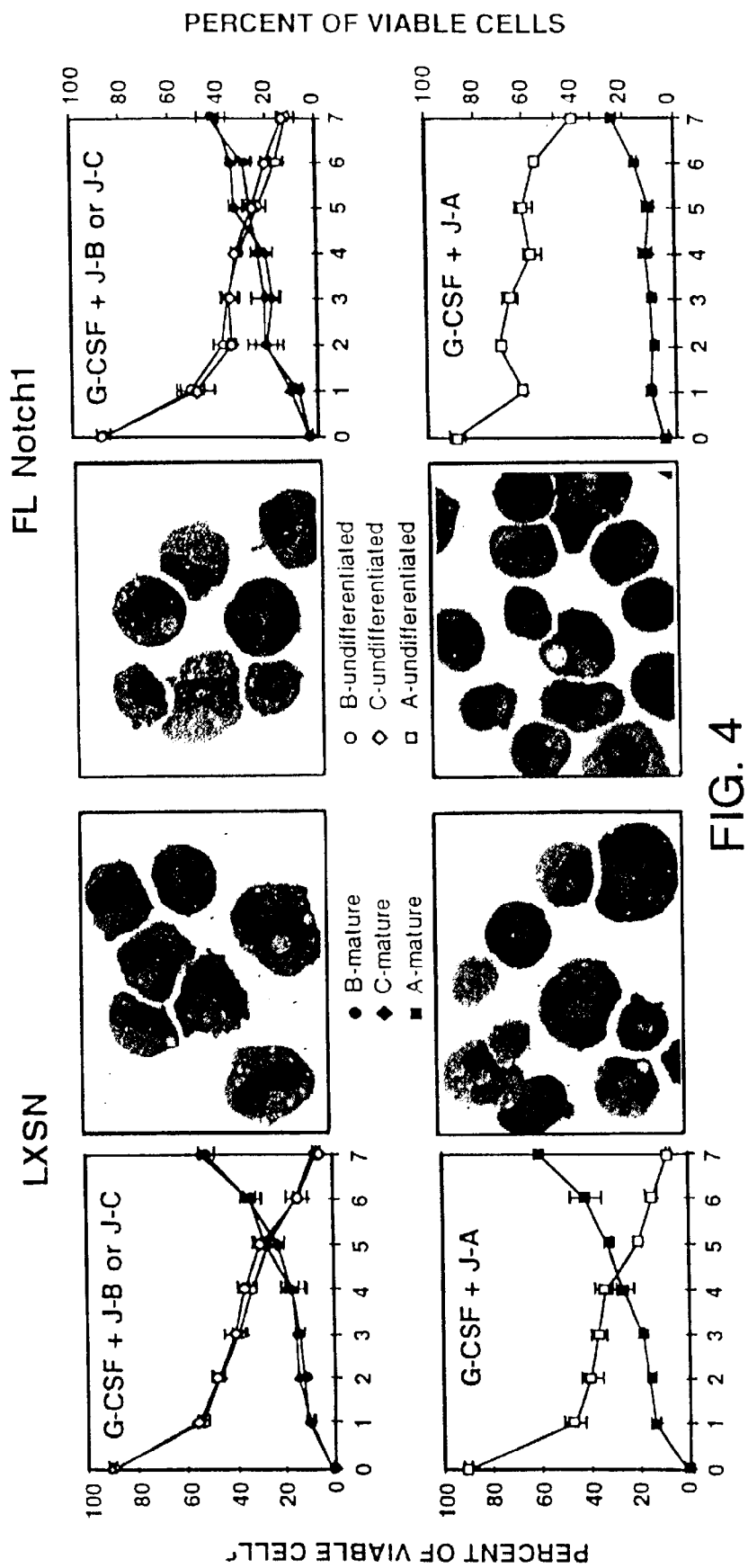
FIG. 4. Inhibition of granulocytic differentiation by a soluble peptide corresponding to part of the hJAGGED1 DSL domain. 32D clones carrying the control LXSN retroviral vector alone or the vector containing FL Notch1 were evaluated for differentiation in the presence of G-CSF and different peptides corresponding to distinct portions of hJAGGED1. Peptide SEQ ID NO:9 ("J-A") corresponds to a portion of the extracellular DSL domain. Peptide SEQ ID NO:10 ("J-B") corresponds to EGF-repeat 1, and peptide SEQ ID NO:11 ("J-C") corresponds to the intracellular domain. Shown is an experiment using 10 μM peptide. Each plot represents the average and SEM of three independent clones. The center panels show representative Wright stained cells (clones LXSN-10 and FL N 2.4) after 6 days in culture with G-CSF and peptide SEQ ID NO:10 (J-B; top panel) or peptide SEQ ID NO:9 (J-A; lower panel).

The JAGGED peptide SEQ ID NO:9 has the amino acid sequence of residues 188 to 204 of hJAGGED1, which corresponds to a portion of the conserved DSL domain. As disclosed herein, this 17-mer peptide SEQ ID NO:9 can mimic the function of hJAGGED1 in promoting survival and inhibiting differentiation of Notch-expressing myeloid progenitor cells in the presence of a differentiating stimulus. FIG. 4 shows that differentiation of 32D clones expressing Notch1 was unaffected by treatment with peptide SEQ ID NO:10 ("J-B") or SEQ ID NO:11 ("J-C"). However, differentiation was significantly inhibited in the presence of the JAGGED peptide SEQ ID NO:9 ("J-A") as shown in the lower right panel of FIG. 4. This inhibition was similar to that observed when Notch-expressing 32D cells were cultured with hJAGGED1-expressing HS-27a stromal cells. Thus, a JAGGED peptide of the invention has activity in inhibiting the differentiation of progenitor cells and can be useful, for example, in the in vitro expansion of a variety of hematopoietic progenitor cell types.

The present invention therefore provides methods of using the JAGGED polypeptides and peptides of the invention. The present invention provides a method of inhibiting differentiation of hematopoietic progenitor cells by contacting the hematopoietic progenitor cells with an isolated JAGGED polypeptide having substantially the same amino acid sequence as JAGGED, or an active fragment thereof. An isolated JAGGED polypeptide useful in the methods of the invention can have substantially the same amino acid sequence as hJAGGED1 (SEQ ID NO:2) or hJAGGED2 (SEQ ID NO:4) or can be an active fragment.

The invention also provides a method of inhibiting differentiation of progenitor cells by contacting the progenitor cells with an isolated JAGGED peptide having at most about forty amino acids and including substantially the same amino acid sequence as SEQ ID NO:9. Such progenitor cells can be hematopoietic progenitor cells and can be contacted, for example, in vitro. Such an isolated JAGGED peptide of the invention can be, for example, a peptide of up to about forty amino acids which includes the amino acid sequence SEQ ID NO:9 or a substantially similar sequence. For example, an isolated JAGGED peptide useful in the methods of the invention can be a peptide having the sequence Cys-Asp-Asp-Tyr-Tyr-Tyr-Gly-Phe-Gly-Cys-Asn-Lys-Phe-Cys-Arg-Pro-Arg (SEQ ID NO:9).

As used herein, the term "progenitor cell" means any cell capable of both self-renewal and differentiation. Thus, a progenitor cell can proliferate under appropriate conditions to produce an increased number of progenitor cells, or can differentiate under appropriate conditions to produce cells of specialized function. A progenitor cell can be a committed or unipotent progenitor cell that differentiates into one particular differentiated cell type. A progenitor cell also can be a pluripotent progenitor cell that has the potential to differentiate into multiple different cell types. A progenitor cell can be, for example, a hematopoietic progenitor cell, a neuronal precursor cell, a muscle progenitor cell, a hepatic progenitor cell or another cell capable of both self-renewal and differentiation. One skilled in the art understands that a progenitor cell useful in the invention expresses a JAGGED receptor, which can be, for example, a Notch polypeptide.

The term "hematopoietic progenitor cell," as used herein, means a progenitor cell capable of differentiating to one or more red or white blood cell types. A hematopoietic progenitor cell can be, for example, a totipotent hematopoietic stem cell capable of both self-renewing and differentiating to all hematopoietic cell types, thereby producing erythrocytes, granulocytes, monocytes, mast cells, lymphocytes and megakaryocytes. A hematopoietic progenitor cell also can be, for example, a lymphoid progenitor or myeloid progenitor cell. A lymphoid progenitor cell generates T and B progenitor lymphocytes. A myeloid progenitor cell generates progenitor cells for erythrocytes, neutrophils, eosinophils, basophils, monocytes, mast cells and platelets. In nature, bone marrow stromal cells produce the membrane-bound and diffusible factors responsible for maintaining an appropriate balance between hematopoietic progenitor cell proliferation and differentiation.

The present invention provides methods of maintaining progenitor cells in an undifferentiated state by contacting progenitor cells with a JAGGED polypeptide, or active fragment thereof. The progenitor cells can be cells capable of reconstituting the hematopoietic system such as hematopoietic stem cells. In one embodiment, the progenitor cells are maintained in a totipotent state capable of differentiating into all the specialized cell types of the hematopoietic system.

Subsequent to treating progenitor cells according to a method of the invention, the progenitor cells can be subject to cryopreservation, for example, by freezing in liquid nitrogen and can be stored, if desired, for a period of months, years or decades and later thawed for further expansion or differentiation. Thus, progenitor cells can be obtained from a newborn, for example, "locked" into an undifferentiated state using a JAGGED polypeptide according to a method of the invention, and stored for future use for an indefinite period.

The methods of the invention also represent advances in cell transplantation and gene therapy. In one embodiment, progenitor cells maintained in an undifferentiated state according to the methods of the invention can be subsequently transplanted into an individual, such that the progenitor cells differentiate fully in the individual. The progenitor cells can be, for example, totipotent hematopoietic stem cells, which differentiate fully in the individual to reconstitute the hematopoietic system.

The methods of the invention therefore have utility in cell transplantation, including bone marrow transplantation, peripheral blood stem cell transplantation and umbilical cord blood transplantation (McAdams et al., *Trends in Biotech.* 14:341–349 (1996), which is incorporated herein by reference). The cell transplantation methods of the invention can be useful, for example, in replacing the hematopoietic stem cells of a cancer patient having a leukemia or lymphoma such as acute myelogeous leukemia (AML), non-Hodgkin's lymphoma or chronic myelogenous leukemia.

The progenitor cells can be, for example, autologous or allogeneic to the individual into which the transplanted cells are introduced. When the progenitor cells are derived from a cancer patient, the progenitor cells can be obtained by purging bone marrow or peripheral blood with, for example, chemical agents, immunomagnetic beads, antisense oligonucleotides or antibodies. If desired, progenitor cells can be sorted prior to treating with a JAGGED polypeptide, or active fragment thereof, according to a method of the invention. For example, progenitor cells can be sorted to obtain $CD34^+$ stem cells, which are contacted with a JAGGED polypeptide or active fragment thereof to maintain the $CD34^+$ stem cells in an undifferentiated state capable of full differentiation, and subsequently transplanted into an individual such that the $CD34^+$ stem cells differentiate fully and reconstitute the entire hematopoietic system of the individual.

The methods of the invention also have gene therapy applications. A nucleic acid molecule encoding a gene product can be introduced into progenitor cells maintained in an undifferentiated state according to a method of the invention. Gene therapy methods for introducing a nucleic acid molecule into a cell such as a progenitor cell are well known in the art and include retroviral and adenoviral methods as well as liposome-mediated and other gene transfer technologies as described in Chang (Ed), *Somatic Gene Therapy* Boca Raton, CRC Press, Inc. (1995), which is incorporated herein by reference. The methods of the invention, involving the use of a JAGGED polypeptide or JAGGED peptide for maintaining progenitor cells in an undifferentiated state, are particularly useful when combined with retroviral gene transfer methods, which require that cells be in a proliferating state.

The invention also provides a method of maintaining progenitor cells in an undifferentiated state by contacting the progenitor cells with a JAGGED peptide having at most about 40 amino acids and containing. substantially the same amino acid sequence as SEQ ID NO:9. In the methods of the invention, the progenitor cells can be capable of reconstituting the hematopoietic system. The progenitor cells can be maintained in a totipotent state and can be, for example, maintained in culture.

The invention further provides a method of maintaining progenitor cells in an undifferentiated state by contacting the progenitor cells with a JAGGED peptide having at most about 40 amino acids and containing substantially the same amino acid sequence as SEQ ID NO:9 and cryopreserving the progenitor cells maintained in an undifferentiated state. In addition, the invention provides a method of maintaining progenitor cells in an undifferentiated state by contacting the progenitor cells with a JAGGED peptide having at most about 40 amino acids and containing substantially the same amino acid sequence as SEQ ID NO:9 and introducing a nucleic acid molecule encoding a gene product into the progenitor cells.

The JAGGED polypeptides, active fragments and JAGGED peptides of the invention can be administered in a variety of dosage regimes to modulate the inhibitory effect on undifferentiated hematopoietic progenitor cells. For example, a JAGGED polypeptide, active fragment or JAGGED peptide can be administered in a single bolus of an effective concentration, or alternatively, multiple treatments of a JAGGED polypeptide, active fragment or JAGGED peptide can be administered to, for example, modulate or enhance the inhibitory effect on hematopoietic progenitor cells. Similarly, the amount of a JAGGED polypeptide, active fragment or JAGGED peptide that is administered can be increased or decreased so as to modulate the inhibitory effect on hematopoietic progenitor cell differentiation. A JAGGED polypeptide, active fragment or JAGGED peptide also can be administered in combination with other compounds which can modulate hematopoietic cell differentiation or can modulate other therapeutic events. Such procedures are known to those skilled in the art.

The inhibition of hematopoietic progenitor cell differentiation also can be modulated by altering the activity of a JAGGED polypeptide receptor. Activity can be altered by, for example, increasing the amount or expression level of a JAGGED polypeptide or by modulating the activation of a JAGGED receptor. Other methods exist as well and are known or can be determined by those skilled in the art.

As disclosed herein, molecular defects in hJAGGED1 can cause Alagille Syndrome, which is an autosomal dominant, developmental disorder that affects structures in the liver, heart, skeleton, eye, face, kidney and other organs. The minimal estimated frequency of the syndrome is 1 in 70,000 live births. The syndrome traditionally has been defined by a paucity of intrahepatic bile ducts in association with several of the main clinical abnormalities: cholestasis, cardiac disease, skeletal abnormalities, ocular abnormalities and a characteristic facial phenotype. Cholestasis occurs as a consequence of the paucity of bile ducts. Cardiac anomalies most commonly involve the peripheral and main pulmonary arteries as well as the pulmonary valves. The most common skeletal anomalies are "butterfly" or hemivertebrae, resulting from clefting abnormalities of the vertebral bodies. Ocular lesions include anterior chamber defects, most commonly posterior embryotoxon, which is a benign defect, and retinal pigmentary abnormalities. Facies have been described as triangular, consisting of a prominent forehead, deep-set eyes, hypertelorism, long straight nose with flattened tip, short philtrum, flat midface and a triangular chin. Renal and neurodevelopmental abnormalities occur less frequently. Fifteen percent of patients will require liver transplantation and seven to ten percent of patients have severe congenital heart disease, most often tetralogy of Fallot (Walker et al. (Eds), *Gastrointestinal Disease: Pathophysiology, Diagnosis, Management* (3rd edition) B.C. Decker, Inc., Philadelphia pp 1124–1140 (1991), which is incorporated herein by reference). An Alagille Syndrome diagnosis is made if bile duct paucity is accompanied by three of the five main clinical criteria. The expressivity of Alagille Syndrome is variable; accordingly, family members of a proband are considered affected if they express any of the five main clinical features.

The genetic defect underlying this multi-system disorder has been mapped to a 1.5 Mb segment based on analysis of overlapping chromosomal deletions at 20p11-12. Identified herein is the gene responsible for the Alagille Syndrome disorder, the human Notch ligand, hJAGGED1. Four distinct coding region mutations in the AhJAGGED1 gene were identified and shown to segregate with disease phenotype in four Alagille Syndrome families. As disclosed in Example V and summarized in FIG. 9, all four mutations lie within conserved regions of the hJAGGED1 gene: within the DSL domain, the EGF-repeats and the cysteine-rich region. Each of these mutations are predicted to produce a translational frameshift resulting in a gross alteration of the hJAGGED1 gene product. Furthermore, none of the mutations observed in Alagille Syndrome families were present in 100 normal control chromosomes studied. Thus, from the hundreds of potential genes within the cytogenetic deletion 20p11-12, the hJAGGED1 gene product has been identified as responsible for Alagille Syndrome. Based on this identification, the present invention provides methods of diagnosing Alagille Syndrome in a individual. Such methods can be useful in the early diagnosis or prenatal testing of individuals at risk for the disorder and can facilitate the development of therapies for affected individuals.

The present invention provides a method of diagnosing Alagille Syndrome in an individual by detecting a disease-associated mutation linked to a JAGGED locus. The disease-associated mutation can be linked but outside a JAGGED gene or can be within a JAGGED gene, for example, in a JAGGED coding sequence, 5' or 3' regulatory region, or within an intronic sequence.

In one embodiment of the invention, the JAGGED locus is a human JAGGED1 (hJAGGED1) locus. In the methods of the invention, the disease-associated mutation can produce, for example, an inactive hJAGGED1 gene product such as a truncated hJAGGED1 gene product. Examples of Alagille Syndrome disease-associated mutations occurring within the hJAGGED1 nucleotide sequence SEQ ID NO:1 are provided herein and include nucleotide variations at nucleotides 1104–1105, nucleotide 3102, nucleotides 2531–2534 and nucleotide 2066 of SEQ ID NO:1.

As used herein, the term "linked" means that two genetic loci have a tendency to be inherited together as a result of their proximity. If two genetic loci are linked and are polymorphic, one locus can serve as a marker for the inheritance of the second locus. Thus, an Alagille Syndrome disease-associated mutation linked to a JAGGED locus having a modified JAGGED allele causing Alagille Syndrome can serve as a marker for inheritance of the modified JAGGED allele. Such a linked mutation can be located in proximity to a JAGGED gene or can be located within a JAGGED gene.

The term "JAGGED locus," as used herein, means a locus encoding a JAGGED gene product. A JAGGED locus can be, for example, the human JAGGED1 locus, positioned within markers D20S894 and D20S507, as described in Example III.

The term "Alagille Syndrome disease-associated mutation," as used herein, is synonymous with "disease-associated mutation" and means a molecular variation of at most several thousand nucleotides that tends to be inherited together with the Alagille Syndrome disorder.

Disclosed herein are a variety of Alagille Syndrome disease-associated mutations linked to the hJAGGED1 locus. Distinct disease-associated mutations, which occur within the hJAGGED1 coding sequence, were found in each of four Alagille Syndrome families as summarized in FIG. 9. In a first Alagille Syndrome family, a deletion of "AG" at positions 1104–1105 of SEQ ID NO:1 produced a protein truncated at amino acid 240. In a second family, an insertion of five nucleotides ("GTGGC") at position 3102 of SEQ ID NO:1 produced a protein truncated at amino acid 945, while in a third family, a deletion of "CAGT" at positions 2531–2534 of SEQ ID NO:1 resulted in a protein truncated at amino acid 741. In a fourth Alagille Syndrome family, a single "C" nticleotide deletion at position 2066 of SEQ ID NO:1 resulted in a protein truncated at amino acid 563.

A disease-associated mutation useful in diagnosing Alagille Syndrome can be, for example, a nucleotide substitution, insertion or deletion of one or more nucleotides that tends to be inherited together with Alagille Syndrome. For example, the molecular variation can be a nucleotide substitution, insertion or deletion of about 1 to 3000 nucleotides, such as a substitution, insertion or deletion of about 1 to 1000 nucleotides, about 1 to 100 nucleotides, about 1 to 50 nucleotides or about 1 to 10 nucleotides. Disclosed herein are a two nucleotide deletion, five nucleotide insertion, four nucleotide deletion and single nucleotide deletion, which are mutations associated with Alagille Syndrome (Example V). One skilled in the art understands that a disease-associated mutation also can be a molecular variation such as abnormal methylation or other modification that does not produce a difference in the primary nucleotide sequence of the disease-associated allele as compared to the normal allele. Specifically excluded from the definition of an Alagille Syndrome disease-associated mutation are large nucleotide variations of more than several thousand nucleotides, including gross cytogenetic deletions and megabase deletions such as those reported in Rand et al., *Am. J. Hum. Genet.* 57:1068–1073 (1995), which is incorporated herein by reference.

An Alagille Syndrome disease-associated mutation can occur within a JAGGED gene and can result, for example, in production of an inactive JAGGED gene product or a reduced amount of a JAGGED gene product. For example, an Alagille Syndrome disease-associated mutation within a JAGGED gene can be a nucleotide modification within a gene regulatory element such that a JAGGED gene product is not produced or a nucleotide modification within an intronic sequence resulting in an abnormally spliced, inactive JAGGED gene product. In addition, an Alagille Syndrome disease-associated polymorphism can be a nucleotide modification resulting in one or more amino acid substitutions, deletions or insertions in a JAGGED coding sequence, which result in an inactive JAGGED gene product. For example, an inactive JAGGED gene product can result from a frameshift or nonsense mutation producing a truncated JAGGED gene product, a missense mutation, or a gross nucleotide insertion or deletion. Such an inactive JAGGED gene product can be, for example, a JAGGED polypeptide variant lacking the ability to activate Notch or a soluble JAGGED polypeptide that functions as a dominant negative molecule when expressed with wild type JAGGED polypeptide or another JAGGED polypeptide variant lacking one or more biological functions of JAGGED.

A variety of molecular methods useful in detecting an Alagille Syndrome disease-associated mutation linked to a JAGGED locus are well known in the art. For example, allele-specific oligonucleotide hybridization involves the use of a labeled oligonucleotide probe having a sequence perfectly complementary, for example, to a disease-associated sequence. Under appropriate conditions, the allele-specific probe hybridizes to a nucleic acid containing the disease-associated mutation but does not hybridize to the corresponding wild type nucleic acid sequence having one or more nucleotide mismatches. If desired, a second allele-specific oligonucleotide probe that matches the wild type sequence also can be used. Similarly, the technique of allele-specific oligonucleotide amplification can be used to selectively amplify, for example, a disease-associated polymorphic sequence by using an allele-specific oligonucleotide primer that is perfectly complementary to the nucleotide sequence of a disease-associated allele but which has one or more mismatches as compared to the corresponding wild type sequence (Mullis et al. (Eds.), *The Polymerase Chain Reaction*, Birkhauser, Boston, (1994), which is incorporated herein by reference). Particularly useful allele-specific oligonucleotides are oligonucleotides that correspond to about 15 to about 40 nucleotides of the hJAGGED1 nucleotide sequence SEQ ID NO:1 and that include one of the disease-associated polymorphic regions identified herein: nucleotides 1104–1105, nucleotide 3102, nucleotides 2531–2534 or nucleotide 2066 of SEQ ID NO:1. One skilled in the art understands that the one or more nucleotide mismatches that distinguish between the disease-associated and wild type allele are preferably located in the center of an allele-specific oligonucleotide primer to be used in allele-specific oligonucleotide hybridization. In contrast, an allele-specific oligonucleotide primer to be used in PCR amplification preferably contains the one or more nucleotide mismatches that distinguish between the disease-associated and wild type alleles at the 3' end of the primer.

A heteroduplex mobility assay (HMA) is another well known assay that can be used to diagnose Alagille Syndrome according to a method of the invention. HMA is useful for detecting the presence of a polymorphic sequence since a DNA duplex carrying a mismatch, such as a heteroduplex between a wild type and mutated DNA fragment, has reduced mobility in a polyacrylamide gel compared to the mobility of a perfectly base-paired duplex (Delwart et al., *Science* 262:1257–1261 (1993); White et al., *Genomics* 12:301–306 (1992), each of which is incorporated herein by reference). Methods for detecting an Alagille Syndrome disease-associated mutation using a heteroduplex mobility assay are set forth in Example V.

The technique of single strand conformation polymorphism (SSCP) also can be used to detect the presence of an Alagille Syndrome disease-associated mutation (see Hayashi, *PCR Methods Applic.* 1:34–38 (1991), which is incorporated herein by reference). This technique can be used to detect mutations based on differences in the secondary structure of single-strand DNA that produce an altered electrophoretic mobility upon non-denaturing gel electrophoresis. Polymorphic fragments are detected by comparison of the electrophoretic pattern of the test fragment to the corresponding fragment from a normal individual of a non-Alagille Syndrome family. The detection of an Alagille Syndrome disease-associated mutation using SSCP is exemplified in Example V.

Denaturing gradient gel electrophoresis (DGGE) also can be used to detect an Alagille Syndrome disease-associated mutation linked to a JAGGED locus. In DGGE, double-stranded DNA is electrophoresed in a gel containing an increasing concentration of denaturant; double-stranded fragments made up of mismatched wild type and disease-associated sequences have segments that melt more rapidly, causing such fragments to migrate differently as compared to perfectly complementary sequences obtained from normal individuals (Sheffield et al., "Identifying DNA Polymorphisms by Denaturing Gradient Gel Electrophoresis" in Innis et al., supra, 20 1990).

Other well-known approaches for analyzing a mutation include automated sequencing, RNAase mismatch techniques (Winter et al., *Proc. Natl. Acad. Sci.* 82:7575–7579 (1985), which is incorporated herein by reference) and the use of restriction fragment length polymorphisms (see Innis et al., supra, 1990). For families in which the disease-associated mutation has been defined, automated sequencing of the region of interest can be particularly useful in diagnosing Alagille Syndrome. Thus, the methods of the invention for diagnosing Alagille Syndrome in an individual can be practiced using a heteroduplex mobility assay or single strand conformation polymorphism assay as illustrated in Example V, using one of the well known assays described above, or another art-recognized assay for detecting a disease-associated mutation.

The following examples are intended to illustrate but not limit the present invention.

EXAMPLE I

Isolation and Characterization of Human JAGGED1

This example describes the isolation, characterization and expression of human JAGGED1.

Isolation of the Human JAGGED1 CDNA

A cDNA encoding a human Notch ligand expressed in the bone marrow microenvironment was isolated by amplifying human bone marrow cDNA with degenerate primers SEQ ID NO:12 and SEQ ID NO:13, which correspond to portions of the conserved DSL and EGF-like repeat domains of rat Jagged1 (rjagged; Lindsell et al., supra, 1995). Ten PCR products of potential interest were identified, cloned and sequenced. The clone Sdi-06 contains a 327 bp insert that encodes part of the DSL and EGF-repeat domains. The sequence of this fragment has 96% predicted amino acid sequence identity with the corresponding region of rjagged1 (residues 205 to 312), 84% predicted amino acid sequence identity with C-Serrate-1 (residues 178–286), and 52% predicted amino acid sequence identity with C-Delta-1 (residues 203–311). Thus, the Sdi-06 clone encodes a partial cDNA fragment of the human homolog of rjagged1.

The complete hJAGGED1 cDNA was obtained by screening a human bone marrow cDNA library with $^{32}$P-labeled Sdi-06. One of the cDNA clones isolated, D-01, was found to contain the 5'-end of human JAGGED1 including 417 bp of 5' untranslated sequence and 2270 bp of coding sequence. The 3' end of hJAGGED1 was obtained by rescreening the same human bone marrow cDNA library with $^{32}$P-labeled rat Jagged1 CDNA provided by Dr. Weinmaster (Lindsell et al., supra, 1995). A cDNA clone identified with this probe, designated Y-A01, contains 2.4 kb of coding region and 1.5 kb of 3' untranslated region. A full-length 5.5 kb hJAGGED1 cDNA was assembled from the 5' D-01 clone and the 3' Y-A01 clone as described further below.

The full-length hJAGGED1 clone has an open reading frame of 3657 base pairs and encodes a predicted protein product of 1219 amino acids (FIG. 1A). Analysis of the amino acid sequence indicates that hJAGGED1 is a transmembrane protein with a large extracellular domain and a very short intracellular domain. The hJAGGED1 protein shares structural features with the Drosophila Notch ligands Delta and Serrate and with rat Jagged1. The shared structural features include a DSL motif and 16 epidermal growth factor-like (EGF-like) repeats within the extracellular domain. A cysteine-rich region present in Serrate and rJagged1 is also conserved in hJAGGED1 (FIG. 1C).

An alignment of the amino acid sequences of hJAGGED1 (hjg) and rJagged1 (rjg) is shown in FIG. 2A. The hJAGGED1 protein has 94% overall amino acid identity with rJagged1, with 96% amino acid identity with the highly conserved DSL and EGF-repeat domains. Several distinctive amino acid substitutions are present in the hJAGGED1 sequence relative to rJagged1. Two prolines in the signal peptide region of rJagged1 are replaced with arginine and serine in hJAGGED1 (residues five and ten, respectively). In addition, the region between the signal peptide and the DSL motif is dissimilar (compare residues 56 to 64 in hJAGGED1 (GGARNPGDR; SEQ ID NO:14) to residues 56 to 65 in rJagged1 (AEPGTLVRPY; SEQ ID NO:15). Other amino acid differences include a proline to phenylalanine substitution within the DSL motif (residue 194 of hJAGGED1); amino acid differences within the EGF-repeat region; and a serine to cysteine substitution within the cysteine-rich domain, (residue 860 of hJAGGED1). In the intracellular domain, a proline to serine substitution occurs at residue 1107 of hJAGGED1, and a valine to proline substitution occurs at residue 1187 of hJAGGED1.

Human bone marrow poly(A) RNA was obtained from Clontech Laboratories, Inc. (Palo Alto, Calif.) and reverse transcribed with random primer using the SuperScript Preamplication system (catalogue number 18089–011 from Gibco BRL (Gaithersburg, Md.) following the manufacturer's procedure. First strand cDNA was subsequently amplified by PCR using degenerate primers SEQ ID NO:12 and SEQ ID NO:13, which correspond to peptide sequences DDFFGHY (residues 205–211; SEQ ID NO:16) and PCHYGGTCRDLVND (residues 676–689; SEQ ID NO:17), respectively. The sequence of SEQ ID NO:12 is 5'-GAYGAYTTYTTYGGNCAYTA-3', and the sequence of SEQ ID NO:13 is 5'-RCANGTNCCNCCRTARTGRCANGG-3', where R indicates G/C, Y indicates T/A, and N indicates G/C/T/A. PCR reactions were performed using Taq polymerase (Perkin Elmer, Foster City, Calif.) under the following conditions: 92° C., 30 seconds; 50° C., 30 seconds; and 72° C. for 1 minute for 35 cycles. Ten candidate PCR products were obtained and cloned into the TA-cloning vector, pCR21 (Invitrogen, San Diego, Calif.). DNA sequencing was performed using the dyeprimer method with both M13 reverse and -21M13 primers on an ABI automated Sequencer model 377 or 373 (Applied Biosystems, Foster City, Calif.). One of these clones was the 327 bp Sdi-06 clone described above.

To obtain the full-length hJAGGED1 CDNA, a human bone marrow λgt11 CDNA Library (catalogue number HL5005b; Clontech) was screened. The library was plated at $5 \times 10^4$ pfu on LB/Mg agar according to the manufacturer's protocol. After incubation for 8 to 12 hours, plaques were transferred to nitrocellulose filters (Schleicher & Schuell, Inc., Keene, N.H.) and denatured, neutralized, and cross-linked by UV irradiation. The filters were prehybridized and hybridized at 60° C. with solutions prepared as described in Church and Kieffer-Higgins, *Science* 240:185–188 (1988), which is incorporated herein by reference. Following hybridization, filters were washed twice with 2×SSC/ 1%SDS for 10 minutes at room temperature and twice with 0.2×SSC/1%SDS for 20 minutes at 60° C. DNA was isolated from positive clones that were confirmed by a second hybridization under the same conditions. The cDNA clones D-01 and Y-A01, containing the 5' (2.2 kb) and 3' (4.5 kb) cDNA fragments of hJAGGED1, respectively, were cloned into the EcoRI site of the pBluescriptSK-vector (Stratagene, La Jolla, Calif.).

The full-length hJAGGED1 cDNA (pBS-hJg1) was generated by replacing the 300 bp 5' EcoRI/BglII fragment in Y-A01 with the 1.3 kb 5' EcoRI/BglII cDNA fragment in D-01. The resulting 5.5 kb cDNA clone hJAGGED1 was sequenced using random "shotgun" sequencing essentially as described in Smith et al., *Genome Res.* 6:1029–1049 (1996), which is incorporated herein by reference. A shotgun library was constructed by sonicating pBS-hJg1 plasmid DNA, size-selecting 1.5–2 kb fragments on an agarose gel, blunting the ends of the size-selected fragments using mung bean nuclease, and cloning the fragments into Sma I-digested M13–mp18 vector (Novagen, Inc., Madison, Wis.) essentially as described in Rowan and Koop (Eds.), *Automated DNA Sequencing and Analysis* pp. 167–174, Academic Press, Inc. (1994), and Smith et al., *Genome Research* 6:1029–1049 (1996), each of which is incorporated herein by reference. Briefly, single-stranded DNA was prepared from single plaques as described in Smith et al., supra, 1996. Approximately 80 single-stranded DNA templates were sequenced by ABI thermal-cycle sequencing using fluorescently-labeled -21M13 primer following the manufacturer's procedure. Sequencing data was assembled into a single 5.5 kb contig with approximately 6-fold redundancy using the basecalling and sequence assembly programs Phred and Phrap (P. Green, unpublished, http://www.genome, Washington.edu).

Expression of Human Jagged1 mRNA

In order to evaluate the expression pattern of hJAGGED1, Northern blot analysis was performed on multiple human tissues using a hJAGGED1 fragment as a probe. A single 5.5 kb mRNA transcript was detected in all tissues tested, including stomach, thyroid, spinal cord, lymph node, trachea, adrenal gland, and bone marrow. High levels of hJAGGED1 expression were noted in thyroid and trachea, while relatively lower levels of expression were observed in lymph node and bone marrow. Further Northern analysis demonstrated that hJAGGED1 is also expressed in adult heart, lung, skeletal muscle, kidney and placenta. However, hJAGGED1 expression was undetectable in adult brain or liver tissue.

Analysis of human fetal tissues showed high levels of hJAGGED1 expression in fetal kidney (16–32 weeks) and fetal lung (18–28 weeks), with lower levels of expression in fetal brain (20–25 weeks) and fetal liver (16–32 weeks). Expression of hJAGGED1 in heart, fetal liver, lung and kidney is consistent with a role for the hJAGGED1 protein in the normal development of these tissues.

The results described above demonstrate that hJAGGED1 is expressed in whole bone marrow, a heterogeneous tissue consisting of a variety of stromal and hematopoietic cell populations. In order to determine whether hJAGGED1 expression is restricted to certain marrow subpopulations, RNA was isolated from primary human bone marrow stromal cells and analyzed by Northern blotting. A 5.5 kb transcript was detected, indicating that hJAGGED1 is expressed in bone marrow stromal cells. Several cell lines representing functionally distinct bone marrow stromal cells also were analyzed for hJAGGED1 expression. These immortalized human bone marrow stromal cell lines, designated HS-5, HS-23, and HS-27a, have been previously characterized (Roecklein and Torok-Storb, *Blood* 85:997–1005 (1995), which is incorporated herein by reference. The hJAGGED1 transcript was expressed at significant levels in HS-27a cells but was undetectable in HS-5 or HS-23 cells, indicating that hJAGGED1 is differentially expressed in distinct subpopulations of marrow stromal cells.

Northern blot analysis was performed as follows. Northern blots of multiple human tissues and human fetal tissues were obtained from Clontech and probed with $^{32}$P-labeled Sdi-06 or a 400 bp fragment of the hJAGGED1 cDNA. The 400 bp probe was prepared by amplification with primer pair 292 (AGATCCTGTCCATGCAGAACGT; SEQ ID NO:18) and 293 (ATACTCAAAGTGGGCAACGCC; SEQ ID NO:19). For analysis of human stromal cells, 10 µg of total RNA was isolated from primary marrow stromal cells or the indicated stromal cell line using Stratagene's mRNA isolation kit (catalogue number 200347). Total RNA was electrophoresed on a formamide denaturing agarose gel and transferred onto Nytran® membrane (Schleicher & Schuell). Membranes were prehybridized and hybridized using Stratagene's QuikHyb® solution at 65° C. $^{32}$P-labeled probes were denatured by boiling and added directly to prehybridization solution containing 100 µg salmon sperm DNA per 15 ml solution. Membranes were washed twice in 2×SSC/0.1% SDS at room temperature for 10 minutes, followed by washing once with 0.1×SSC/0.1% SDS at 60° C. for 20 minutes. β-Actin cDNA (Clontech) was used as a control for the Northern analysis.

Expression of Human JAGGED1 Polypeptide

The full-length hJAGGED1 cDNA was cloned into the EcoRI/XhoI sites of the IPTG-inducible prokaryotic expression vector, pET-24b(+) (Novagen). The hJAGGED1 expression vector was transformed into B021(DE3) cells, which are bacterial cells containing the T7 RNA polymerase gene under control of an IPTG-inducible promoter.

A cell extract was prepared from transformed cells induced by 0.1 mM IPTG and from control uninduced cells. The cell extracts were fractionated on SDS-PAGE and transferred to nitrocellulose filters. Western analysis was performed with the ECL system (Amersham, Arlington Heights, Ill.) using a monoclonal antibody raised against peptide SEQ ID NO:11 ("J-C"), which corresponds to residues 1096 to 1114 of hJAGGED1 (KRRKPGSHTHSASEDNTTN). A polypeptide of about 150 kDa, absent from the control uninduced extract, was detected in the IPTG-induced cell extract. These results indicate that a hJAGGED1 polypeptide can be expressed in bacteria and that bacterially expressed hJAGGED1 exhibits a molecular weight of about 150 kDa.

EXAMPLE II hJAGGED1 Expressed on Marrow Stroma Inhibits Hematopoietic Differentiation This example demonstrates that a peptide derived from the DSL domain of hJAGGED1 inhibits G-CSF induced granulocytic differentiation of Notch1-expressing myeloid progenitors.

The HS-27a Human Stromal Cell Line Inhibits Differentiation of Myeloid Progenitors Expressing Notch1

The ability of the hJAGGED1 HS-27a human stromal cell line to effect differentiation of hematopoietic progenitors was analyzed using the interleukin-3 (IL-3)-dependent myeloid cell line, 32D. The 32D cell line, which was derived from normal mouse bone marrow, is a heterogeneous cell line with individual cells having characteristics of myeloid cells at various early stages of maturation. 32D cells proliferate as undifferentiated blasts in the presence of IL-3, but differentiate into mature granulocytes when stimulated with granulocyte colony stimulating factor (G-CSF; Valtieri et al. *Immunol.* 138:3829–3835 (1987), which is incorporated herein by reference), thereby providing a system for analyzing factors that may affect myeloid differentiation.

Figure 3A:
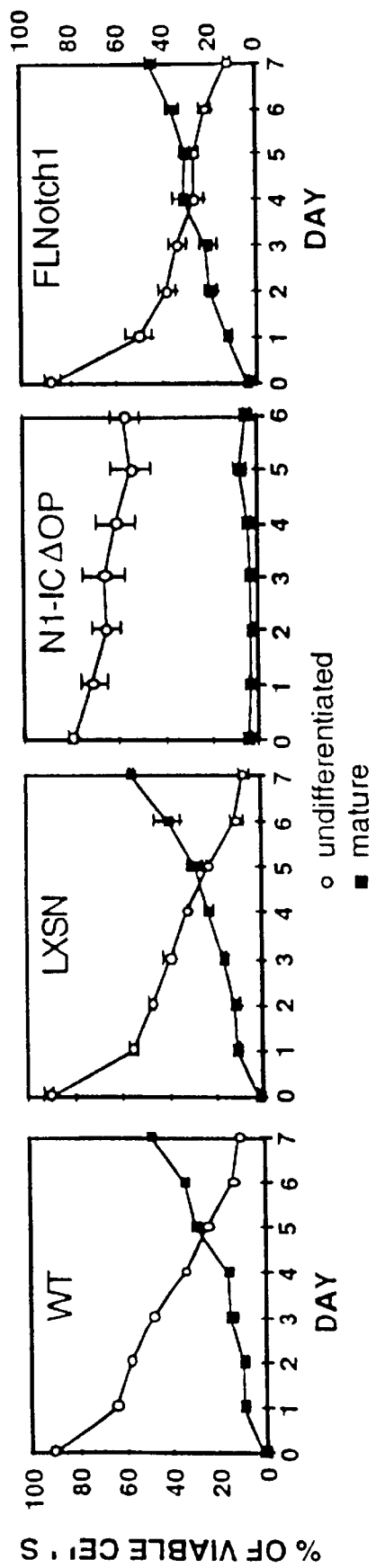
FIG. 3. Inhibition of granulocytic differentiation by the hJAGGED1-expressing stromal cell line, HS-27a. (A) Granulocytic differentiation of 32D myeloid progenitor cells in response to granulocyte colony stimulating factor (G-CSF). The parental 32D cell line (WT) and 32D cells transduced with control LXSN retrovirus or retrovirus containing full-length murine Notch1 cDNA (FL Notch1) were evaluated for granulocytic differentiation in response to G-CSF. The relative percentages of cells remaining undifferentiated (o) or showing morphologic characteristics of mature granulocytes (■) are shown; cells showing some characteristics of differentiation, but which were less mature than band cells were excluded from this analysis. This figure shows results obtained concurrently with those depicted in FIG. 4 and represents one of three experiments with comparable results. Plots for the LXSN control clones and the FL Notch1 clones each represent the average obtained for three clones with error bars indicating the SEM. The data for 32D cells expressing the activated Notch1 construct, N1-ICΔOP were obtained on a separate occasion and represent the averages and SEM of six independent clones. (B) Granulocytic differentiation of 32D cells in the presence of G-CSF when cultured on the human stromal cells line HS-27a, HS-23 or HS-5. The results depicted represent data from three separate experiments, each including three LXSN and three FL Notch1 clones as well as the parental 32D line (not shown). Each plot therefore represents the average and SEM of nine values. The center panels show representative Wright stained cells after four days in culture; the same two clones, LXSN-10 and FLN2.4, are depicted in each set of panels.

Expression of an activated form of murine Notch1 inhibits G-CSF-induced granulocytic differentiation of 32D cells while permitting expansion of undifferentiated progenitor cells (Milner et al., supra, 1996). The function of hJAGGED1 was assayed by transducing 32D cells with a full-length Notch1 cDNA and evaluating the differentiative capacity of the transduced cells under several culture conditions. As shown in FIG. 3A, 32D clones expressing full-length Notch1 differentiate in response to G-CSF in a manner similar to parental 32D cells (WT) or clones expressing control retroviral constructs (LXSN). In contrast, 32D clones expressing the activated intracellular domain of Notch1 (N1-ICΔOP) remain primarily undifferentiated under these conditions, consistent with the results reported in Milner et al., supra, 1996 (FIG. 3A).

Figure 3B:
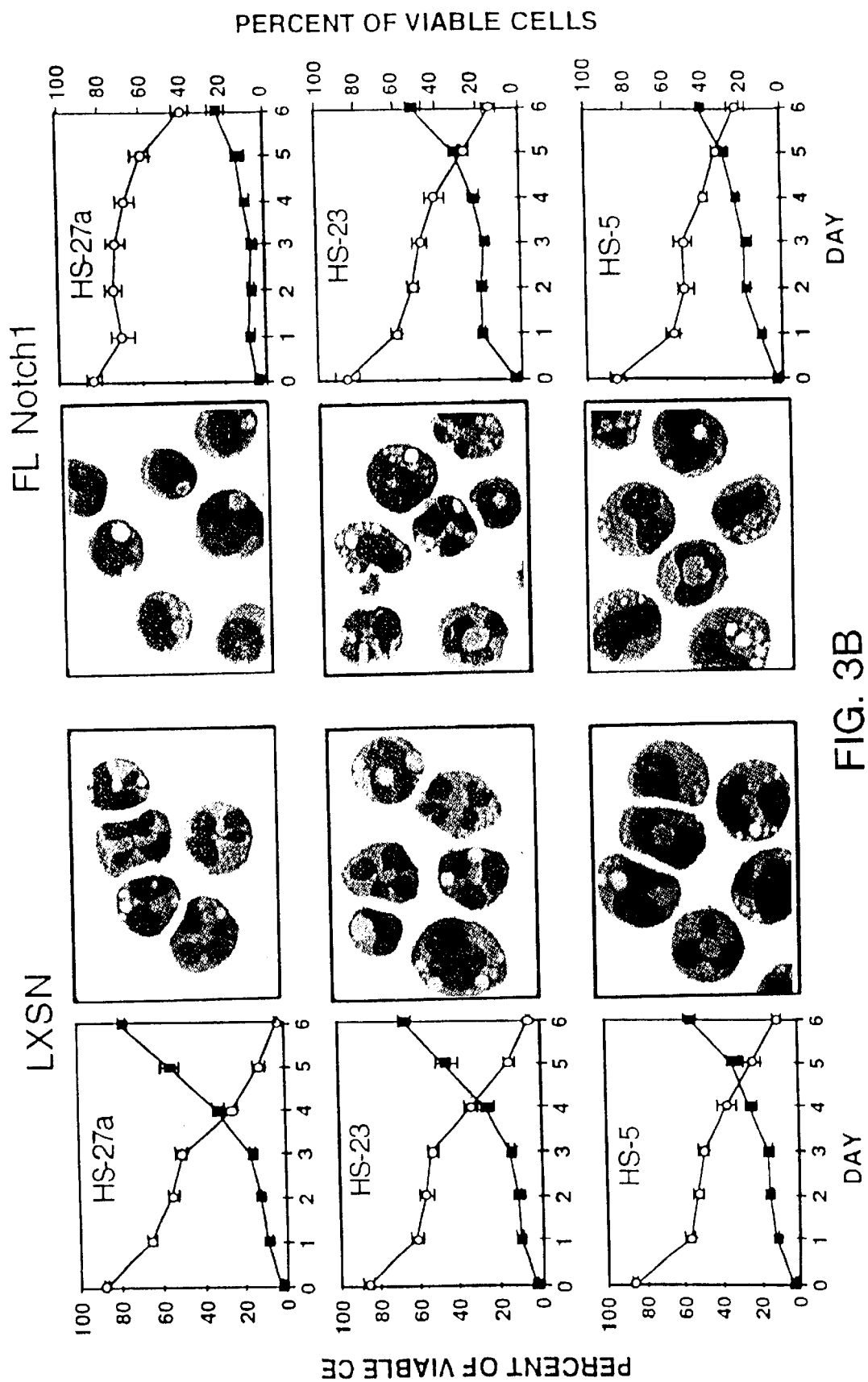

Full-length Notch1-expressing 32D myeloid progenitors were co-cultured with hJAGGED1-expressing HS-27a human stromal cells, and differentiation of the 32D cells assayed. FIG. 3B shows the differentiation patterns of 32D clones expressing full-length Notch1 or the control pLXSN retrovirus in the presence of G-CSF on monolayers of HS-27a, HS-23 or HS-5 stromal cells. LXSN control clones differentiate into mature granulocytes when cultured on any of these cell lines (FIG. 3B, left panels); by day 6, 50–80% of the cells have a mature phenotype, and less than 15% remain undifferentiated. Full-length Notch1-expressing 32D cells also differentiate in response to G-CSF when cultured on the HS-23 or HS-5 lines, but granulocytic differentiation is significantly inhibited in the presence of HS-27a cells (FIG. 3B, right panels). When cultured on HS-23 or HS-5 cells, 40–50% of the cells are mature with 15–20% remaining undifferentiated by day 6. In contrast, only 20% of the 32D cells are mature with 40% remaining undifferentiated when cultured on the HS-27a stromal cell line. The middle panels of FIG. 3B show representative Wright stained cytospins of cells after four days in culture. The greatest difference between control and Notch1-expressing 32D cells occurs in the HS-27a co-cultures. These findings demonstrate that a specific interaction between HS-27a cells and Notch1 on 32D cells inhibits granulocytic differentiation, indicating that hJAGGED1 is capable of activating Notch1 in myeloid progenitor cells.

The maintenance of undifferentiated progenitor cells was analyzed under different culture conditions by determining the total number of viable cells and the relative percentages of undifferentiated and mature cells remaining in the cultures on consecutive days. As shown in Table 1, cultures of 32D cells expressing full-length Notch1 maintain close to the original number of cells (90%) as undifferentiated progenitors after five days in G-CSF when cultured on HS-27a stromal cells. This result contrasts with cultures of control 32D cells, in which significantly fewer viable cells remain, almost all of which are differentiated. In the control 32D cells, fewer than 5% of the original number of cells are maintained as undifferentiated cells. Cultures of full-length Notch1-expressing 32D cells also had slightly greater numbers of undifferentiated cells remaining after five days when cultured on HS-23 or HS-5 stromal cells compared to cultures of the control 32D cells. However, cultures of full-length Notch1-expressing 32D cells grown on HS-27a contained significantly greater numbers of undifferentiated cells than those grown on either HS-23 or HS-5.

TABLE 1

Maintenance of undifferentiated cells after culture in the presence of G-CSF and stromal cell lines.

| 32D Clone | Percent of original number of cells plated remaining undifferentiated | | | Replating efficiency |
|---|---|---|---|---|
|  | HS-27a | HS-23 | HS-5 | HS-27a |
| LXSN | 5 ± 4.7 | 4 ± 3 | 2 ± 1.2 | 11% |
| FL Notch1 | 90 ± 28 | 15 ± 2.6 | 19 ± 29 | 190% |

To verify that cells appearing undifferentiated by morphology were both viable and capable of continued proliferation as undifferentiated cells, cells were replated in WEH1 conditioned media (WCM) containing IL-3 after 6 days in culture with G-CSF and HS-27a cells. The cloning efficiency was evaluated by serial dilutions in 96-well plates as described further below. Compared to the original number of cells plated, the calculated percentage of clonable cells remaining was 190% for the full-length Notch1-expressing 32D cells and 11% for control 32D cells (see Table 1). These results indicate that co-culture of Notch1-expressing 32D cells in the presence of hJAGGED1-expressing HS-27a cells permits survival and maintains the proliferative potential of undifferentiated myeloid cells even in the presence of a differentiative stimulus such as G-CSF.

Notch1 cDNA retroviral vectors were constructed and transduced as follows. The full length clone of murine Notch1, provided by Drs. Jeff Nye and Raphael Kopan (Nye et al., *Development* 120:2421–2430 (1994); and Kopan and Weintraub, *J. Cell Biol.* 121:631–641 (1993), each of which is incorporated herein by reference) was subcloned into the EcoRI site of the pLXSN retroviral vector (Milner et al., supra, 1996). Retroviral producer cell lines expressing Notch1 were generated essentially as described in Milner et al., supra, 1996, and construct expression was confirmed by RT-PCR or western blot analysis. 32D cells were transduced by transwell co-cultivation with Notch1/PA317 producer cells as described in Milner et al., supra, 1996. Notch1-expressing 32D clones were selected in G418 and expanded, and expression was confirmed by RT-PCR and western blotting using a monoclonal antibody generated against the intracellular domain of murine Notch1 provided by L. Milner.

The HS-27a, HS-23 and HS-5 human stromal cell lines were maintained in RPMI containing 10% FCS as described in Roecklein and Torok-Storb, supra, 1995. 32D cells were maintained in Iscove's Modified Dulbecco's Medium (IMDM) with 10% fetal bovine serum (FBS) and 10% WCM as a source of IL-3. For differentiation experiments, 32D cell lines were harvested in log phase, washed, counted, and replated at constant density ($2\times10^5$ cells/ml, 4 ml/well) in 6-well plates in IMDM, 10% FBS, 0.5% WCM and 20 ng/ml recombinant human G-CSF from Amgen (Thousand Oaks, Calif.). Aliquots of 20 ml were removed daily for analysis and replaced with fresh media. Viable cells were counted, and Wright stained cytospins were evaluated for granulocytic differentiation as follows. Undifferentiated 32D cells generally had a single large, relatively round nucleus and scant dark blue cytoplasm containing few large granules. Criteria for granulocytic differentiation included nuclear segmentation, an increased cytoplasmic to nuclear ratio, and increased eosinophilia and granularity of the cytoplasm. Differential cell counts were performed on 100–200 cells on several occasions and in random/blinded fashion by the same individual (LM) to ensure consistency. The differential cell counts were confirmed by independent observers in a blinded fashion.

For co-culture experiments with 32D cells, human stromal cell lines were cultured in 6-well plates to approximately 75% confluence, washed and plated with 32D cells as described above, with the exception that 32D cells were plated at a density of $4\times10^5$ cells/ml in 2 ml on the stromal cell layer and incubated for one to two hours prior to the addition of media containing G-CSF.

For assessment of cloning efficiency shown in Table 1, 32D cells were cultured at various cell densities ($2\times10^5$, $1\times10^4$, or $2.5\times10^4$/ml) in 6-well plates as described above. After 6 days in culture with media containing 20 ng/ml G-CSF and 0.5% WCM on HS-27a stromal layers, 32D cells were harvested and replated in triplicate in 10% WCM in 96-well plates. Serial dilutions were made, and wells assessed for growth daily for seven to ten days. Positive wells all showed continued proliferation during the period of observation and contained greater than 100 cells by day seven to ten.

A hJAGGED1 DSL Peptide Inhibits Differentiation of Notch1-expressing Myeloid Progenitors Three peptides corresponding to different regions of the hJAGGED1 molecule were analyzed for their effect on differentiation of Notch1-expressing 32D cells treated with G-CSF. Peptide SEQ ID NO:9 ("J-A") contains residues 188 to 204 of hJAGGED1 and corresponds to a hydrophilic portion of the conserved DSL domain, which is a domain unique to putative Notch ligands. Peptide SEQ ID NO:10 ("J-B") contains residues 235 to 257 and corresponds to part of EGF-repeat 1 in the extracellular domain. Peptide SEQ ID NO:11 ("J-C") contains residues 1096 to 1114 and corresponds to a hydrophilic portion of the intracellular domain. FIG. 4 shows differentiation of control (LXSN) and full-length Notch1-expressing 32D cells in response to G-CSF in the presence of peptide SEQ ID NO:9, SEQ ID NO:10 or SEQ ID NO:11. G-CSF-induced differentiation of control clones was unchanged by the addition of any of the peptides (FIG. 4, left panels; compare to G-CSF alone in FIG. 3A). Differentiation of the full-length Notch1-expressing 32D clones in the presence of G-CSF and either peptide SEQ ID NO:10 or SEQ ID NO:11 ("J-B" or "J-C"; FIG. 4, top right) was comparable to that observed with G-CSF alone (see FIG. 3A). In contrast, differentiation was significantly inhibited in the presence of peptide SEQ ID NO:9 ("J-A") (FIG. 4, lower right). The extent of inhibition was similar to that observed when these cells were co-cultured on the HS-27a monolayer in the presence of G-CSF (see FIG. 3B).

Peptide SEQ ID NO:9 ("J-A") has the sequence CDDYYYGFGCNKFCRPR. Peptide SEQ ID NO:10 ("J-B") has the sequence CRQGCSPKHGSCKLPGDCRCQYG); and peptide SEQ ID NO:11 ("J-C") has the sequence KRRKPGSHTH-SASEDNTTN. Each of these peptides were synthesized at the University of Washington Biopolymer Facility. Differentiation of 32D cells in the presence of hJAGGED peptides was analyzed as described above. 32D cells were incubated in media containing 20 μM peptide for 1 hour prior to the addition of G-CSF to a final concentration of 20 ng/ml. The final peptide concentration for the experiment depicted in FIG. 4 was 10 μM. Fresh peptide was added to the original concentration on day 4 of culture.

An Active Fragment of hJAGGED1 Inhibits Granulocytic Differentiation of Mouse Hematopoietic Progenitor Cells A soluble fragment of hJAGGED1 (SEQ ID NO:7), which contains the extracellular domain of hJAGGED1 including the signal peptide, DSL region, EGF-like repeats and cysteine-rich region, was prepared by amplifying a portion of the hJAGGED1 cDNA with PCR primers 420 (SEQ ID NO:20; CCGCTCGAGACCATGCGTT CCCCACGGA) and 421 (SEQ ID NO:21; CGGAATTCT-CAGTGGTGGTGGTGGTGGTGTTCATTGTTC GCTGAA). The hJAGGED1 cDNA fragment, corresponding to residues 1 to 1010, was subcloned into expression vector pDX to generate pDX-hJg1.Ex. After transfection into BHK and COS cells, the cell culture supernatant was assayed for the ability to effect the number of G-CFU formed from mouse hematopoietic progenitor cells (Sca-1⁻ lin⁻), which were prepared by removing cells that stained with anti-Gr-1, anti-CD4, anti-CD11b, anti-CD2, anti-CD45R and anti-Ter-119 and then positively selecting Sca-1⁺ cells with anti-Sca-1. As shown in Table 2, supernatant from BHK cells transfected with the hJAGGED1 extracellular domain construct reduced the average number of colony forming units (CFU-G-CSF) of Sca-1⁺ lin⁻ cells treated with G-CSF from about 60 to about 24. These results indicate that the hJAGGED1 fragment SEQ ID NO:7 encoding the extracellular domain of hJAGGED1 (residues 1 to 1010) inhibits granulocytic differentiation and is an active fragment of hJAGGED1.

TABLE 2

Number of CFU-G-CSF

| Sample | Supernatant of BHK cells | Supernatant of BHK cells transfected with pDX-hJg1.Ex |
|---|---|---|
| Sample 1 | 99 | 34 |
| Sample 2 | 48 | 20 |
| Sample 3 | 45 | 23 |
| Sample 4 | 48 | 19 |
| Average | 60 | 24 |

A cDNA fragment corresponding to the DSL region of hJAGGED1 (amino acids 178 to 240; SEQ ID NO:8) was amplified using primer 517 (SEQ ID NO:22; CGCGGATCCTCAGCCTTGTCGGCAAATAGC) and 518 (SEQ ID NO:23; CCCAAGCTTGCCCACTTTGAGTATCAGA). The fragment was subcloned into the PinPoint™ expression vector (Promega, Madison, Wis.), and expressed as a fusion protein with a peptide that becomes biotinylated in *E. coli*. After purification of the hJAGGED1 DSL fragment using avidin chromatography, the biotin-tagged hJAGGED1 fragment was assayed for activity in a high proliferative potential (HPP) assay with sorted mouse hematopoietic stem cells (Sca-1⁺, lin⁻) as described in Patel et al., *J. Exp. Med.* 185:1163–1172 (1997), which is incorporated herein by reference). The HPP assay is an assay to test the self-renewal capacity of hematopoietic progenitor cells. Sorted mouse hematopoietic progenitor cells (Sca⁻, lin⁻) were cultured with a combination of growth factors (IL-1, IL-3 and stem cell factor) with or without 50–100 nM biotin-tagged hJAGGED1 DSL fragment SEQ ID NO:8 on soft agar for 10 days. The results of this assay demonstrated that the hJAGGED1 fragment SEQ ID NO:8 increased HPP efficiency two-fold. Thus, the hJAGGED1 fragment SEQ ID NO:8, corresponding to residues 178 to 240 of hJAGGED1, is an active fragment of JAGGED that increases the self-renewal capacity of hematopoietic progenitor cells.

EXAMPLE III

Mapping hJAGGED1 Relative to the Alagille Syndrome Critical Region

This example describes the mapping of the human JAGGED1 gene to chromosome 20p12.

hJAGGED1 Maps to Chromosome 20p12

In order to obtain a probe for fluorescence in situ hybridization (FISH), a total genomic library from Research Genetics (Huntsville, Ala.) was screened with the hJAGGED1 cDNA fragment Sdi-06. Two genomic bacterial artificial chromosome (BAC) clones, 49-D9 and 125-B1, were isolated, and the presence of the hJAGGED1 gene demonstrated by Southern blot analysis.

Probes were ³²P-labeled with PrimIt-II following the manufacturer's procedure (Stratagene, La Jolla, Calif.). Fluorescence in situ hybridization was performed with each BAC clone independently. Both 49-D9 and 125-B1 hybridized specifically to 20p12 in a metaphase spread. FISH signals were observed at 20p12 on both chromosomes in each of the 10 metaphase cells analyzed and were not consistently observed at any other location. These results indicate that the hJAGGED1 gene maps to chromosome 20p12.

Fluorescence in situ hybridization was performed essentially as described in Trask, "Fluorescence in situ hybridization" in Birren et al., (Eds.) *Genome Analysis: A Laboratory Manual* Cold Spring Harbor Laboratory Press (1997) and Krantz, *Am. J. Med Genet.* 70:80–86 (1997), each of which is incorporated herein by reference. Briefly, BAC DNA was biotinylated by nick translation and hybridized to metaphase preparations (2 ng probe/μl). Human Cot1 DNA (GIBCO-BRL) was added to the hybridization solution at a final concentration of 100 ng/ml to prevent hybridization of labeled repetitive sequences to chromosome spreads. Metaphase preparations were obtained from phytohemagglutinin-stimulated peripheral blood lymphocyte cultures that were blocked in early S-phase with methotrexate and released to (pro)metaphase in the presence of bromodeoxyuridine. Hybridization sites were detected with avidin-FITC, and chromosomes were banded with DAPI at 2 μg/ml in an antifade solution. FITC and DAPI images were collected separately, but in registration, using Spectrum Analytics IPLab Spectrum 3.0 software, a Princeton CCD camera (KAF 1400 chip), a Ludl filter-wheel equipped with ChromaTechnology excitation filters, and a Zeiss AxioPhot microscope equipped with a 100x, 13 N.A. objective and a ChromaTechnology multi-band pass emission filter. The images were pseudocolored and merged after the DAPI-banding contrast was enhanced by applying a 5×5 linear HAT filter supplied with the IPLab package. More than 10 metaphases were analyzed from the computer screen or by direct visualization through the microscope.

Mapping hJAGGED1 Relative to the Alagille Syndrome Critical Region.

Figure 5:
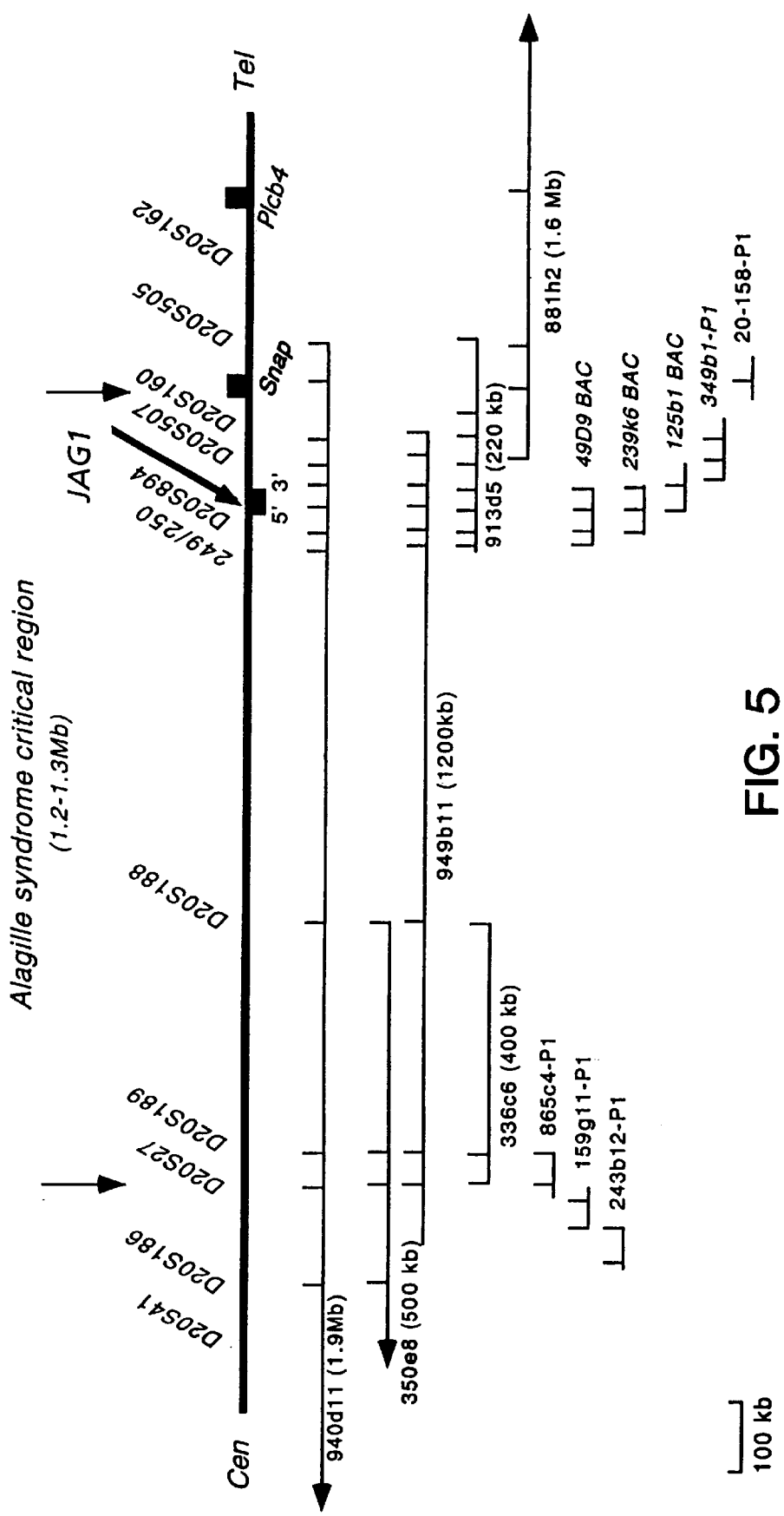
FIG. 5. Mapping hJAGGED1 in the Alagille Syndrome critical region. The critical region has been defined by the shortest region of overlap of patients with deletions of 20p12 by molecular and FISH mapping and extends between P-1 243b12, proximal to D20S27, and clone 20p1-158, proximal to WI-6063. YAC clones are indicated in standard print, P1 clones are indicated as such, and BAC clones are in italic print.

Studies of the minimal region of overlap of multiple patients with cytogenetic deletions have defined an Alagille Syndrome critical region at chromosome 20p12 between genetic markers D20S41 and D20S162 (FIG. 5). A contig of YAC, P1 and BAC clones spanning the critical region was used to further define this region. The distal boundary of the region is defined by a P1 clone (20pl-158), containing the synaptosomal associated protein-25 (SNAP-25). This clone was present in two copies in the patient with the most centromeric deletion (Krantz et al., supra, 1997). The centromeric boundary of the region is defined by P-1243b12, which is outside of the deletion in the patient with the most distal deletion. The size of this critical region is estimated at 1.2 to 1.3 Mb. Two BAC clones 49D9 and 125B1, which contain part of the hJAGGED1 gene, map to the 20p12 region. Using multiple PCR primers 249/250 (SEQ ID NOS: 24 and 25) and 247/248 (SEQ ID NOS:26 and 27) from BAC clone 49D9, on a panel of YAC, P1 and BAC clones, hJAGGED1 was sublocalized between D20S894 and D20S507 within the Alagille Syndrome critical region (see FIG. 5).

CEPH human YAC clones were identified through the Whitehead Institute for Biomedical Research/MIT Center for Genomic Research web site and published data (Pollet et al., *Genomics* 27:467–474 (1995), which is incorporated herein by reference) and provided by Dr. Marcia Budarf (CHOP). The human P1 Library (Shepherd et al., *Proc. Natl. Acad. Sci.* 91:2629–2633 (1994), which is incorporated herein by reference) was screened essentially as described in Stokke et al., *Genomics* 6:134–7 (1995), which is incorporated herein by reference. The human BAC library Stokke et al., supra, 995; Shizuya et al., *Proc. Natl. Acad. Sci.* 89:8794–8797 (1992), which is incorporated herein by reference) was screened according to the protocol supplied by Research Genetics. Selected clones were mapped by FISH and STS content analysis to confirm cytogenetic localization and to order the clones. When clones were not contiguous, clone ends were obtained by sequencing using T7 and SP6 promoters, and new PCR primers were designed based on the sequence for the next round of library screening. Sequencing was carried out in the Nucleic Acid Sequencing Cores at the University of Pennsylvania, Department of Genetics, and at The Children's Hospital of Philadelphia. Fluorescence in situ hybridization studies were carried out by standard techniques essentially as described in, Krantz et al., supra, 1997, which is incorporated herein by reference.

Microsatellite markers were amplified as follows. $(TTTG)_n$ was amplified with primer pair 249/250 (GGTCTTTTGCCACTGTTT; SEQ ID NO:24 and GAAT-AGGGAGGAGAAAAC; SEQ ID NO:25), and $(GTTT)_n$ was amplified with primer pair 247/248 (GTCTTTTGCCACTGTTTG; SEQ ID NO:26 and GAAT-AGGGAGGAGAAAAC; SEQ ID NO:27).

EXAMPLE IV hJAGGED1 Gene Structure

Figure 6A:
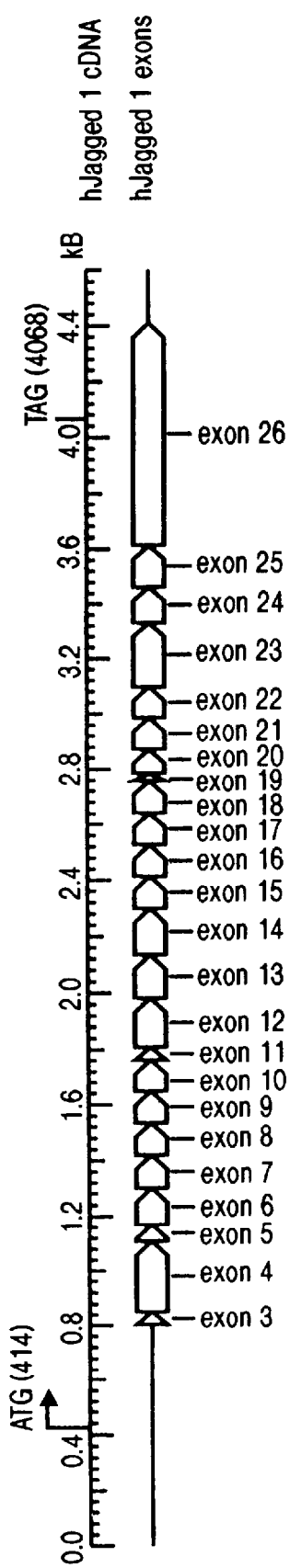
FIG. 6. (A) Schematic diagram illustrating the alignment of the exon boundaries with the hJAGGED1 cDNA sequence. (B) The exon/intron boundary nucleotide sequences are shown for twenty-four hJAGGED1 exons; sequence identification numbers are indicated in parenthesis. One or more 5' exons have not been identified; the 5' most exon identified to date is indicated exon (n+1). The hJAGGED1 cDNA nucleotide positions corresponding to each exon and the exon length are also indicated.

This example describes the identification of the hJAGGED exon/intron boundaries.
Identification of hJAGGED1 Exon/intron Boundaries DNA array technology was used to determine the exon/intron boundaries of the hJAGGED1 gene as described in Nguyen et al., *Genomics* 29:207–216 (1995), which is incorporated herein by reference. BAC clone 49D9 was fragmented by sonication, and fragments ranging in size from 1.5 to 2 kb were selected and ligated into an M13 bacteriophage vector. Individual single stranded M13 clones were picked into 384-well microfilter plates, and 1,536 clones were arrayed onto four sets of nylon membranes using a 384-pin Replicator. The arrays of the BAC 49D9 M13 fragments were hybridized with the full length hJAGGED1 cDNA. All positive M13 clones (approximately 100 clones) were picked and sequenced. The hJAGGED1 genomic and cDNA sequences were aligned, and 47 intron/exon boundaries were defined (FIG. 6A and 6B). The sequences from the 5' end, upstream of base pair 803 of the hJAGGED1 cDNA sequence, were missing one or two exons, presumably because the 5' end of the gene is not contained in the BAC 49D9 clone (FIG. 6A). The 5' identified exons are indicated exon (n+1), where n stands for the unknown number of missing exons (see FIG. 6B). The intron/exon and exon/intron boundary sequences of hJAGGED1 exons 3 through 26 are shown in FIG. 6B as SEQ ID NOS:28 through 74.

BAC DNA sequence analysis was performed using random shot-gun sequencing essentially as described above. Approximately 100 single-strand DNA templates were cloned into pCR.2.1 vector using the TA cloning system from Invitrogen. DNA was prepared using 5'-3' DNA mini-preparation system (5'prime-3'prime, Inc., Boulder, CO) and sequenced. Fluorescently-labeled -21M13 primer was used for sequencing of single-stranded DNA, and fluorescently labeled -21M13 and M13 forward primers were used for sequencing of double-stranded cDNA following the manufacture's procedure (ABI).

EXAMPLE V

Alagille Syndrome Associated hJAGGED1 Mutations

Figure 7A:
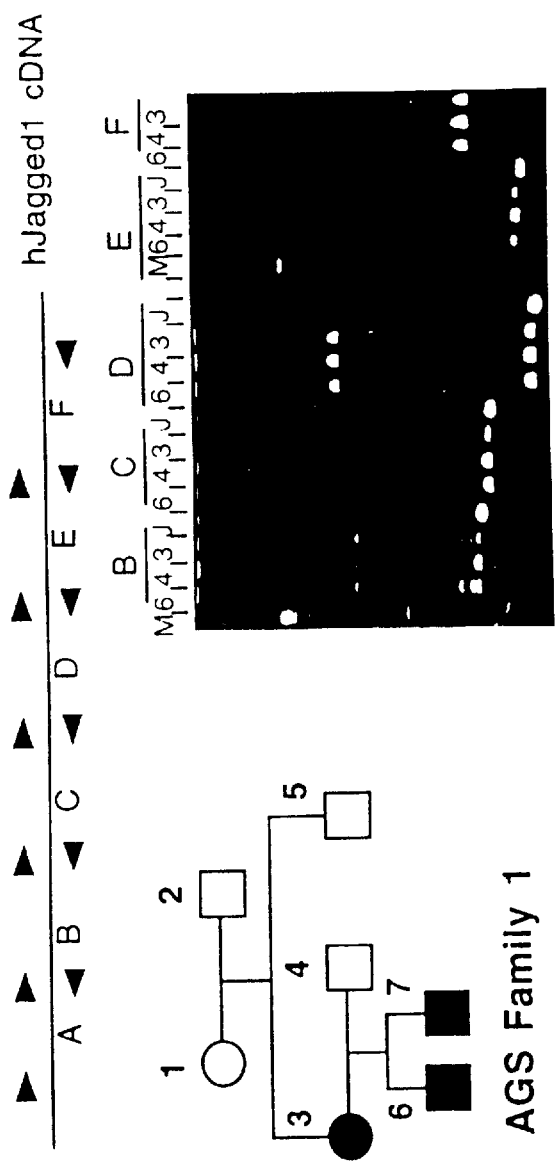
FIG. 7. Heteroduplex Mobility Analysis (HMA) of hJAGGED1 cDNAs in four Alagille Syndrome (AGS) families. (A) A schematic diagram showing the positions of the primers used in RT-PCR, and the amplified cDNA regions A through F. (B) HMA of three members of AGS family 1. PCR product amplified from the hJAGGED1 cDNA clone is shown as a reference (lane J). (C) Analysis of three members of AGS family 2. (D) Analysis of two affected members of AGS family 3 and 4. (E) Analysis of cloned cDNA fragments, each containing one variant. Normal clones from region B, C and D are indicated as B-nl, C-nl and D-nl, respectively. (F) HMA of the hJAGGED1 cDNA region A of 10 individuals from AGS families 1–4, showing no heteroduplex formation.

This example describes the association of several independent hJAGGED1 coding sequence mutations with Alagille Syndrome in four Alagille families.
Heteroduplex Mobility Analysis (HMA) of Alagille Syndrome Families The hJAGGED1 gene contains at least 26 exons, and its mRNA is 5.5 kb in length. Heteroduplex mobility analysis (HMA) was used to screen for Alagille Syndrome-associated mutations in six RT-PCR products spanning the hJAGGED1 mRNA. HMA analysis is an assay that can readily detect mutations in heterozygotes at a given locus and is therefore potentially useful in screening for mutations in dominant disorders (Delwart et al., *Science* 262:1257–1261 (1993), which is incorporated herein by reference). Initially, ten individuals from four Alagille Syndrome families, each with multiple affected members, were screened by HMA (FIG. 7). None of these families demonstrated deletions of 20p12 by cytogenetic or molecular analyses. RT-PCR was performed with six primer pairs to generate small overlapping cDNA fragments, designated A, B, C, D, E and F, which span most of the hJAGGED1 coding sequence (FIG. 7A). After localizing the mutation within one of the six amplified fragments, the cDNA region was sequenced and the identity of the mutation confirmed at the genomic level as described further below.

Shown in FIG. 9 are the normal CNRAICRQGCS (SEQ ID NO:103) and corresponding mutant CNSYLPTRLQS* (SEQ ID NO:104) amino acid sequences of Alagille Syndrome family 1; the normal WCGPRPCL (SEQ ID NO:105) and corresponding mutant WCGVALDL (SEQ ID NO:106) amino acid sequences of Alagille Syndrome family 2; the normal DSQCD (SEQ ID NO:107) and corresponding mutant DSVMR (SEQ ID NO:108) amino acid sequences of Alagille Syndrome family 3; and the normal FCKCPED (SEQ ID NO:109) and corresponding mutant FCKCPRT (SEQ ID NO:110) amino acid sequences of Alagille Syndrome family 4.

Analysis of Alagille Syndrome Family 1

HMA analysis of family 1 indicated a mobility shift in PCR product "B" in two affected individuals (FIG. 7B). Sequence analysis of the hJAGGED1 cDNAs from affected family members demonstrated a deletion of nucleotides "AG" at positions 1104 and 1105. To confirm that the two nucleotide deletion in the "B" region causes the mobility shift detected by HMA, cloned RT-PCR products from affected and unaffected family members were analyzed. cDNA with the "AG" deletion in combination with clones from a non-deleted individual produced an expected mobility shift identical to that of cDNAs from the RT-PCR products (FIG. 7F and 7B). As anticipated, HMA analysis of each individual clone did not lead to the mobility shift. Fifteen cDNA clones from the "B" region were sequenced from each individual analyzed. Normal sequences were detected in all individuals in this family, but affected individuals demonstrated both mutant and normal alleles. The "AG" deletion lies in exon (n+2).

Figure 8B:
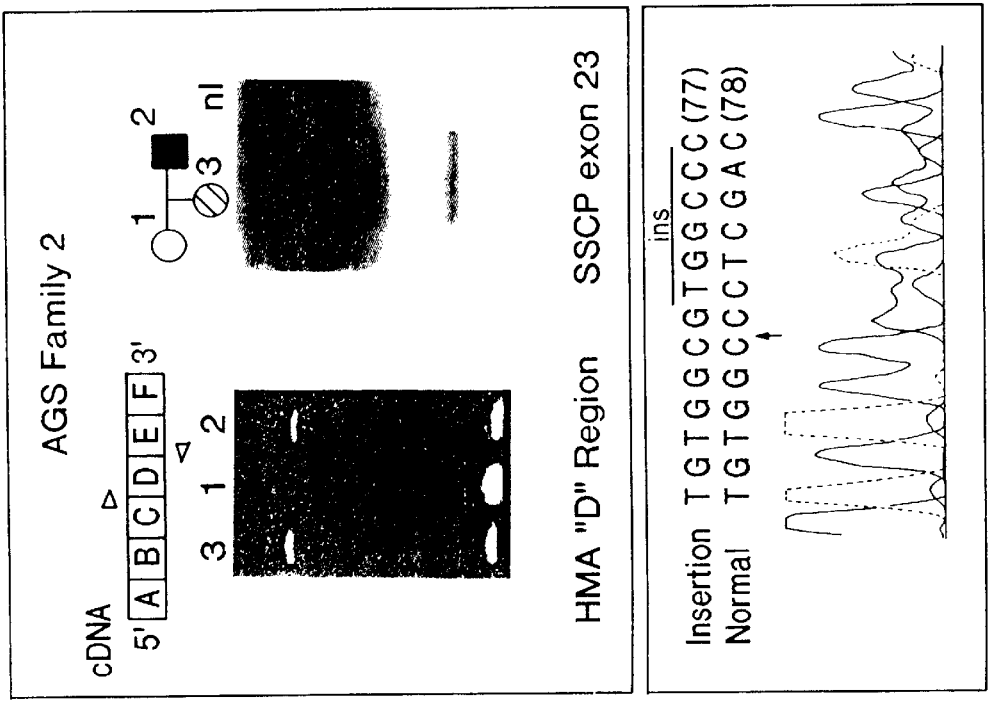
FIG. 8. Segregation of SSCP variants in four Alagille Syndrome families. Individuals with filled circles meet full criteria for diagnosis with Alagille syndrome. Individuals with hatched circles have some of the characteristics of the syndrome. (A) Segregation of an exon (n+2) variant in two children with liver, heart, eye and facial features of Alagille Syndrome and their mildly affected mother. Sequence analysis demonstrates a 2 bp "AG" deletion. (B) Segregation of an exon n+21 variant in a child with Alagille facies and pulmonic stenosis and her more severely affected father. Sequence analysis demonstrates a 5 bp insertion (GTGGC) in father and daughter. (C) Family 3 demonstrates an exon (n+15) variant in an affected mother, her affected daughter and DNA from a terminated pregnancy. Sequence analysis demonstrates a 4 bp deletion in affected individuals. (D) Family 4 has an exon 15 variation in a child with severe cardiac and liver disease who died at 5 years of age and her less severely affected father. Sequence analysis in father and daughter demonstrated a single nucleotide "IC" deletion. Sequence identification numbers are indicated in parenthesis.
Figure 8A:
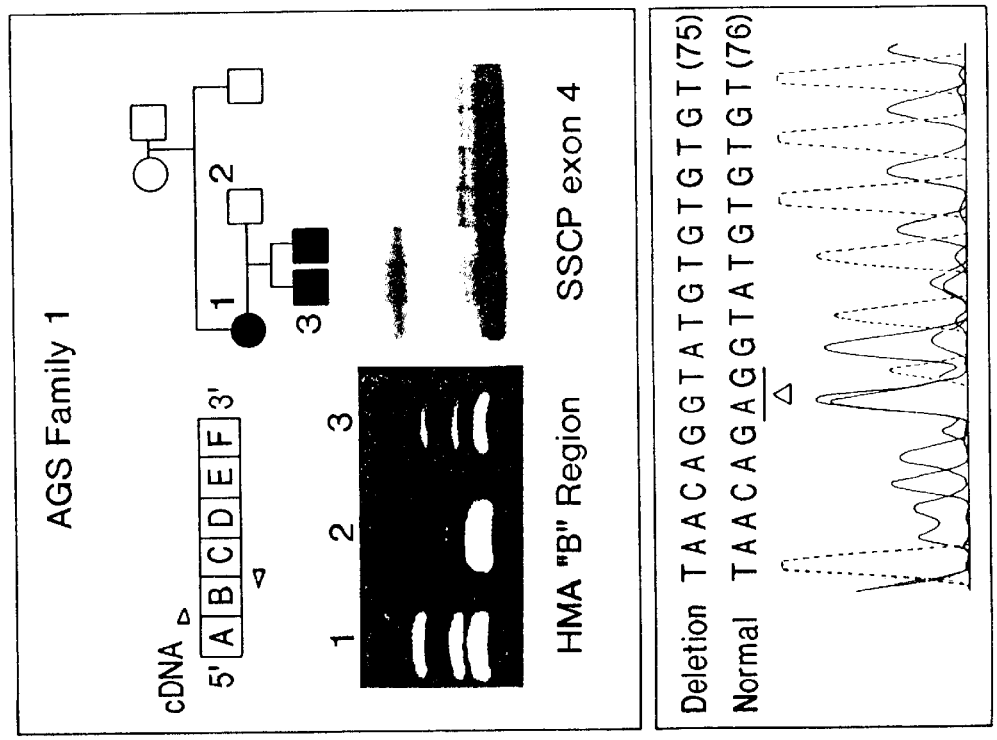

Single strand conformational polymorphism (SSCP) analysis of exon 4 (designated exon n+2) on the extended family revealed a mobility shift in the three affected individuals in this family (FIG. 8A). Furthermore, this deletion was confirmed by sequence analysis of the genomic DNA of exon (n+2) (FIG. 8A). The disease-associated and normal nucleotide sequences of Alagille Syndrome family 1 in the region of this deletion are shown in FIG. 8A as SEQ ID NOS:75 and 76, respectively. The "AG" deletion leads to a reading frame shift at residue 230, positioned at the end of the DSL domain, and is predicted to result in premature termination at residue 240. Thus, the "AG" deletion in family 1 results in a truncated hJAGGED1 protein lacking the 979 C-terminal residues (see FIG. 9).

The two affected brothers in this family have liver disease, heart disease including pulmonic and peripheral pulmonic stenosis, posterior embryotoxon and Alagille facies. Their less severely affected mother has a heart murmur, posterior embryotoxon and Alagille facies.

Analysis of Alagille Syndrome Family 2

HMA analysis was similarly performed on family 2. PCR products from two affected members of family 2 showed mobility shifts in the "D" region (FIG. 7C). cDNA sequence analysis of amplified "D" region sequences from both affected individuals revealed two changes: a five nucleotide insertion (GTGGC) at position 3102 and an 86 nucleotide deletion from nucleotides 2785 to 2871. The insertion is a repeat of the GTGGC sequence at positions 3102–3107. The 86 nucleotide deletion was seen in all three members of this family, one of whom is unaffected, and corresponds to a complete absence of exon 23 (exon n+21). This result indicates that this exon can be removed from the final transcript by alternative splicing and that the 86 nucleotide deletion does not correlate with disease phenotype. Analyses in the "D" region of 10 individuals from four families identified a common heteroduplex. This observation is consistent with the presence of transcripts both containing and deleting exon (n+18) in all individuals tested (FIGS. 7B, C and D).

The multiple bands seen by HMA in the "D" region corresponded to the three types of variation identified by sequencing: a 5 bp insertion, a 86 bp deletion, and both a 5 bp insertion and an 86 bp deletion. Three cloned CDNA fragments, generated by PCR using the "D" region primers from individuals in Alagille Syndrome family 2, were tested. Each clone contains one variant. A clone from AGS2–2 (AGS 2–2$_1$) contained the 5 nucleotide insertion. A clone from AGS 2–3 contained the 86 nucleotide deletion, and a third clone from AGS2–2 (AGS2-2$_2$) contained the 5 nucleotide insertion in addition to the 86 nucleotide deletion. These clones were hybridized with the normal clone D-nl and analyzed by HMA. As shown in FIG. 7E, these three types of hybridizations correspond to the heteroduplexes seen. These results indicate that only the five bp insertion correlates with the Alagille Syndrome disease phenotype. This disease-associated 5 bp insertion was localized to exon (n+21).

SSCP analysis revealed a novel band in this exon, present in an affected father and daughter and absent in the unaffected mother and in 50 normal control individuals (FIG. 7C). The disease-associated and normal nucleotide sequences of Alagille Syndrome family 2 in the region of the mutation are shown in FIG. 8B as SEQ ID NOS:77 and 78, respectively. The insertion, which was confirmed by genomic sequence analysis of the mutant hJAGGED1 genes in both affected individuals, is predicted to result in a translational frameshift downstream of codon 898. Translation is predicted to terminate at codon 945, resulting in a truncated hJAGGED1 protein lacking the C-terminal 274 residues. The mutant protein is predicted to contain the DSL domain, the entire EGF repeat domain, and about a third of the cysteine-rich domain, with an additional segment of 47 residues altered by the translational frameshift. The remainder of the cysteine-rich domain, the transmembrane (TM) domain and the intracellular region have been deleted (see FIG. 9).

The phenotypes of the two affected individuals in this family are different. The father has liver disease, cardiac disease, and renal failure, while his daughter is more mildly affected with characteristic facies and pulmonary artery stenosis but normal liver and kidney function to date.

Analysis of Alagille Syndrome Family 3

The two affected individuals in this family showed shifts in the "C" region PCR products (FIG. 7D). Sequence analysis revealed a four nucleotide "CAGT" deletion at positions 2531–2534 in exon (n+15) in both affected individuals. HMA analysis of a cDNA clone carrying the "CAGT" deletion, and a clone from a normal family member demonstrated a mobility shift (FIG. 7F) identical to the RT-PCR products (FIG. 7D).

Figure 8D:
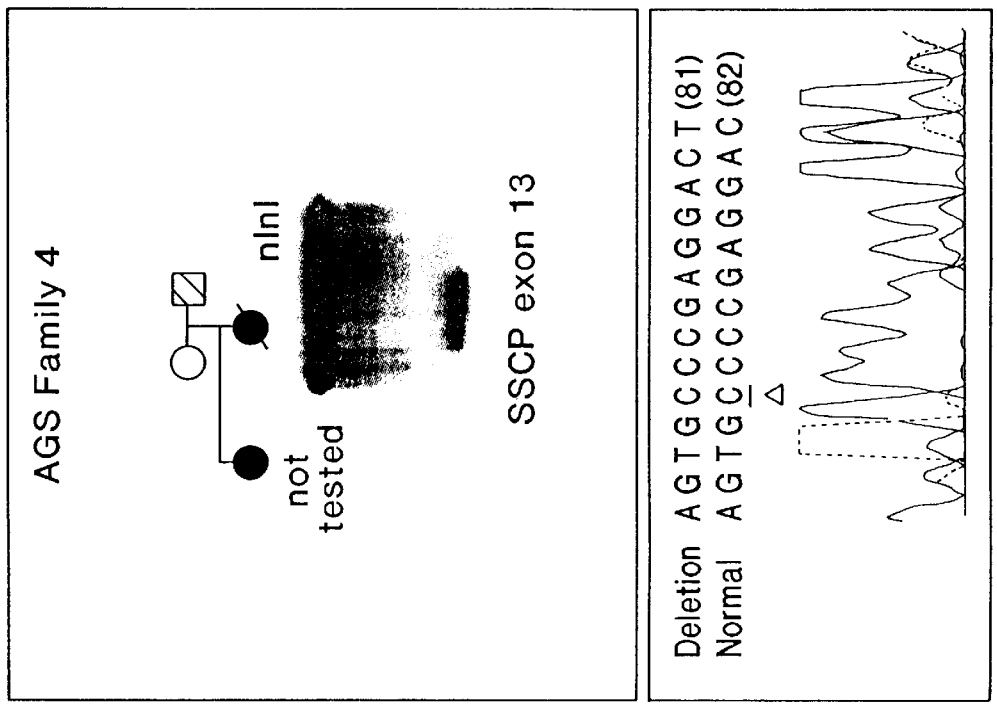
Figure 8C:
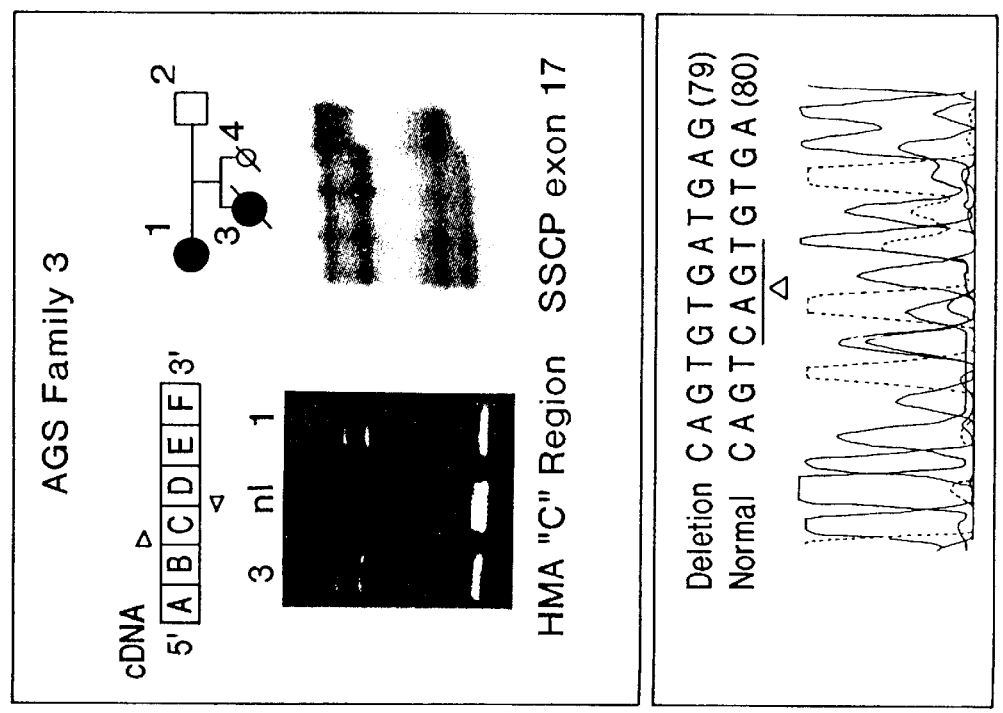

SSCP analysis of exon (n+15) revealed a novel band in the affected proband, her affected mother, and in the DNA from the conceptus of a terminated pregnancy (FIG. 8C). The SSCP variant was not identified in 50 control individuals (100 chromosomes). The four nucleotide deletion was confirmed by genomic sequencing of exon 17 (exon n+15) from the affected individuals (FIG. 8C). The disease-associated and normal nucleotide sequences of Alagille Syndrome family 3 in the region of the deletion are shown in FIG. 8C as SEQ ID NOS:79 and 80, respectively. The mutant gene is predicted to encode an hJAGGED1 protein having a translational frameshift at residue 741 with an altered segment of 33 amino acids before chain termination. The translational frameshift occurs in the 12th EGF repeat as shown in FIG. 9.

The proband in this family was severely affected, with liver involvement, severe branch pulmonary artery stenosis, butterfly vertebrae, and posterior embyrotoxon. She died at 2.5 years of age from head trauma after a fall. Her mother has a milder phenotype coming to medical attention at 20 years of age during pre-surgical evaluation for a basilar artery aneurysm. Studies at that time revealed abnormal liver function; further tests revealed bile duct paucity, pulmonic stenosis, characteristic facies and posterior embryotoxon with retinal changes.

Analysis of Alagille Syndrome Family 4

No heteroduplexes were seen in any of the six PCR products from individuals in this family (FIG. 7D and 7F). However, cDNA sequence analysis revealed a single "C" nucleotide deletion at position 2066 in an affected daughter and father (FIG. 7D). This deletion lies in exon (n+11).

SSCP analysis of exon (n+11) revealed an altered band in the proband and her father (FIG. 8D). Genomic sequence analyses verified the presence of the "C" deletion in exon 13 (exon n+11) in both affected family members. The disease-associated and normal nucleotide sequences of Alagille Syndrome family 4 in the region of the nucleotide deletion are shown in FIG. 8D as SEQ ID NOS:81 and 82, respectively. The deletion shown in. FIG. 8D is predicted to result in a translational frameshift at residue 550 followed by an altered 13 residue segment before chain termination in EGF repeat 9 (FIG. 9).

The proband was severely affected with liver and heart disease (tetralogy of Fallot), facial features of Alagille Syndrome, butterfly vertebrae and posterior embryotoxon. She died at 5 years of age from sepsis. Her father was mildly affected with a history of a heart murmur and characteristic facies. Liver studies were normal; an ophthalmology exam has yet to be conducted. The proband's sibling is also apparently affected, having severe congenital heart disease (tetralogy of Fallot) and posterior embyrotoxon. Her liver studies have been normal.

The Alagille Syndrome patients studied were subject to a complete diagnostic examination. All probands met the diagnostic criteria for the disorder. The proband of each family had Alagille syndrome as judged by the presence of bile duct paucity in addition to a minimum of three of the five following clinical criteria: cholestasis, cardiac disease, vertebral anomalies, anterior chamber defects of the eye and characteristic facial features. Additional family members were examined or their medical records reviewed. All patients and their families were enrolled in the study under an IRB approved protocol at the Children's Hospital of Philadelphia.

RT-PCR and Heteroduplex Mobility Analysis was performed as follows. Total RNA was isolated using Trizol RNA isolation kit (GIBCO-BRL), and cDNA was synthesized using GIBCO/BRL's reverse transcription system following the manufacture's procedure. Taq polymerase (Perkin Elmer) was used to amplify one-twentieth the volume of the reverse transcribed cDNA. The hJAGGED1 cDNA "A" segment was amplified with primers 292/395 (AGATCCTGTCCATGCAGAACGT; SEQ ID NO:83 and CATCCAGCCTTCCATGCAA; SEQ ID NO:84); the "B" segment was amplified with primers 398/399 (CTTTGAGTATCAGATCCGCGTGA; SEQ ID NO:85 and CGATGTCCAGCTGACAGA; SEQ ID NO:86); the "C" segment was amplified with primers 402/403 (CGGGATTTGGTTAATGGTTAT; SEQ ID NO:87 and GGTACCAGTTGTCTCCAT; SEQ ID NO:88); the "D" segment was amplified with primers 406/407 (GGAACAACCTGTAACATAGC; SEQ ID NO:89 and GGCCACATGTATTTCATTGTT; SEQ ID NO:90; the "E" segment was amplified with primers 408/409 (GAATATTCAATCTACATCGCTT; SEQ ID NO:91 and CTCAGACTCGAGTATGACACGA; SEQ ID NO:92); and the "F" segment was amplified with primers 410/411 (AAAGTGCCCAGAGCTTAAACCG; SEQ ID NO:93 and GGTGTTTTAAACATCTGACGTCGTA; SEQ ID NO:94).

Heteroduplex mobility analysis was performed using the following procedure: 200–500 ng of DNA was denatured at 96° C. for five minutes in denaturing buffer (0.1M NaCl, 10 mM Tris HCl (pH 7.8), and 2 mM EDTA). The denatured DNA was immediately removed to a wet ice bath for five minutes and subsequently incubated at 55° C. for five minutes. The reannealed DNA was mixed with loading buffer (0.2% Orange G, 2.5% Ficoll) and electrophoresed on a 5% polyacrylamide gel (19.5×19 cm) in 1×TBE buffer for 3 to 3.5 hours at 250 volts. After electrophoresis, the gel was stained in 0.5 μg/ml ethidium bromide.

SSCP analysis was performed as follows. DNA was extracted from lymphocytes (whole blood) or established lymphoblastoid cell lines of affected and unaffected members of each Alagille family and from unrelated normal control subjects using the Puregene DNA isolation kit (Gentra Systems, Inc., Minneapolis, Minn.). The primers for PCR analysis were designed to cover all exons as well as the intron/exon boundaries of hJAGGED1 as outlined in FIG. 6B. For SSCP analysis, each PCR reaction contained 75 ng of genomic DNA, 200 μM DATP, dTTP, and dGTP, and 62.5 μM dCTP, 4 μCi of $^{32}$P-dCTP, 10 pM of each primer, 1.0–1.5 mM MgCl$_2$, 2.5 μl dimethyl sulfoxide, 2.5 μl of 10X PCR Buffer II (Perkin Elmer, Foster City, Calif.), and 0.75 U AmpliTaq polymerase (Perkin Elmer) in a final volume of 25 μl. Exon (n+4) was amplified with primer pair 510/511 (CAGGGAAGAAGGCTGCAATGT; SEQ ID NO:95 and TGGTGGGGTGATAAATGGACAC; SEQ ID NO:96); exon (n+11) was amplified with primer pair 447/448 (GTTTTACTCTGATCCCTC; SEQ ID NO:97 and CAAGGGGCAGTGGTAGTAAGT; SEQ ID NO:98); exon (n+15) was amplified with primer pair 455/456 (GCTATCTCTGGGACCCTT; SEQ ID NO:99 and CCACGTGGGGCATAAAGTT; SEQ ID NO:100); and exon (n+21) was amplified with primer pair 467/468 (ATGGCTGCCGCAGTTCA; SEQ ID NO:101 and CAAGCAGACATCCACCAT; SEQ ID NO:102). PCR conditions were as follows: 94° C., 30 seconds; 50° C., 1 minute; and 72° C., 30 seconds for 35 cycles.

The denatured PCR products were analyzed by electrophoresis on MDE gels (FMC Corp., Pinebrook, N.J.) with and without glycerol at 4° C. for 4–5 hours. Gels were transferred to filter paper and exposed to X-ray film at 70° C. for 1 to 24 hours. Amplicons demonstrating SSCP band shifts were sequenced by the Nucleic Acid/Protein core facility of the Children's Hospital of Philadelphia using an ABI373A automated sequencer.

All journal article, reference, and patent citations provided above, in parentheses or otherwise, whether previously stated or not, are incorporated herein by reference.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A method of diagnosing Alagille Syndrome in an individual, comprising detecting an Alagille Syndrome disease-associated mutation within a JAGGED1 gene, wherein detection of said Alagille Syndrome disease-associated mutation is diagnostic of Alagille Syndrome.

2. The method of claim 1, wherein said JAGGED1 gene is a human JAGGED1 (hJAGGED1) gene.

3. The method of claim 2, wherein said disease-associated mutation produces a truncated hJAGGED1 gene product.

4. The method of claim 3, wherein said disease-associated mutation occurs within the hJAGGED1 nucleotide sequence SEQ ID NO:1 at a position selected from group consisting of nucleotides 1104–1105, nucleotide 3102, nucleotides 2531–2534 and nucleotide 2066.

5. The method of claim 1, wherein said disease-associated mutation is within a JAGGED1 coding sequence.

6. A method of diagnosing Alagille Syndrome in an individual, comprising detecting a mutation other than a gross cytogenetic deletion or a deletion having a size of a megabase or more, said mutation comprising a variation in a JAGGED1 locus, wherein detection of said mutation is diagnostic of Alagille Syndrome.

7. The method of claim 6, comprising polymerase chain reaction amplification of a sample from said individual.

8. The method of claim 6, wherein said detecting comprises gel electrophoresis.

9. The method of claim 6, or claim 7, wherein said detecting comprises heteroduplex mobility analysis.

10. The method of claim 6, wherein said detecting comprises single strand conformation polymorphism analysis.

11. The method of claim 6, wherein said detecting comprises automated sequencing.

12. The method of claim 6, wherein said detecting comprises a technique selected from the group consisting of allele-specific oligonucleotide hybridization, denaturing gradient gel electrophoresis and restriction fragment length polymorphism analysis.

13. The method of claim 6, wherein said detecting comprises fluorescence in situ hybridization.

14. The method of claim 13, wherein said fluorescence in situ hybridization is performed using a bacterial artificial chromosome (BAC) probe.

15. A method of diagnosing Alagille Syndrome in an individual, comprising (a) contacting a sample from said individual with a nucleic acid molecule consisting essentially of JAGGED1 sequence; and (b) detecting a mutation in JAGGED1,
    wherein the presence of said mutation in JAGGED1 is diagnostic of Alagille Syndrome.

16. The method of claim 15, wherein said nucleic acid molecule consists essentially of JAGGED1 coding sequence or a portion thereof.

17. The method of claim 16, wherein said nucleic acid molecule consists essentially of human JAGGED1 coding sequence or a portion thereof.

18. The method of claim 15 or 16, wherein said nucleic acid molecule is an allele-specific oligonucleotide.

19. A method of diagnosing Alagille Syndrome in an individual, comprising (a) contacting a sample from said individual with a nucleic acid molecule comprising a JAGGED1 sequence; and (b) detecting a mutation in JAGGED1 in said sample from said individual,
    wherein the presence of said mutation is diagnostic of Alagille Syndrome.

20. The method of claim 19, wherein said nucleic acid molecule comprises JAGGED1 coding sequence or a portion thereof.

21. The method of claim 19, wherein said detecting comprises fluorescence in situ hybridization.

22. The method of claim 21, wherein said fluorescence in situ hybridization is performed using a bacterial artificial chromosome (BAC) probe.

* * * * *

SEQUENCE LISTING (1) GENERAL INFORMATION:

(iii) NUMBER OF SEQUENCES: 110

(2) INFORMATION FOR SEQ ID NO: 1:

(i) SEQUENCE CHARACTERISTICS:
      (A) LENGTH: 5590 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 414..4068

(xi) SEQUENCE DESCRIPTION: SEQ ID NO: 1:

```
CTGGGGCCGG CCCGCGAGCT AGGCTGGGTT TTTTTTTTTC TCCCCTCCCT CCCCCCTTTT      60

TCCATGCAGC TGATCTAAAA GGGAATAAAA GGCTGCGCAT AATCATAATA ATAAAAGAAG     120

GGGAGCGCGA GAGAAGGAAA GAAAGCCGGG AGGTGGAAGA GGAGGGGGAG CGTCTCAAAG     180

AAGCGATCAG AATAATAAAA GGAGGCCGGG CTCTTTGCCT TCTGGAACGG GCCGCTCTTG     240

AAAGGGCTTT TGAAAAGTGG TGTTGTTTTC CAGTCGTGCA TGCTCCAATC GGCGGAGTAT     300

ATTAGAGCCG GGACGCGGCG GCCGCAGGGG CAGCGGCGAC GGCAGCACCG GCGGCAGCAC     360

CAGCGCGAAC AGCAGCGGCG GCGTCCCGAG TGCCCGCGGC GCGCGGCGCA GCG ATG        416
                                                          Met
                                                           1

CGT TCC CCA CGG ACG CGC GGC CGG TCC GGG CGC CCC CTA AGC CTC CTG      464
Arg Ser Pro Arg Thr Arg Gly Arg Ser Gly Arg Pro Leu Ser Leu Leu
           5                  10                  15

CTC GCC CTG CTC TGT GCC CTG CGA GCC AAG GTG TGT GGG GCC TCG GGT      512
Leu Ala Leu Leu Cys Ala Leu Arg Ala Lys Val Cys Gly Ala Ser Gly
         20                  25                  30

CAG TTC GAG TTG GAG ATC CTG TCC ATG CAG AAC GTG AAC GGG GAG CTG      560
Gln Phe Glu Leu Glu Ile Leu Ser Met Gln Asn Val Asn Gly Glu Leu
     35                  40                  45

CAG AAC GGG AAC TGC TGC GGC GGC GCC CGG AAC CCG GGA GAC CGC AAG      608
Gln Asn Gly Asn Cys Cys Gly Gly Ala Arg Asn Pro Gly Asp Arg Lys
 50                  55                  60                  65

TGC ACC CGC GAC GAG TGT GAC ACA TAC TTC AAA GTG TGC CTC AAG GAG      656
Cys Thr Arg Asp Glu Cys Asp Thr Tyr Phe Lys Val Cys Leu Lys Glu
                 70                  75                  80

TAT CAG TCC CGC GTC ACG GCC GGG GGG CCC TGC AGC TTC GGC TCA GGG      704
Tyr Gln Ser Arg Val Thr Ala Gly Gly Pro Cys Ser Phe Gly Ser Gly
             85                  90                  95

TCC ACG CCT GTC ATC GGG GGC AAC ACC TTC AAC CTC AAG GCC AGC CGC      752
Ser Thr Pro Val Ile Gly Gly Asn Thr Phe Asn Leu Lys Ala Ser Arg
        100                 105                 110

GGC AAC GAC CGC AAC CGC ATC GTG CTG CCT TTC AGT TTC GCC TGG CCG      800
Gly Asn Asp Arg Asn Arg Ile Val Leu Pro Phe Ser Phe Ala Trp Pro
    115                 120                 125

AGG TCC TAT ACG TTG CTT GTG GAG GCG TGG GAT TCC AGT AAT GAC ACC      848
Arg Ser Tyr Thr Leu Leu Val Glu Ala Trp Asp Ser Ser Asn Asp Thr
130                 135                 140                 145

GTT CAA CCT GAC AGT ATT ATT GAA AAG GCT TCT CAC TCG GGC ATG ATC      896
Val Gln Pro Asp Ser Ile Ile Glu Lys Ala Ser His Ser Gly Met Ile
                150                 155                 160
```

```
AAC CCC AGC CGG CAG TGG CAG ACG CTG AAG CAG AAC ACG GGC GTT GCC        944
Asn Pro Ser Arg Gln Trp Gln Thr Leu Lys Gln Asn Thr Gly Val Ala
            165                 170                 175

CAC TTT GAG TAT CAG ATC CGC GTG ACC TGT GAT GAC TAC TAC TAT GGC        992
His Phe Glu Tyr Gln Ile Arg Val Thr Cys Asp Asp Tyr Tyr Tyr Gly
            180                 185                 190

TTT GGC TGC AAT AAG TTC TGC CGC CCC AGA GAT GAC TTC TTT GGA CAC       1040
Phe Gly Cys Asn Lys Phe Cys Arg Pro Arg Asp Asp Phe Phe Gly His
195                 200                 205

TAT GCC TGT GAC CAG AAT GGC AAC AAA ACT TGC ATG GAA GGC TGG ATG       1088
Tyr Ala Cys Asp Gln Asn Gly Asn Lys Thr Cys Met Glu Gly Trp Met
210                 215                 220                 225

GGC CCC GAA TGT AAC AGA GCT ATT TGC CGA CAA GGC TGC AGT CCT AAG       1136
Gly Pro Glu Cys Asn Arg Ala Ile Cys Arg Gln Gly Cys Ser Pro Lys
            230                 235                 240

CAT GGG TCT TGC AAA CTC CCA GGT GAC TGC AGG TGC CAG TAT GGC TGG       1184
His Gly Ser Cys Lys Leu Pro Gly Asp Cys Arg Cys Gln Tyr Gly Trp
            245                 250                 255

CAA GGC CTG TAC TGT GAT AAG TGC ATC CCA CAC CCG GGA TGC GTC CAC       1232
Gln Gly Leu Tyr Cys Asp Lys Cys Ile Pro His Pro Gly Cys Val His
            260                 265                 270

GGC ATC TGT AAT GAG CCC TGG CAG TGC CTC TGT GAG ACC AAC TGG GGC       1280
Gly Ile Cys Asn Glu Pro Trp Gln Cys Leu Cys Glu Thr Asn Trp Gly
275                 280                 285

GGC CAG CTC TGT GAC AAA GAT CTC AAT TAC TGT GGG ACT CAT CAG CCG       1328
Gly Gln Leu Cys Asp Lys Asp Leu Asn Tyr Cys Gly Thr His Gln Pro
290                 295                 300                 305

TGT CTC AAC GGG GGA ACT TGT AGC AAC ACA GGC CCT GAC AAA TAT CAG       1376
Cys Leu Asn Gly Gly Thr Cys Ser Asn Thr Gly Pro Asp Lys Tyr Gln
            310                 315                 320

TGT TCC TGC CCT GAG GGG TAT TCA GGA CCC AAC TGT GAA ATT GCT GAG       1424
Cys Ser Cys Pro Glu Gly Tyr Ser Gly Pro Asn Cys Glu Ile Ala Glu
            325                 330                 335

CAC GCC TGC CTC TCT GAT CCC TGT CAC AAC AGA GGC AGC TGT AAG GAG       1472
His Ala Cys Leu Ser Asp Pro Cys His Asn Arg Gly Ser Cys Lys Glu
            340                 345                 350

ACC TCC CTG GGC TTT GAG TGT GAG TGT TCC CCA GGC TGG ACC GGC CCC       1520
Thr Ser Leu Gly Phe Glu Cys Glu Cys Ser Pro Gly Trp Thr Gly Pro
355                 360                 365

ACA TGC TCT ACA AAC ATT GAT GAC TGT TCT CCT AAT AAC TGT TCC CAC       1568
Thr Cys Ser Thr Asn Ile Asp Asp Cys Ser Pro Asn Asn Cys Ser His
370                 375                 380                 385

GGG GGC ACC TGC CAG GAC CTG GTT AAC GGA TTT AAG TGT GTG TGC CCC       1616
Gly Gly Thr Cys Gln Asp Leu Val Asn Gly Phe Lys Cys Val Cys Pro
            390                 395                 400

CCA CAG TGG ACT GGG AAA ACG TGC CAG TTA GAT GCA AAT GAA TGT GAG       1664
Pro Gln Trp Thr Gly Lys Thr Cys Gln Leu Asp Ala Asn Glu Cys Glu
            405                 410                 415

GCC AAA CCT TGT GTA AAC GCC AAA TCC TGT AAG AAT CTC ATT GCC AGC       1712
Ala Lys Pro Cys Val Asn Ala Lys Ser Cys Lys Asn Leu Ile Ala Ser
            420                 425                 430

TAC TAC TGC GAC TGT CTT CCC GGC TGG ATG GGT CAG AAT TGT GAC ATA       1760
Tyr Tyr Cys Asp Cys Leu Pro Gly Trp Met Gly Gln Asn Cys Asp Ile
            435                 440                 445

AAT ATT AAT GAC TGC CTT GGC CAG TGT CAG AAT GAC GCC TCC TGT CGG       1808
Asn Ile Asn Asp Cys Leu Gly Gln Cys Gln Asn Asp Ala Ser Cys Arg
450                 455                 460                 465

GAT TTG GTT AAT GGT TAT CGC TGT ATC TGT CCA CCT GGC TAT GCA GGC       1856
Asp Leu Val Asn Gly Tyr Arg Cys Ile Cys Pro Pro Gly Tyr Ala Gly
```

-continued

```
                470                 475                 480
GAT CAC TGT GAG AGA GAC ATC GAT GAA TGT GCC AGC AAC CCC TGT TTG         1904
Asp His Cys Glu Arg Asp Ile Asp Glu Cys Ala Ser Asn Pro Cys Leu
            485                 490                 495

AAT GGG GGT CAC TGT CAG AAT GAA ATC AAC AGA TTC CAG TGT CTG TGT         1952
Asn Gly Gly His Cys Gln Asn Glu Ile Asn Arg Phe Gln Cys Leu Cys
            500                 505                 510

CCC ACT GGT TTC TCT GGA AAC CTC TGT CAG CTG GAC ATC GAT TAT TGT         2000
Pro Thr Gly Phe Ser Gly Asn Leu Cys Gln Leu Asp Ile Asp Tyr Cys
            515                 520                 525

GAG CCT AAT CCC TGC CAG AAC GGT GCC CAG TGC TAC AAC CGT GCC AGT         2048
Glu Pro Asn Pro Cys Gln Asn Gly Ala Gln Cys Tyr Asn Arg Ala Ser
530                 535                 540                 545

GAC TAT TTC TGC AAG TGC CCC GAG GAC TAT GAG GGC AAG AAC TGC TCA         2096
Asp Tyr Phe Cys Lys Cys Pro Glu Asp Tyr Glu Gly Lys Asn Cys Ser
            550                 555                 560

CAC CTG AAA GAC CAC TGC CGC ACG ACC CCC TGT GAA GTG ATT GAC AGC         2144
His Leu Lys Asp His Cys Arg Thr Thr Pro Cys Glu Val Ile Asp Ser
            565                 570                 575

TGC ACA GTG GCC ATG GCT TCC AAC GAC ACA CCT GAA GGG GTG CGG TAT         2192
Cys Thr Val Ala Met Ala Ser Asn Asp Thr Pro Glu Gly Val Arg Tyr
            580                 585                 590

ATT TCC TCC AAC GTC TGT GGT CCT CAC GGG AAG TGC AAG AGT CAG TCG         2240
Ile Ser Ser Asn Val Cys Gly Pro His Gly Lys Cys Lys Ser Gln Ser
            595                 600                 605

GGA GGC AAA TTC ACC TGT GAC TGT AAC AAA GGC TTC ACG GGA ACA TAC         2288
Gly Gly Lys Phe Thr Cys Asp Cys Asn Lys Gly Phe Thr Gly Thr Tyr
610                 615                 620                 625

TGC CAT GAA AAT ATT AAT GAC TGT GAG AGC AAC CCT TGT AGA AAC GGT         2336
Cys His Glu Asn Ile Asn Asp Cys Glu Ser Asn Pro Cys Arg Asn Gly
            630                 635                 640

GGC ACT TGC ATC GAT GGT GTC AAC TCC TAC AAG TGC ATC TGT AGT GAC         2384
Gly Thr Cys Ile Asp Gly Val Asn Ser Tyr Lys Cys Ile Cys Ser Asp
            645                 650                 655

GGC TGG GAG GGG GCC TAC TGT GAA ACC AAT ATT AAT GAC TGC AGC CAG         2432
Gly Trp Glu Gly Ala Tyr Cys Glu Thr Asn Ile Asn Asp Cys Ser Gln
            660                 665                 670

AAC CCC TGC CAC AAT GGG GGC ACG TGT CGC GAC CTG GTC AAT GAC TTC         2480
Asn Pro Cys His Asn Gly Gly Thr Cys Arg Asp Leu Val Asn Asp Phe
            675                 680                 685

TAC TGT GAC TGT AAA AAT GGG TGG AAA GGA AAG ACC TGC CAC TCA CGT         2528
Tyr Cys Asp Cys Lys Asn Gly Trp Lys Gly Lys Thr Cys His Ser Arg
690                 695                 700                 705

GAC AGT CAG TGT GAT GAG GCC ACG TGC AAC AAC GGT GGC ACC TGC TAT         2576
Asp Ser Gln Cys Asp Glu Ala Thr Cys Asn Asn Gly Gly Thr Cys Tyr
            710                 715                 720

GAT GAG GGG GAT GCT TTT AAG TGC ATG TGT CCT GGC GGC TGG GAA GGA         2624
Asp Glu Gly Asp Ala Phe Lys Cys Met Cys Pro Gly Gly Trp Glu Gly
            725                 730                 735

ACA ACC TGT AAC ATA GCC CGA AAC AGT AGC TGC CTG CCC AAC CCC TGC         2672
Thr Thr Cys Asn Ile Ala Arg Asn Ser Ser Cys Leu Pro Asn Pro Cys
            740                 745                 750

CAT AAT GGG GGC ACA TGT GTG GTC AAC GGC GAG TCC TTT ACG TGC GTC         2720
His Asn Gly Gly Thr Cys Val Val Asn Gly Glu Ser Phe Thr Cys Val
            755                 760                 765

TGC AAG GAA GGC TGG GAG GGG CCC ATC TGT GCT CAG AAT ACC AAT GAC         2768
Cys Lys Glu Gly Trp Glu Gly Pro Ile Cys Ala Gln Asn Thr Asn Asp
770                 775                 780                 785

TGC AGC CCT CAT CCC TGT TAC AAC AGC GGC ACC TGT GTG GAT GGA GAC         2816
```

-continued

```
                Cys Ser Pro His Pro Cys Tyr Asn Ser Gly Thr Cys Val Asp Gly Asp
                            790                 795                 800

AAC TGG TAC CGG TGC GAA TGT GCC CCG GGT TTT GCT GGG CCC GAC TGC            2864
Asn Trp Tyr Arg Cys Glu Cys Ala Pro Gly Phe Ala Gly Pro Asp Cys
            805                 810                 815

AGA ATA AAC ATC AAT GAA TGC CAG TCT TCA CCT TGT GCC TTT GGA GCG            2912
Arg Ile Asn Ile Asn Glu Cys Gln Ser Ser Pro Cys Ala Phe Gly Ala
            820                 825                 830

ACC TGT GTG GAT GAG ATC AAT GGC TAC CGG TGT GTC TGC CCT CCA GGG            2960
Thr Cys Val Asp Glu Ile Asn Gly Tyr Arg Cys Val Cys Pro Pro Gly
            835                 840                 845

CAC AGT GGT GCC AAG TGC CAG GAA GTT TCA GGG AGA CCT TGC ATC ACC            3008
His Ser Gly Ala Lys Cys Gln Glu Val Ser Gly Arg Pro Cys Ile Thr
850                 855                 860                 865

ATG GGG AGT GTG ATA CCA GAT GGG GCC AAA TGG GAT GAT GAC TGT AAT            3056
Met Gly Ser Val Ile Pro Asp Gly Ala Lys Trp Asp Asp Asp Cys Asn
            870                 875                 880

ACC TGC CAG TGC CTG AAT GGA CGG ATC GCC TGC TCA AAG GTC TGG TGT            3104
Thr Cys Gln Cys Leu Asn Gly Arg Ile Ala Cys Ser Lys Val Trp Cys
            885                 890                 895

GGC CCT CGA CCT TGC CTG CTC CAC AAA GGG CAC AGC GAG TGC CCC AGC            3152
Gly Pro Arg Pro Cys Leu Leu His Lys Gly His Ser Glu Cys Pro Ser
            900                 905                 910

GGG CAG AGC TGC ATC CCC ATC CTG GAC GAC CAG TGC TTC GTC CAC CCC            3200
Gly Gln Ser Cys Ile Pro Ile Leu Asp Asp Gln Cys Phe Val His Pro
            915                 920                 925

TGC ACT GGT GTG GGC GAG TGT CGG TCT TCC AGT CTC CAG CCG GTG AAG            3248
Cys Thr Gly Val Gly Glu Cys Arg Ser Ser Ser Leu Gln Pro Val Lys
930                 935                 940                 945

ACA AAG TGC ACC TCT GAC TCC TAT TAC CAG GAT AAC TGT GCG AAC ATC            3296
Thr Lys Cys Thr Ser Asp Ser Tyr Tyr Gln Asp Asn Cys Ala Asn Ile
            950                 955                 960

ACA TTT ACC TTT AAC AAG GAG ATG ATG TCA CCA GGT CTT ACT ACG GAG            3344
Thr Phe Thr Phe Asn Lys Glu Met Met Ser Pro Gly Leu Thr Thr Glu
            965                 970                 975

CAC ATT TGC AGT GAA TTG AGG AAT TTG AAT ATT TTG AAG AAT GTT TCC            3392
His Ile Cys Ser Glu Leu Arg Asn Leu Asn Ile Leu Lys Asn Val Ser
            980                 985                 990

GCT GAA TAT TCA ATC TAC ATC GCT TGC GAG CCT TCC CCT TCA GCG AAC            3440
Ala Glu Tyr Ser Ile Tyr Ile Ala Cys Glu Pro Ser Pro Ser Ala Asn
            995                 1000                1005

AAT GAA ATA CAT GTG GCC ATT TCT GCT GAA GAT ATA CGG GAT GAT GGG            3488
Asn Glu Ile His Val Ala Ile Ser Ala Glu Asp Ile Arg Asp Asp Gly
1010                1015                1020                1025

AAC CCG ATC AAG GAA ATC ACT GAC AAA ATA ATC GAT CTT GTT AGT AAA            3536
Asn Pro Ile Lys Glu Ile Thr Asp Lys Ile Ile Asp Leu Val Ser Lys
            1030                1035                1040

CGT GAT GGA AAC AGC TCG CTG ATT GCT GCC GTT GCA GAA GTA AGA GTT            3584
Arg Asp Gly Asn Ser Ser Leu Ile Ala Ala Val Ala Glu Val Arg Val
            1045                1050                1055

CAG AGG CGG CCT CTG AAG AAC AGA ACA GAT TTC CTT GTT CCC TTG CTG            3632
Gln Arg Arg Pro Leu Lys Asn Arg Thr Asp Phe Leu Val Pro Leu Leu
            1060                1065                1070

AGC TCT GTC TTA ACT GTG GCT TGG ATC TGT TGC TTG GTG ACG GCC TTC            3680
Ser Ser Val Leu Thr Val Ala Trp Ile Cys Cys Leu Val Thr Ala Phe
            1075                1080                1085

TAC TGG TGC CTG CGG AAG CGG CGG AAG CCG GGC AGC CAC ACA CAC TCA            3728
Tyr Trp Cys Leu Arg Lys Arg Arg Lys Pro Gly Ser His Thr His Ser
1090                1095                1100                1105
```

| | |
|---|---|
| GCC TCT GAG GAC AAC ACC ACC AAC AAC GTG CGG GAG CAG CTG AAC CAG<br>Ala Ser Glu Asp Asn Thr Thr Asn Asn Val Arg Glu Gln Leu Asn Gln<br>           1110                        1115                    1120 | 3776 |
| ATC AAA AAC CCC ATT GAG AAA CAT GGG GCC AAC ACG GTC CCC ATC AAG<br>Ile Lys Asn Pro Ile Glu Lys His Gly Ala Asn Thr Val Pro Ile Lys<br>           1125                        1130                    1135 | 3824 |
| GAT TAC GAG AAC AAG AAC TCC AAA ATG TCT AAA ATA AGG ACA CAC AAT<br>Asp Tyr Glu Asn Lys Asn Ser Lys Met Ser Lys Ile Arg Thr His Asn<br>           1140                        1145                    1150 | 3872 |
| TCT GAA GTA GAA GAG GAC GAC ATG GAC AAA CAC CAG CAG AAA GCC CGG<br>Ser Glu Val Glu Glu Asp Asp Met Asp Lys His Gln Gln Lys Ala Arg<br>           1155                        1160                    1165 | 3920 |
| TTT GCC AAG CAG CCG GCG TAT ACG CTG GTA GAC AGA GAA GAG AAG CCC<br>Phe Ala Lys Gln Pro Ala Tyr Thr Leu Val Asp Arg Glu Glu Lys Pro<br>1170                    1175                    1180                    1185 | 3968 |
| CCC AAC GGC ACG CCG ACA AAA CAC CCA AAC TGG ACA AAC AAA CAG GAC<br>Pro Asn Gly Thr Pro Thr Lys His Pro Asn Trp Thr Asn Lys Gln Asp<br>           1190                        1195                    1200 | 4016 |
| AAC AGA GAC TTG GAA AGT GCC CAG AGC TTA AAC CGA ATG GAG TAC ATC<br>Asn Arg Asp Leu Glu Ser Ala Gln Ser Leu Asn Arg Met Glu Tyr Ile<br>           1205                        1210                    1215 | 4064 |
| GTA T AGCAGACCGC GGGCACTGCC GCCGCTAGGT AGAGTCTGAG GGCTTGTAGT<br>Val | 4118 |
| TCTTTAAACT GTCGTGTCAT ACTCGAGTCT GAGGCCGTTG CTGACTTAGA ATCCCTGTGT | 4178 |
| TAATTTAAGT TTTGACAAGC TGGCTTACAC TGGCAATGAC AGTTTCTGTG GTTGGCTGGG | 4238 |
| AAATCGAGTG CCGCATCTCA CAGCTATGCA AAAAGCTAGT CAACAGTACC CTGGTTGTGT | 4298 |
| GTCCCCTTGC AGCCGACACG GTCTCGGATC AGGCTCCCAG GAGCCTGCCC AGCCCCTGG | 4358 |
| TCTTTGAGCT CCCACTTCTG CCAGATGTCC TAATGGTGAT GCAGTCTTAG ATCATAGTTT | 4418 |
| TATTTATATT TATTGACTCT TGAGTTGTTT TTGTATATTG GTTTTATGAT GACGTACAAG | 4478 |
| TAGTTCTGTA TTTGAAAGTG CCTTTGCAGC TCAGAACCAC AGCAACGATC ACAAATGACT | 4538 |
| TTATTATTTA TTTTTTTAAT TGTATTTTTG TTGTTGGGGG AGGGGAGACT TTGATGTCAG | 4598 |
| CAGTTGCTGG TAAAATGAAG AATTTAAAGA AAAAAATGTC AAAAGTAGAA CTTTGTATAG | 4658 |
| TTATGTAAAT AATTCTTTTT TATTAATCAC TGTGTATATT TGATTATTA ACTAATAAT | 4718 |
| CAAGAGCCTT AAAACATCAT TCCTTTTTAT TTATATGTAT GTGTTTAGAA TTGAAGGTTT | 4778 |
| TTGATAGCAT TGTAAGCGTA TGGCTTTATT TTTTTGAACT CTTCTCATTA CTTGTTGCCT | 4838 |
| ATAAGCCAAA ATTAAGGTGT TTGAAAATAG TTTATTTTAA AACAATAGGA TGGGCTTCTG | 4898 |
| TGCCCAGAAT ACTGATGGAA TTTTTTTTGT ACGACGTCAG ATGTTTAAAA CACCTTCTAT | 4958 |
| AGCATCACTT AAAACACGTT TTAAGGACTG ACTGAGGCAG TTTGAGGATT AGTTTAGAAC | 5018 |
| AGGTTTTTTT GTTTGTTTGT TTTTTGTTTT TCTGCTTTAG ACTTGAAAAG AGACAGGCAG | 5078 |
| GTGATCTGCT GCAGAGCAGT AAGGGAACAA GTTGAGCTAT GACTTAACAT AGCCAAAATG | 5138 |
| TGAGTGGTTG AATATGATTA AAAATATCAA ATTAATTGTG TGAACTTGGA AGCACACCAA | 5198 |
| TCTGACTTTG TAAATTCTGA TTTCTTTTCA CCATTCGTAC ATAATACTGA ACCACTTGTA | 5258 |
| GATTTGATTT TTTTTTTAAT CTACTGCATT TAGGGAGTAT TCTAATAAGC TAGTTGAATA | 5318 |
| CTTGAACCAT AAAATGTCCA GTAAGATCAC TGTTTAGATT TGCCATAGAG TACACTGCCT | 5378 |
| GCCTTAAGTG AGGAAATCAA AGTGCTATTA CGAAGTTCAA GATCAAAAAG GCTTATAAAA | 5438 |
| CAGAGTAATC TTGTTGGTTC ACCATTGAGA CCGTGAAGAT ACTTTGTATT GTCCTATTAG | 5498 |
| TGTTATATGA ACATACAAAT GCATCTTTGA TGTGTTGTTC TTGGCAATAA ATTTTGAAAA | 5558 |

GTAATATTTA TTAAATTTTT TTGTATGAAA AC            5590

(2) INFORMATION FOR SEQ ID NO: 2:

(i) SEQUENCE CHARACTERISTICS:
        (A) LENGTH: 1218 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Arg Ser Pro Arg Thr Arg Gly Arg Ser Gly Arg Pro Leu Ser Leu
 1               5                  10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350
```

```
Glu Thr Ser Leu Gly Phe Glu Cys Glu Cys Ser Pro Gly Trp Thr Gly
            355                 360                 365

Pro Thr Cys Ser Thr Asn Ile Asp Asp Cys Ser Pro Asn Asn Cys Ser
    370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Lys Ser Cys Lys Asn Leu Ile Ala
            420                 425                 430

Ser Tyr Tyr Cys Asp Cys Leu Pro Gly Trp Met Gly Gln Asn Cys Asp
        435                 440                 445

Ile Asn Ile Asn Asp Cys Leu Gly Gln Cys Gln Asn Asp Ala Ser Cys
        450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525

Cys Glu Pro Asn Pro Cys Gln Asn Gly Ala Gln Cys Tyr Asn Arg Ala
        530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
        595                 600                 605

Ser Gly Gly Lys Phe Thr Cys Asp Cys Asn Lys Gly Phe Thr Gly Thr
    610                 615                 620

Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala Tyr Cys Glu Thr Asn Ile Asn Asp Cys Ser
            660                 665                 670

Gln Asn Pro Cys His Asn Gly Gly Thr Cys Arg Asp Leu Val Asn Asp
        675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Glu Ser Phe Thr Cys
        755                 760                 765
```

-continued

| | | | | | | | | | | | |
|---|---|---|---|---|---|---|---|---|---|---|---|
| Val | Cys | Lys | Glu | Gly | Trp | Glu | Gly | Pro | Ile | Cys | Ala | Gln | Asn | Thr | Asn |
| 770 | | | | | 775 | | | | 780 | | |

Val Cys Lys Glu Gly Trp Glu Gly Pro Ile Cys Ala Gln Asn Thr Asn
770                     775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                    805                 810                 815

Cys Arg Ile Asn Ile Asn Glu Cys Gln Ser Ser Pro Cys Ala Phe Gly
                820                 825                 830

Ala Thr Cys Val Asp Glu Ile Asn Gly Tyr Arg Cys Val Cys Pro Pro
            835                 840                 845

Gly His Ser Gly Ala Lys Cys Gln Glu Val Ser Gly Arg Pro Cys Ile
        850                 855                 860

Thr Met Gly Ser Val Ile Pro Asp Gly Ala Lys Trp Asp Asp Asp Cys
865                 870                 875                 880

Asn Thr Cys Gln Cys Leu Asn Gly Arg Ile Ala Cys Ser Lys Val Trp
                885                 890                 895

Cys Gly Pro Arg Pro Cys Leu Leu His Lys Gly His Ser Glu Cys Pro
            900                 905                 910

Ser Gly Gln Ser Cys Ile Pro Ile Leu Asp Asp Gln Cys Phe Val His
        915                 920                 925

Pro Cys Thr Gly Val Gly Glu Cys Arg Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile Ala Cys Glu Pro Ser Pro Ser Ala
        995                 1000                1005

Asn Asn Glu Ile His Val Ala Ile Ser Ala Glu Asp Ile Arg Asp Asp
    1010                1015                1020

Gly Asn Pro Ile Lys Glu Ile Thr Asp Lys Ile Ile Asp Leu Val Ser
1025                1030                1035                1040

Lys Arg Asp Gly Asn Ser Ser Leu Ile Ala Ala Val Ala Glu Val Arg
                1045                1050                1055

Val Gln Arg Arg Pro Leu Lys Asn Arg Thr Asp Phe Leu Val Pro Leu
            1060                1065                1070

Leu Ser Ser Val Leu Thr Val Ala Trp Ile Cys Cys Leu Val Thr Ala
        1075                1080                1085

Phe Tyr Trp Cys Leu Arg Lys Arg Arg Lys Pro Gly Ser His Thr His
    1090                1095                1100

Ser Ala Ser Glu Asp Asn Thr Thr Asn Asn Val Arg Glu Gln Leu Asn
1105                1110                1115                1120

Gln Ile Lys Asn Pro Ile Glu Lys His Gly Ala Asn Thr Val Pro Ile
                1125                1130                1135

Lys Asp Tyr Glu Asn Lys Asn Ser Lys Met Ser Lys Ile Arg Thr His
            1140                1145                1150

Asn Ser Glu Val Glu Glu Asp Asp Met Asp Lys His Gln Gln Lys Ala
        1155                1160                1165

Arg Phe Ala Lys Gln Pro Ala Tyr Thr Leu Val Asp Arg Glu Glu Lys
    1170                1175                1180

Pro Pro Asn Gly Thr Pro Thr Lys His Pro Asn Trp Thr Asn Lys Gln

```
1185                1190                1195                1200
Asp Asn Arg Asp Leu Glu Ser Ala Gln Ser Leu Asn Arg Met Glu Tyr
                1205                1210                1215
Ile Val (2) INFORMATION FOR SEQ ID NO: 3:

(i) SEQUENCE CHARACTERISTICS:
        (A) LENGTH: 4315 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 16..3460

(xi) SEQUENCE DESCRIPTION: SEQ ID NO: 3:

CGGCCGCGTC GACGT GAC GGC GAC GGC CGG ACA ACG CGC GCG GGG GGC TGC        51
              Asp Gly Asp Gly Arg Thr Thr Arg Ala Gly Gly Cys
                1               5                   10

GGC CAC GAC GAG TGC GAC ACG TAC GTG CGC GTG TGC CTT AAG GAG TAC         99
Gly His Asp Glu Cys Asp Thr Tyr Val Arg Val Cys Leu Lys Glu Tyr
            15                  20                  25

CAG GCC AAG GTG ACG CCC ACG GGG CCC TGC AGC TAC GGC CAC GGC GCC        147
Gln Ala Lys Val Thr Pro Thr Gly Pro Cys Ser Tyr Gly His Gly Ala
    30                  35                  40

ACG CCC GTG CTG GGC GGC AAC TCC TTC TAC CTG CCG CCG GCG GGC GCT        195
Thr Pro Val Leu Gly Gly Asn Ser Phe Tyr Leu Pro Pro Ala Gly Ala
45                  50                  55                  60

GCG GGG GAC CGA GCG CGG GCG CGG GCC CGG GCC GGC GGC GAC CAG GAC        243
Ala Gly Asp Arg Ala Arg Ala Arg Ala Arg Ala Gly Gly Asp Gln Asp
                65                  70                  75

CCG GGC CTC GTC GTC ATC CCC TTC CAG TTC GCC TGG CCG CGC TCC TTT        291
Pro Gly Leu Val Val Ile Pro Phe Gln Phe Ala Trp Pro Arg Ser Phe
            80                  85                  90

ACC CTC ATC GTG GAG GCC TGG GAC TGG GAC AAC GAT ACC ACC CCG AAT        339
Thr Leu Ile Val Glu Ala Trp Asp Trp Asp Asn Asp Thr Thr Pro Asn
                95                  100                 105

GAG GAG CTG CTG ATC GAG CGA GTG TCG CAT GCC GGC ATG ATC AAC CCG        387
Glu Glu Leu Leu Ile Glu Arg Val Ser His Ala Gly Met Ile Asn Pro
110                 115                 120

GAG GAC CGC TGG AAG AGC CTG CAC TTC AGC GGC CAC GTG GCG CAC CTG        435
Glu Asp Arg Trp Lys Ser Leu His Phe Ser Gly His Val Ala His Leu
125                 130                 135                 140

GAG CTG CAG ATC CGC GTG CGC TGC GAC GAG AAC TAC TAC AGC GCC ACT        483
Glu Leu Gln Ile Arg Val Arg Cys Asp Glu Asn Tyr Tyr Ser Ala Thr
                145                 150                 155

TGC AAC AAG TTC TGC CGG CCC CGC AAC GAC TTT TTC GGC CAC TAC ACC        531
Cys Asn Lys Phe Cys Arg Pro Arg Asn Asp Phe Phe Gly His Tyr Thr
                160                 165                 170

TGC GAC CAG TAC GGC AAC AAG GCC TGC ATG GAC GGC TGG ATG GGC AAG        579
Cys Asp Gln Tyr Gly Asn Lys Ala Cys Met Asp Gly Trp Met Gly Lys
            175                 180                 185

GAG TGC AAG GAA GCT GTG TGT AAA CAA GGG TGT AAT TTG CTC CAC GGG        627
Glu Cys Lys Glu Ala Val Cys Lys Gln Gly Cys Asn Leu Leu His Gly
            190                 195                 200

GGA TGC ACC GTG CCT GGG GAG TGC AGG TGC AGC TAC GGC TGG CAA GGG        675
Gly Cys Thr Val Pro Gly Glu Cys Arg Cys Ser Tyr Gly Trp Gln Gly
205                 210                 215                 220

AGG TTC TGC GAT GAG TGT GTC CCC TAC CCC GGC TGC GTG CAT GGC AGT        723
```

```
                Arg Phe Cys Asp Glu Cys Val Pro Tyr Pro Gly Cys Val His Gly Ser
                                225                 230                 235

TGT GTG GAG CCC TGG CAG TGC AAC TGT GAG ACC AAC TGG GGC GGC CTG             771
Cys Val Glu Pro Trp Gln Cys Asn Cys Glu Thr Asn Trp Gly Gly Leu
            240                 245                 250

CTC TGT GAC AAA GAC CTG AAC TAC TGT GGC AGC CAC CAC CCC TGC ACC             819
Leu Cys Asp Lys Asp Leu Asn Tyr Cys Gly Ser His His Pro Cys Thr
            255                 260                 265

AAC GGA GGC ACG TGC ATC AAC GCC GAG CCT GAC CAG TAC CGC TGC ACC             867
Asn Gly Gly Thr Cys Ile Asn Ala Glu Pro Asp Gln Tyr Arg Cys Thr
        270                 275                 280

TGC CCT GAC GGC TAC TCG GGC AGG AAC TGT GAG AAG GCT GAG CAC GCC             915
Cys Pro Asp Gly Tyr Ser Gly Arg Asn Cys Glu Lys Ala Glu His Ala
285                 290                 295                 300

TGC ACC TCC AAC CCG TGT GCC AAC GGG GGC TCT TGC CAT GAG GTG CCG             963
Cys Thr Ser Asn Pro Cys Ala Asn Gly Gly Ser Cys His Glu Val Pro
                305                 310                 315

TCC GGC TTC GAA TGC CAC TGC CCA TCG GGC TGG AGC GGG CCC ACC TGT            1011
Ser Gly Phe Glu Cys His Cys Pro Ser Gly Trp Ser Gly Pro Thr Cys
                320                 325                 330

GCC CTT GAC ATC GAT GAG TGT GCT TCG AAC CCG TGT GCG GCC GGT GGC            1059
Ala Leu Asp Ile Asp Glu Cys Ala Ser Asn Pro Cys Ala Ala Gly Gly
            335                 340                 345

ACC TGT GTG GAC CAG GTG GAC GGC TTT GAG TGC ATC TGC CCC GAG CAG            1107
Thr Cys Val Asp Gln Val Asp Gly Phe Glu Cys Ile Cys Pro Glu Gln
        350                 355                 360

TGG GTG GGG GCC ACC TGC CAG CTG GAC GTC AAC GAC TGT CGC GGG CAG            1155
Trp Val Gly Ala Thr Cys Gln Leu Asp Val Asn Asp Cys Arg Gly Gln
365                 370                 375                 380

TGT CAG CAT GGG GGC ACC TGC AAG GAC CTG GTG AAC GGG TAC CAG TGT            1203
Cys Gln His Gly Gly Thr Cys Lys Asp Leu Val Asn Gly Tyr Gln Cys
                385                 390                 395

GTG TGC CCA CGG GGC TTC GGA GGC CGG CAT TGC GAG CTG GAA CGA GAC            1251
Val Cys Pro Arg Gly Phe Gly Gly Arg His Cys Glu Leu Glu Arg Asp
                400                 405                 410

AAG TGT GCC AGC AGC CCC TGC CAC AGC GGC GGC CTC TGC GAG GAC CTG            1299
Lys Cys Ala Ser Ser Pro Cys His Ser Gly Gly Leu Cys Glu Asp Leu
            415                 420                 425

GCC GAC GGC TTC CAC TGC CAC TGC CCC CAG GGC TTC TCC GGG CCT CTC            1347
Ala Asp Gly Phe His Cys His Cys Pro Gln Gly Phe Ser Gly Pro Leu
        430                 435                 440

TGT GAG GTG GAT GTC GAC CTT TGT GAG CCA AGC CCC TGC CGG AAC GGC            1395
Cys Glu Val Asp Val Asp Leu Cys Glu Pro Ser Pro Cys Arg Asn Gly
445                 450                 455                 460

GCT CGC TGC TAT AAC CTG GAG GGT GAC TAT TAC TGC GCC TGC CCT GAT            1443
Ala Arg Cys Tyr Asn Leu Glu Gly Asp Tyr Tyr Cys Ala Cys Pro Asp
                465                 470                 475

GAC TTT GGT GGC AAG AAC TGC TCC GTG CCC CGC GAG CCG TGC TGG CGG            1491
Asp Phe Gly Gly Lys Asn Cys Ser Val Pro Arg Glu Pro Cys Trp Arg
            480                 485                 490

GGC CTG CAG AGT GAT CGA TGG CTG CGG GTC AGA CGC GGG GCC TGG GAT            1539
Gly Leu Gln Ser Asp Arg Trp Leu Arg Val Arg Arg Gly Ala Trp Asp
        495                 500                 505

GCC TGG CAC AGC ACG TCC GGC GTG TGT GGC CCC CAT GGA CGC TGC GTC            1587
Ala Trp His Ser Thr Ser Gly Val Cys Gly Pro His Gly Arg Cys Val
    510                 515                 520

AGC CAG CCA GGG GGC AAC TTT TCC TGC ATC TGT GAC AGT GGC TTT ACT            1635
Ser Gln Pro Gly Gly Asn Phe Ser Cys Ile Cys Asp Ser Gly Phe Thr
525                 530                 535                 540
```

-continued

```
GGC ACC TAC TGC CAT GAG AAC ATT GAC GAC TGC CTG GGC CAG CCC TGC      1683
Gly Thr Tyr Cys His Glu Asn Ile Asp Asp Cys Leu Gly Gln Pro Cys
            545                 550                 555

CGC AAT GGG GGC ACA TGC ATC GAT GAG GTG GAC GCC TTC CGC TGC TTC      1731
Arg Asn Gly Gly Thr Cys Ile Asp Glu Val Asp Ala Phe Arg Cys Phe
                560                 565                 570

TGC CCC AGC GGC TGG GAG GGC GAG CTC TGC GAC ACC AAT CCC AAC GAC      1779
Cys Pro Ser Gly Trp Glu Gly Glu Leu Cys Asp Thr Asn Pro Asn Asp
            575                 580                 585

TGC CTT CCC GAT CCC TGC CAC AGC CGC GGC CGC TGC TAC GAC CTG GTC      1827
Cys Leu Pro Asp Pro Cys His Ser Arg Gly Arg Cys Tyr Asp Leu Val
            590                 595                 600

AAT GAC TTC TAC TGT GCG TGC GAC GAC GGC TGG AAG GGC AAG ACC TGC      1875
Asn Asp Phe Tyr Cys Ala Cys Asp Asp Gly Trp Lys Gly Lys Thr Cys
605                 610                 615                 620

CAC TCA CGC GAG TTC CAG TGC GAT GCC TAC ACC TGC AGC AAC GGT GGC      1923
His Ser Arg Glu Phe Gln Cys Asp Ala Tyr Thr Cys Ser Asn Gly Gly
                625                 630                 635

ACC TGC TAC GAC AGC GGC GAC ACC TTC CGC TGC GCC TGC CCC CCC GGC      1971
Thr Cys Tyr Asp Ser Gly Asp Thr Phe Arg Cys Ala Cys Pro Pro Gly
            640                 645                 650

TGG AAG GGC AGC ACC TGC GCC GTC GCC AAG AAC AGC AGC TGC CTG CCC      2019
Trp Lys Gly Ser Thr Cys Ala Val Ala Lys Asn Ser Ser Cys Leu Pro
            655                 660                 665

AAC CCC TGT GTG AAT GGT GGC ACC TGC GTG GGC AGC GGG GCC TCC TTC      2067
Asn Pro Cys Val Asn Gly Gly Thr Cys Val Gly Ser Gly Ala Ser Phe
670                 675                 680

TCC TGC ATC TGC CGG GAC GGC TGG GAG GGT CGT ACT TGC ACT CAC AAT      2115
Ser Cys Ile Cys Arg Asp Gly Trp Glu Gly Arg Thr Cys Thr His Asn
685                 690                 695                 700

ACC AAC GAC TGC AAC CCT CTG CCT TGC TAC AAT GGT GGC ATC TGT GTT      2163
Thr Asn Asp Cys Asn Pro Leu Pro Cys Tyr Asn Gly Gly Ile Cys Val
                705                 710                 715

GAC GGC GTC AAC TGG TTC CGC TGC GAG TGT GCA CCT GGC TTC GCG GGG      2211
Asp Gly Val Asn Trp Phe Arg Cys Glu Cys Ala Pro Gly Phe Ala Gly
            720                 725                 730

CCT GAC TGC CGC ATC AAC ATC GAC GAG TGC CAG TCC TCG CCC TGT GCC      2259
Pro Asp Cys Arg Ile Asn Ile Asp Glu Cys Gln Ser Ser Pro Cys Ala
            735                 740                 745

TAC GGG GCC ACG TGT GTG GAT GAG ATC AAC GGG TAT CGC TGT AGC TGC      2307
Tyr Gly Ala Thr Cys Val Asp Glu Ile Asn Gly Tyr Arg Cys Ser Cys
750                 755                 760

CCA CCC GGC CGA GCC GGC CCC CGG TGC CAG GAA GTG ATC GGG TTC GGG      2355
Pro Pro Gly Arg Ala Gly Pro Arg Cys Gln Glu Val Ile Gly Phe Gly
765                 770                 775                 780

AGA TCC TGC TGG TCC CGG GGC ACT CCG TTC CCA CAC GGA AGC TCC TGG      2403
Arg Ser Cys Trp Ser Arg Gly Thr Pro Phe Pro His Gly Ser Ser Trp
                785                 790                 795

GTG GAA GAC TGC AAC AGC TGC CGC TGC CTG GAT GGC CGC CGT GAC TGC      2451
Val Glu Asp Cys Asn Ser Cys Arg Cys Leu Asp Gly Arg Arg Asp Cys
            800                 805                 810

AGC AAG GTG TGG TGC GGA TGG AAG CCT TGT CTG CTG GCC GGC CAG CCC      2499
Ser Lys Val Trp Cys Gly Trp Lys Pro Cys Leu Leu Ala Gly Gln Pro
            815                 820                 825

GAG GCC CTG AGC GCC CAG TGC CCA CTG GGG CAA AGG TGC CTG GAG AAG      2547
Glu Ala Leu Ser Ala Gln Cys Pro Leu Gly Gln Arg Cys Leu Glu Lys
            830                 835                 840

GCC CCA GGC CAG TGT CTG CGA CCA CCC TGT GAG GCC TGG GGG GAG TGC      2595
Ala Pro Gly Gln Cys Leu Arg Pro Pro Cys Glu Ala Trp Gly Glu Cys
845                 850                 855                 860
```

```
GGC GCA GAA GAG CCA CCG AGC ACC CCC TGC CTG CCA CGC TCC GGC CAC    2643
Gly Ala Glu Glu Pro Pro Ser Thr Pro Cys Leu Pro Arg Ser Gly His
                865                 870                 875

CTG GAC AAT AAC TGT GCC CGC CTC ACC TTG CAT TTC AAC CGT GAC CAC    2691
Leu Asp Asn Asn Cys Ala Arg Leu Thr Leu His Phe Asn Arg Asp His
                880                 885                 890

GTG CCC CAG GGC ACC ACG GTG GGC GCC ATT TGC TCC GGG ATC CGC TCC    2739
Val Pro Gln Gly Thr Thr Val Gly Ala Ile Cys Ser Gly Ile Arg Ser
                895                 900                 905

CTG CCA GCC ACA AGG GCT GTG GCA CGG GAC CGC CTG CTG GTG TTG CTT    2787
Leu Pro Ala Thr Arg Ala Val Ala Arg Asp Arg Leu Leu Val Leu Leu
                910                 915                 920

TGC GAC CGG GCG TCC TCG GGG GCC AGT GCC GTG GAG GTG GCC GTG TCC    2835
Cys Asp Arg Ala Ser Ser Gly Ala Ser Ala Val Glu Val Ala Val Ser
925                 930                 935                 940

TTC AGC CCT GCC AGG GAC CTG CCT GAC AGC AGC CTG ATC CAG GGC GCG    2883
Phe Ser Pro Ala Arg Asp Leu Pro Asp Ser Ser Leu Ile Gln Gly Ala
                945                 950                 955

GCC CAC GCC ATC GTG GCC GCC ATC ACC CAG CGG GGG AAC AGC TCA CTG    2931
Ala His Ala Ile Val Ala Ala Ile Thr Gln Arg Gly Asn Ser Ser Leu
                960                 965                 970

CTC CTG GCT GTC ACC GAG GTC AAG GTG GAG ACG GTT GTT ACG GGC GGC    2979
Leu Leu Ala Val Thr Glu Val Lys Val Glu Thr Val Val Thr Gly Gly
                975                 980                 985

TCT TCC ACA GGT CTG CTG GTG CCT GTG CTG TGT GGT GCC TTC AGC GTG    3027
Ser Ser Thr Gly Leu Leu Val Pro Val Leu Cys Gly Ala Phe Ser Val
                990                 995                 1000

CTG TGG CTG GCG TGC GTG GTC CTG TGC GTG TGG TGG ACA CGC AAG CGC    3075
Leu Trp Leu Ala Cys Val Val Leu Cys Val Trp Trp Thr Arg Lys Arg
1005                1010                1015                1020

AGG AAA GAG CGG GAG AGG AGC CGG CTG CCG CGG GAG GAG AGC GCC AAC    3123
Arg Lys Glu Arg Glu Arg Ser Arg Leu Pro Arg Glu Glu Ser Ala Asn
                1025                1030                1035

AAC CAG TGG GCC CCG CTC AAC CCC ATC CGC AAC CCC ATC GAG CGG CCG    3171
Asn Gln Trp Ala Pro Leu Asn Pro Ile Arg Asn Pro Ile Glu Arg Pro
                1040                1045                1050

GGG GGC CAC AAG GAC GTG CTC TAC CAG TGC AAG AAC TTC ACG CCG CCG    3219
Gly Gly His Lys Asp Val Leu Tyr Gln Cys Lys Asn Phe Thr Pro Pro
                1055                1060                1065

CCG CGC AGG GCG GAC GAG GCG CTG CCC GGG CCG GCG CGC CAC GCG GCC    3267
Pro Arg Arg Ala Asp Glu Ala Leu Pro Gly Pro Ala Arg His Ala Ala
                1070                1075                1080

GTC AGG GAG GAT GAG GAG GAC GAG GAT CTG GGC CGC GGT GAG GAG GAC    3315
Val Arg Glu Asp Glu Glu Asp Glu Asp Leu Gly Arg Gly Glu Glu Asp
1085                1090                1095                1100

TCC CTG GAG GCG GAG AAG TTC CTC TCA CAC AAA TTC ACC AAA GAT CCT    3363
Ser Leu Glu Ala Glu Lys Phe Leu Ser His Lys Phe Thr Lys Asp Pro
                1105                1110                1115

GGC CGC TCG CCG GGG AGG CCC GCC CAC TGG CCT CAG GCC CCA AAG TGG    3411
Gly Arg Ser Pro Gly Arg Pro Ala His Trp Pro Gln Ala Pro Lys Trp
                1120                1125                1130

ACA ACC GCG CGG TCA GGA GCA TCA ATG AGG CCC TAC GCC GGC AAG GAG T  3460
Thr Thr Ala Arg Ser Gly Ala Ser Met Arg Pro Tyr Ala Gly Lys Glu
                1135                1140                1145

AGGGGCGGCT GCCAGCTGGG CCGGGACCCA GGGCCCTCGG TGGGAGCCAT GCCGTCTGCC   3520

GGACCCGGAG GCCGAGGCCA TGTGCATAGT TTCTTTATTT TGTGTAAAAA AACCACCAAA   3580

AACAAAAACC AAATGTTTAT TTTCTACGTT TCTTTAACCT TGTATAAATT ATTCAGTAAC   3640
```

-continued

```
TGTCAGGCTG AAAACAATGG AGTATTCTCG GATAGTTGCT ATTTTTGTAA AGTTTCCGTG    3700

CGTGGCACTC GCTGTATGAA AGGAGAGAGC AAAGGGTGTC TGCGTCGTCA CCAAATCGTA    3760

GCGTTTGTTA CCAGAGGTTG TGCACTGTTT ACAGAATCTT CCTTTTATTC CTCACTCGGG    3820

TTTCTCTGTG GCTCCAGGCC AAAGTGCCGG TGAGACCCAT GGCTGTGTTG GTGTGGCCCA    3880

TGGCTGTTGG TGGGACCCGT GGCTGATGGT GTGGCCTGTG GCTGTCGGTG GGACTCGTGG    3940

CTGTCAATGG GACCTGTGGC TGTCGGTGGG ACCTACGGTG GTCGGTGGGA CCCTGGTTAT    4000

TGATGTGGCC CTGGCTGCCG GCACGGCCCG TGGCTGTTGA CGCACCTGTG GTTGTTAGTG    4060

GGGCCTGAGG TCATCGGCGT GGCCCAAGGC CGGCAGGTCA ACCTCGCGCT TGCTGGCCAG    4120

TCCACCCTGC CTGCCGTCTG TGCTTCCTCC TGCCCAGAAC GCCCGCTCCA GCGATCTCTC    4180

CACTGTGCTT TCAGAAGTGC CCTTCCTGCT GCGAAGTTCT CCCATCCTGG GACGGCGGCA    4240

GTATTGAAGC TCGTGACAAG TGCCTTCACA CAGAACCCTC GGAACTGTCC ACGCGTTCCG    4300

TGGGAACAAG GGGTT                                                     4315
```

(2) INFORMATION FOR SEQ ID NO: 4:

(i) SEQUENCE CHARACTERISTICS:
        (A) LENGTH: 1148 amino acids
        (B) TYPE: amino acid
        (D) TOPOLOGY: linear (ii) MOLECULE TYPE: protein (xi) SEQUENCE DESCRIPTION: SEQ ID NO: 4:

```
Asp Gly Asp Gly Arg Thr Thr Arg Ala Gly Gly Cys Gly His Asp Glu
  1               5                  10                  15

Cys Asp Thr Tyr Val Arg Val Cys Leu Lys Glu Tyr Gln Ala Lys Val
                 20                  25                  30

Thr Pro Thr Gly Pro Cys Ser Tyr Gly His Gly Ala Thr Pro Val Leu
             35                  40                  45

Gly Gly Asn Ser Phe Tyr Leu Pro Pro Ala Gly Ala Gly Asp Arg
     50                  55                  60

Ala Arg Ala Arg Ala Arg Ala Gly Gly Asp Gln Asp Pro Gly Leu Val
 65                  70                  75                  80

Val Ile Pro Phe Gln Phe Ala Trp Pro Arg Ser Phe Thr Leu Ile Val
                 85                  90                  95

Glu Ala Trp Asp Trp Asp Asn Asp Thr Thr Pro Asn Glu Glu Leu Leu
                100                 105                 110

Ile Glu Arg Val Ser His Ala Gly Met Ile Asn Pro Glu Asp Arg Trp
            115                 120                 125

Lys Ser Leu His Phe Ser Gly His Val Ala His Leu Glu Leu Gln Ile
130                 135                 140

Arg Val Arg Cys Asp Glu Asn Tyr Tyr Ser Ala Thr Cys Asn Lys Phe
145                 150                 155                 160

Cys Arg Pro Arg Asn Asp Phe Phe Gly His Tyr Thr Cys Asp Gln Tyr
                165                 170                 175

Gly Asn Lys Ala Cys Met Asp Gly Trp Met Gly Lys Glu Cys Lys Glu
            180                 185                 190

Ala Val Cys Lys Gln Gly Cys Asn Leu Leu His Gly Gly Cys Thr Val
        195                 200                 205

Pro Gly Glu Cys Arg Cys Ser Tyr Gly Trp Gln Gly Arg Phe Cys Asp
    210                 215                 220

Glu Cys Val Pro Tyr Pro Gly Cys Val His Gly Ser Cys Val Glu Pro
```

-continued

```
                225                 230                 235                 240
        Trp Gln Cys Asn Cys Glu Thr Asn Trp Gly Gly Leu Leu Cys Asp Lys
                        245                 250                 255
        Asp Leu Asn Tyr Cys Gly Ser His His Pro Cys Thr Asn Gly Gly Thr
                        260                 265                 270
        Cys Ile Asn Ala Glu Pro Asp Gln Tyr Arg Cys Thr Cys Pro Asp Gly
                        275                 280                 285
        Tyr Ser Gly Arg Asn Cys Glu Lys Ala Glu His Ala Cys Thr Ser Asn
                        290                 295                 300
        Pro Cys Ala Asn Gly Gly Ser Cys His Glu Val Pro Ser Gly Phe Glu
        305                 310                 315                 320
        Cys His Cys Pro Ser Gly Trp Ser Gly Pro Thr Cys Ala Leu Asp Ile
                        325                 330                 335
        Asp Glu Cys Ala Ser Asn Pro Cys Ala Ala Gly Gly Thr Cys Val Asp
                        340                 345                 350
        Gln Val Asp Gly Phe Glu Cys Ile Cys Pro Glu Gln Trp Val Gly Ala
                        355                 360                 365
        Thr Cys Gln Leu Asp Val Asn Asp Cys Arg Gly Gln Cys Gln His Gly
                        370                 375                 380
        Gly Thr Cys Lys Asp Leu Val Asn Gly Tyr Gln Cys Val Cys Pro Arg
        385                 390                 395                 400
        Gly Phe Gly Gly Arg His Cys Glu Leu Glu Arg Asp Lys Cys Ala Ser
                        405                 410                 415
        Ser Pro Cys His Ser Gly Gly Leu Cys Glu Asp Leu Ala Asp Gly Phe
                        420                 425                 430
        His Cys His Cys Pro Gln Gly Phe Ser Gly Pro Leu Cys Glu Val Asp
                        435                 440                 445
        Val Asp Leu Cys Glu Pro Ser Pro Cys Arg Asn Gly Ala Arg Cys Tyr
        450                 455                 460
        Asn Leu Glu Gly Asp Tyr Tyr Cys Ala Cys Pro Asp Asp Phe Gly Gly
        465                 470                 475                 480
        Lys Asn Cys Ser Val Pro Arg Glu Pro Cys Trp Arg Gly Leu Gln Ser
                        485                 490                 495
        Asp Arg Trp Leu Arg Val Arg Arg Gly Ala Trp Asp Ala Trp His Ser
                        500                 505                 510
        Thr Ser Gly Val Cys Gly Pro His Gly Arg Cys Val Ser Gln Pro Gly
                        515                 520                 525
        Gly Asn Phe Ser Cys Ile Cys Asp Ser Gly Phe Thr Gly Thr Tyr Cys
                        530                 535                 540
        His Glu Asn Ile Asp Asp Cys Leu Gly Gln Pro Cys Arg Asn Gly Gly
        545                 550                 555                 560
        Thr Cys Ile Asp Glu Val Asp Ala Phe Arg Cys Phe Cys Pro Ser Gly
                        565                 570                 575
        Trp Glu Gly Glu Leu Cys Asp Thr Asn Pro Asn Asp Cys Leu Pro Asp
                        580                 585                 590
        Pro Cys His Ser Arg Gly Arg Cys Tyr Asp Leu Val Asn Asp Phe Tyr
                        595                 600                 605
        Cys Ala Cys Asp Asp Gly Trp Lys Gly Lys Thr Cys His Ser Arg Glu
                        610                 615                 620
        Phe Gln Cys Asp Ala Tyr Thr Cys Ser Asn Gly Gly Thr Cys Tyr Asp
        625                 630                 635                 640
        Ser Gly Asp Thr Phe Arg Cys Ala Cys Pro Pro Gly Trp Lys Gly Ser
                        645                 650                 655
```

-continued

```
Thr Cys Ala Val Ala Lys Asn Ser Ser Cys Leu Pro Asn Pro Cys Val
            660                 665                 670

Asn Gly Gly Thr Cys Val Gly Ser Gly Ala Ser Phe Ser Cys Ile Cys
            675                 680                 685

Arg Asp Gly Trp Glu Gly Arg Thr Cys Thr His Asn Thr Asn Asp Cys
            690                 695                 700

Asn Pro Leu Pro Cys Tyr Asn Gly Gly Ile Cys Val Asp Gly Val Asn
705                 710                 715                 720

Trp Phe Arg Cys Glu Cys Ala Pro Gly Phe Ala Gly Pro Asp Cys Arg
                725                 730                 735

Ile Asn Ile Asp Glu Cys Gln Ser Ser Pro Cys Ala Tyr Gly Ala Thr
            740                 745                 750

Cys Val Asp Glu Ile Asn Gly Tyr Arg Cys Ser Cys Pro Pro Gly Arg
            755                 760                 765

Ala Gly Pro Arg Cys Gln Glu Val Ile Gly Phe Gly Arg Ser Cys Trp
            770                 775                 780

Ser Arg Gly Thr Pro Phe Pro His Gly Ser Ser Trp Val Glu Asp Cys
785                 790                 795                 800

Asn Ser Cys Arg Cys Leu Asp Gly Arg Arg Asp Cys Ser Lys Val Trp
                805                 810                 815

Cys Gly Trp Lys Pro Cys Leu Leu Ala Gly Gln Pro Glu Ala Leu Ser
                820                 825                 830

Ala Gln Cys Pro Leu Gly Gln Arg Cys Leu Glu Lys Ala Pro Gly Gln
            835                 840                 845

Cys Leu Arg Pro Pro Cys Glu Ala Trp Gly Glu Cys Gly Ala Glu Glu
            850                 855                 860

Pro Pro Ser Thr Pro Cys Leu Pro Arg Ser Gly His Leu Asp Asn Asn
865                 870                 875                 880

Cys Ala Arg Leu Thr Leu His Phe Asn Arg Asp His Val Pro Gln Gly
                885                 890                 895

Thr Thr Val Gly Ala Ile Cys Ser Gly Ile Arg Ser Leu Pro Ala Thr
            900                 905                 910

Arg Ala Val Ala Arg Asp Arg Leu Leu Val Leu Leu Cys Asp Arg Ala
            915                 920                 925

Ser Ser Gly Ala Ser Ala Val Glu Val Ala Val Ser Phe Ser Pro Ala
930                 935                 940

Arg Asp Leu Pro Asp Ser Ser Leu Ile Gln Gly Ala Ala His Ala Ile
945                 950                 955                 960

Val Ala Ala Ile Thr Gln Arg Gly Asn Ser Ser Leu Leu Leu Ala Val
                965                 970                 975

Thr Glu Val Lys Val Glu Thr Val Val Thr Gly Gly Ser Ser Thr Gly
            980                 985                 990

Leu Leu Val Pro Val Leu Cys Gly Ala Phe Ser Val Leu Trp Leu Ala
            995                 1000                1005

Cys Val Val Leu Cys Val Trp Trp Thr Arg Lys Arg Arg Lys Glu Arg
            1010                1015                1020

Glu Arg Ser Arg Leu Pro Arg Glu Glu Ser Ala Asn Asn Gln Trp Ala
1025                1030                1035                1040

Pro Leu Asn Pro Ile Arg Asn Pro Ile Glu Arg Pro Gly Gly His Lys
                1045                1050                1055

Asp Val Leu Tyr Gln Cys Lys Asn Phe Thr Pro Pro Arg Arg Ala
                1060                1065                1070
```

-continued

```
Asp Glu Ala Leu Pro Gly Pro Ala Arg His Ala Ala Val Arg Glu Asp
        1075                1080                1085

Glu Glu Asp Glu Asp Leu Gly Arg Gly Glu Glu Asp Ser Leu Glu Ala
        1090                1095                1100

Glu Lys Phe Leu Ser His Lys Phe Thr Lys Asp Pro Gly Arg Ser Pro
1105                1110                1115                1120

Gly Arg Pro Ala His Trp Pro Gln Ala Pro Lys Trp Thr Thr Ala Arg
                1125                1130                1135

Ser Gly Ala Ser Met Arg Pro Tyr Ala Gly Lys Glu
        1140                1145
```

(2) INFORMATION FOR SEQ ID NO: 5:

(i) SEQUENCE CHARACTERISTICS:
        (A) LENGTH: 1219 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Arg Ser Pro Arg Thr Arg Gly Arg Pro Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Ile Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Ile
                165                 170                 175

Ala His Phe Glu Tyr Gln Ile Arg Val Thr Cys Asp Asp His Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Glu Cys Asn Lys Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Thr Cys Asn Glu Pro Trp Gln Cys Leu Cys Glu Thr Asn Trp
```

-continued

```
                275                 280                 285
Gly Gly Gln Leu Cys Asp Lys Asp Leu Asn Tyr Cys Gly Thr His Gln
            290                 295                 300

Pro Cys Leu Asn Arg Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Ser Gly Phe Glu Cys Glu Cys Ser Pro Gly Trp Thr Gly
            355                 360                 365

Pro Thr Cys Ser Thr Asn Ile Asp Asp Cys Ser Pro Asn Asn Cys Ser
370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Arg Ser Cys Lys Asn Leu Ile Ala
            420                 425                 430

Ser Tyr Tyr Cys Asp Cys Leu Pro Gly Trp Met Gly Gln Asn Cys Asp
            435                 440                 445

Ile Asn Ile Asn Asp Cys Leu Gly Gln Cys Gln Asn Asp Ala Ser Cys
            450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
            515                 520                 525

Cys Glu Pro Asn Pro Cys Gln Asn Gly Ala Gln Cys Tyr Asn Arg Ala
530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Glu
            595                 600                 605

Ser Gly Gly Lys Phe Thr Cys Asp Cys Asn Lys Gly Phe Thr Gly Thr
610                 615                 620

Tyr Cys His Glu Asn Ile Asn Asp Cys Glu Gly Asn Pro Cys Thr Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala His Cys Glu Asn Asn Ile Asn Asp Cys Ser
            660                 665                 670

Gln Asn Pro Cys His Tyr Gly Gly Thr Cys Arg Asp Leu Val Asn Asp
            675                 680                 685

Phe Tyr Cys Asp Cys Lys Asn Gly Trp Lys Gly Lys Thr Cys His Ser
690                 695                 700
```

-continued

```
Arg Asp Ser Gln Cys Asp Glu Ala Thr Cys Asn Asn Gly Gly Thr Cys
705                 710                 715                 720

Tyr Asp Glu Val Asp Thr Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Asp Ser Phe Thr Cys
        755                 760                 765

Val Cys Lys Glu Gly Trp Glu Gly Pro Ile Cys Thr Gln Asn Thr Asn
    770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Gln Cys Ile Cys Pro Pro
        835                 840                 845

Gly His Ser Gly Ala Lys Cys His Glu Val Ser Gly Arg Ser Cys Ile
    850                 855                 860

Thr Met Gly Arg Val Ile Leu Asp Gly Ala Lys Trp Asp Asp Asp Cys
865                 870                 875                 880

Asn Thr Cys Gln Cys Leu Asn Gly Arg Val Ala Cys Ser Lys Val Trp
                885                 890                 895

Cys Gly Pro Arg Pro Cys Arg Leu His Lys Gly His Gly Glu Cys Pro
            900                 905                 910

Asn Gly Gln Ser Cys Ile Pro Val Leu Asp Asp Gln Cys Phe Val Arg
        915                 920                 925

Pro Cys Thr Gly Ala Gly Glu Cys Arg Ser Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile Ala Cys Glu Pro Ser Leu Ser Ala
        995                 1000                1005

Asn Asn Glu Ile His Val Ala Ile Ser Ala Glu Asp Ile Arg Asp Asp
    1010                1015                1020

Gly Asn Pro Val Lys Glu Ile Thr Asp Lys Ile Ile Asp Leu Val Ser
1025                1030                1035                1040

Lys Arg Asp Gly Asn Ser Ser Leu Ile Ala Ala Val Ala Glu Val Arg
                1045                1050                1055

Val Gln Arg Arg Pro Leu Lys Asn Arg Thr Asp Phe Leu Val Pro Leu
            1060                1065                1070

Leu Ser Ser Val Leu Thr Val Ala Trp Val Cys Cys Leu Val Thr Ala
        1075                1080                1085

Phe Tyr Trp Cys Val Arg Lys Arg Arg Lys Pro Ser Ser His Thr
    1090                1095                1100

His Ser Ala Pro Glu Asp Asn Thr Thr Asn Asn Val Arg Glu Gln Leu
1105                1110                1115                1120
```

-continued

```
Asn Gln Ile Lys Asn Pro Ile Glu Lys His Gly Ala Asn Thr Val Pro
                1125                1130                1135

Ile Lys Asp Tyr Glu Asn Lys Asn Ser Lys Met Ser Lys Ile Arg Thr
            1140                1145                1150

His Asn Ser Glu Val Glu Asp Asp Met Asp Lys His Gln Gln Lys
        1155                1160                1165

Val Arg Phe Ala Lys Gln Pro Val Tyr Thr Leu Val Asp Arg Glu Glu
    1170                1175                1180

Lys Val Pro Gln Arg Thr Pro Thr Lys His Pro Asn Trp Thr Asn Lys
1185                1190                1195                1200

Gln Asp Asn Arg Asp Leu Glu Ser Ala Gln Ser Leu Asn Arg Met Glu
                1205                1210                1215

Tyr Ile Val
```

(2) INFORMATION FOR SEQ ID NO: 6:

(i) SEQUENCE CHARACTERISTICS:
        (A) LENGTH: 1248 amino acids
        (B) TYPE: amino acid
        (D) TOPOLOGY: linear (ii) MOLECULE TYPE: peptide (xi) SEQUENCE DESCRIPTION: SEQ ID NO: 6:

```
Met Arg Ala Arg Gly Trp Gly Arg Leu Pro Arg Arg Leu Leu Leu Leu
1               5                   10                  15

Leu Val Leu Cys Val Gln Ala Thr Arg Pro Met Gly Tyr Phe Glu Leu
                20                  25                  30

Gln Leu Ser Ala Leu Arg Asn Val Asn Gly Glu Leu Leu Ser Gly Ala
            35                  40                  45

Cys Cys Asp Gly Asp Gly Arg Thr Thr Arg Ala Gly Gly Cys Gly Arg
50                  55                  60

Asp Glu Cys Asp Thr Tyr Val Arg Val Cys Leu Lys Glu Tyr Gln Ala
65                  70                  75                  80

Lys Val Thr Pro Thr Gly Pro Cys Ser Tyr Gly Tyr Gly Ala Thr Pro
                85                  90                  95

Val Leu Gly Ser Asn Ser Phe Tyr Leu Pro Pro Ala Gly Ala Ala Gly
                100                 105                 110

Asp Arg Ala Arg Ala Arg Ser Arg Thr Gly Gly His Gln Asp Pro Gly
            115                 120                 125

Leu Val Val Ile Pro Phe Gln Phe Ala Trp Pro Arg Ser Phe Thr Leu
130                 135                 140

Ile Val Glu Ala Trp Asp Trp Asp Asn Asp Thr Thr Pro Asp Glu Glu
145                 150                 155                 160

Leu Leu Ile Glu Arg Val Ser His Ala Gly Met Ile Asn Pro Glu Asp
                165                 170                 175

Arg Trp Lys Ser Leu His Phe Ser Gly His Val Ala His Leu Glu Leu
            180                 185                 190

Gln Ile Arg Val Arg Cys Asp Glu Asn Tyr Tyr Ser Ala Thr Cys Asn
        195                 200                 205

Lys Phe Cys Arg Pro Arg Asn Asp Phe Phe Gly His Tyr Thr Cys Asp
210                 215                 220

Gln Tyr Gly Asn Lys Ala Cys Met Asp Gly Trp Met Gly Lys Glu Cys
225                 230                 235                 240

Lys Glu Ala Val Cys Lys Gln Gly Cys Asn Leu Leu His Gly Gly Cys
                245                 250                 255
```

-continued

```
Thr Val Pro Gly Glu Cys Arg Cys Ser Tyr Gly Trp Gln Gly Lys Phe
            260                 265                 270

Cys Asp Glu Cys Val Pro Tyr Pro Gly Cys Val His Gly Ser Cys Val
        275                 280                 285

Glu Pro Trp His Cys Asp Cys Glu Thr Asn Trp Gly Leu Leu Cys
    290                 295                 300

Asp Lys Asp Leu Asn Tyr Cys Gly Ser His His Pro Cys Val Asn Gly
305                 310                 315                 320

Gly Thr Cys Ile Asn Ala Glu Pro Asp Gln Tyr Leu Cys Ala Cys Pro
                325                 330                 335

Asp Gly Tyr Leu Gly Lys Asn Cys Glu Arg Ala Glu His Ala Cys Ala
            340                 345                 350

Ser Asn Pro Cys Ala Asn Gly Ser Cys His Glu Val Leu Ser Gly
        355                 360                 365

Phe Glu Cys His Cys Pro Ser Gly Trp Ser Gly Pro Thr Cys Ala Leu
    370                 375                 380

Asp Ile Asp Glu Cys Ala Ser Asn Pro Cys Ala Ala Gly Gly Thr Cys
385                 390                 395                 400

Val Asp Gln Val Asp Gly Phe Glu Cys Ile Cys Pro Glu Gln Trp Val
                405                 410                 415

Gly Ala Thr Cys Gln Leu Asp Ala Asn Glu Cys Glu Gly Lys Pro Cys
            420                 425                 430

Leu Asn Ala Phe Ser Cys Lys Asn Leu Ile Gly Tyr Tyr Cys Asp
        435                 440                 445

Cys Leu Pro Gly Trp Lys Gly Ala Asn Cys His Ile Asn Ile Asn Asp
    450                 455                 460

Cys His Gly Gln Cys Gln His Gly Gly Thr Cys Lys Asp Leu Val Asn
465                 470                 475                 480

Gly Tyr Gln Cys Val Cys Pro Arg Gly Phe Gly Arg His Cys Glu
                485                 490                 495

Leu Glu Tyr Tyr Lys Cys Ala Ser Ser Pro Cys Arg Arg Gly Gly Ile
            500                 505                 510

Cys Glu Asp Leu Val Asp Gly Phe Arg Cys His Cys Pro Arg Gly Leu
    515                 520                 525

Ser Gly Pro Leu Cys Glu Val Asp Val Asp Leu Trp Cys Glu Pro Asn
530                 535                 540

Pro Cys Leu Asn Gly Ala Arg Cys Tyr Asn Leu Glu Asp Asp Tyr Tyr
545                 550                 555                 560

Cys Ala Cys Pro Glu Asp Phe Gly Gly Lys Asn Cys Ser Val Pro Arg
                565                 570                 575

Glu Thr Cys Pro Gly Gly Ala Cys Arg Val Ile Asp Gly Cys Gly Phe
            580                 585                 590

Glu Ala Gly Ser Arg Ala His Gly Ala Ala Pro Ser Gly Val Cys Gly
        595                 600                 605

Pro His Gly His Cys Val Ser Leu Pro Gly Gly Asn Phe Ser Cys Ile
    610                 615                 620

Cys Asp Ser Gly Phe Thr Gly Thr Tyr Cys His Glu Asn Ile Asp Asp
625                 630                 635                 640

Cys Met Gly Gln Pro Cys Arg Asn Gly Gly Thr Cys Ile Asp Glu Val
                645                 650                 655

Asp Ser Phe Ala Cys Phe Cys Pro Ser Gly Trp Glu Gly Glu Leu Cys
            660                 665                 670
```

-continued

```
Asp Ile Asn Pro Asn Asp Cys Leu Pro Asp Pro Cys His Ser Arg Gly
            675                 680                 685
Arg Cys Tyr Asp Leu Val Asn Asp Phe Tyr Cys Val Cys Asp Asp Gly
        690                 695                 700
Trp Lys Asp Lys Thr Cys His Ser Arg Glu Phe Gln Cys Asp Ala Tyr
705                 710                 715                 720
Thr Cys Ser Asn Gly Gly Thr Cys Tyr Asp Ser Gly Asp Thr Phe Arg
            725                 730                 735
Cys Ala Cys Pro Pro Gly Trp Lys Gly Ser Thr Cys Thr Ile Ala Lys
            740                 745                 750
Asn Ser Ser Cys Val Pro Asn Pro Cys Val Asn Gly Thr Cys Val
        755                 760                 765
Gly Ser Gly Asp Ser Phe Ser Cys Ile Cys Arg Asp Gly Trp Glu Gly
        770                 775                 780
Arg Thr Cys Thr His Asn Thr Asn Asp Cys Asn Pro Leu Pro Cys Tyr
785                 790                 795                 800
Asn Gly Gly Ile Cys Val Asp Gly Val Asn Trp Phe Arg Cys Glu Cys
            805                 810                 815
Ala Pro Gly Phe Ala Gly Pro Asp Cys Arg Ile Asn Ile Asp Glu Cys
            820                 825                 830
Gln Ser Ser Pro Cys Ala Tyr Gly Ala Thr Cys Val Asp Glu Ile Asn
        835                 840                 845
Gly Tyr Arg Cys Ser Cys Pro Pro Gly Arg Ser Gly Pro Arg Cys Gln
        850                 855                 860
Glu Val Val Ile Phe Thr Arg Pro Cys Trp Ser Arg Gly Val Ser Phe
865                 870                 875                 880
Pro His Gly Ser Ser Trp Val Glu Asp Cys Asn Ser Cys Arg Cys Leu
            885                 890                 895
Asp Gly His Arg Asp Cys Ser Lys Val Trp Cys Gly Trp Lys Pro Cys
            900                 905                 910
Leu Leu Ser Pro Gln Pro Ser Ala Leu Ser Ala Gln Cys Pro Pro Gly
        915                 920                 925
Gln Gln Cys Arg Glu Lys Ala Met Gly Gln Cys Leu Gln Pro Pro Cys
        930                 935                 940
Glu Asn Trp Gly Glu Cys Thr Ala Glu Asp Pro Leu Pro Pro Ser Thr
945                 950                 955                 960
Pro Cys Leu Pro Arg Thr Thr His Leu Asp Asn Asn Cys Ala Arg Leu
            965                 970                 975
Thr Leu His Phe Asn Arg Asp Gln Val Pro Gln Gly Thr Thr Val Gly
            980                 985                 990
Ala Ile Cys Ser Gly Ile Arg Ala Leu Pro Ala Thr Arg Ala Ala Ala
        995                 1000                1005
Arg Asp Arg Leu Leu Leu Leu Cys Asp Arg Ala Ser Ser Gly Ala
    1010                1015                1020
Ser Ala Val Glu Val Ala Val Ser Phe Ser Pro Ala Arg Asp Leu Pro
1025                1030                1035                1040
Asp Ser Ser Leu Ile Gln Ser Thr Ala His Ala Ile Val Ala Ala Ile
            1045                1050                1055
Thr Gln Arg Gly Asn Ser Ser Leu Leu Leu Ala Val Thr Glu Val Lys
        1060                1065                1070
Val Glu Thr Val Val Met Gly Gly Ser Ser Thr Gly Leu Leu Val Pro
        1075                1080                1085
Val Leu Cys Ser Val Phe Ser Val Leu Trp Leu Ala Cys Met Val Ile
```

-continued

```
                1090                1095                1100
Cys Val Trp Trp Thr Arg Lys Arg Lys Glu Arg Glu Arg Ser Arg
1105                1110                1115                1120

Leu Pro Arg Asp Glu Ser Ala Asn Asn Gln Trp Ala Pro Leu Asn Pro
                1125                1130                1135

Ile Arg Asn Pro Ile Glu Arg Pro Gly Ser Ser Gly Leu Gly Thr Gly
                1140                1145                1150

Gly His Lys Asp Val Leu Tyr Gln Cys Lys Asn Phe Thr Pro Pro Pro
                1155                1160                1165

Arg Arg Ala Gly Glu Ala Leu Pro Gly Pro Ala Ser His Gly Ala Gly
                1170                1175                1180

Gly Glu Asp Glu Glu Asp Glu Glu Leu Ser Arg Gly Asp Gly Arg Leu
1185                1190                1195                1200

Ser Arg Ser Arg Glu Val Pro Leu Thr Gln Ile His Gln Arg Pro Gln
                1205                1210                1215

Leu Leu Pro Gly Lys Ala Ser Leu Leu Ala Pro Gly Pro Lys Val Asp
                1220                1225                1230

Asn Arg Ala Val Arg Ser Thr Lys Asp Val Arg Cys Ala Gly Arg Glu
                1235                1240                1245
```

(2) INFORMATION FOR SEQ ID NO: 7:

(i) SEQUENCE CHARACTERISTICS:
        (A) LENGTH: 1010 amino acids
        (B) TYPE: amino acid
        (D) TOPOLOGY: linear (ii) MOLECULE TYPE: protein (xi) SEQUENCE DESCRIPTION: SEQ ID NO: 7:

```
Met Arg Ser Pro Arg Thr Arg Gly Arg Ser Gly Arg Pro Leu Ser Leu
1                   5                   10                  15

Leu Leu Ala Leu Leu Cys Ala Leu Arg Ala Lys Val Cys Gly Ala Ser
                20                  25                  30

Gly Gln Phe Glu Leu Glu Ile Leu Ser Met Gln Asn Val Asn Gly Glu
                35                  40                  45

Leu Gln Asn Gly Asn Cys Cys Gly Gly Ala Arg Asn Pro Gly Asp Arg
50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
                100                 105                 110

Arg Gly Asn Asp Arg Asn Arg Ile Val Leu Pro Phe Ser Phe Ala Trp
                115                 120                 125

Pro Arg Ser Tyr Thr Leu Leu Val Glu Ala Trp Asp Ser Ser Asn Asp
                130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
                180                 185                 190

Gly Phe Gly Cys Asn Lys Phe Cys Arg Pro Arg Asp Asp Phe Phe Gly
                195                 200                 205
```

-continued

```
His Tyr Ala Cys Asp Gln Asn Gly Asn Lys Thr Cys Met Glu Gly Trp
    210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Leu Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Lys Ser Cys Lys Asn Leu Ile Ala
            420                 425                 430

Ser Tyr Tyr Cys Asp Cys Leu Pro Gly Trp Met Gly Gln Asn Cys Asp
        435                 440                 445

Ile Asn Ile Asn Asp Cys Leu Gly Gln Cys Gln Asn Asp Ala Ser Cys
    450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525

Cys Glu Pro Asn Pro Cys Gln Asn Gly Ala Gln Cys Tyr Asn Arg Ala
    530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
        595                 600                 605

Ser Gly Gly Lys Phe Thr Cys Asp Cys Asn Lys Gly Phe Thr Gly Thr
    610                 615                 620
```

-continued

```
Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala Tyr Cys Glu Thr Asn Ile Asn Asp Cys Ser
            660                 665                 670

Gln Asn Pro Cys His Asn Gly Gly Thr Cys Arg Asp Leu Val Asn Asp
        675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Glu Ser Phe Thr Cys
        755                 760                 765

Val Cys Lys Glu Gly Trp Glu Gly Pro Ile Cys Ala Gln Asn Thr Asn
770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
            805                 810                 815

Cys Arg Ile Asn Ile Asn Glu Cys Gln Ser Ser Pro Cys Ala Phe Gly
        820                 825                 830

Ala Thr Cys Val Asp Glu Ile Asn Gly Tyr Arg Cys Val Cys Pro Pro
    835                 840                 845

Gly His Ser Gly Ala Lys Cys Gln Glu Val Ser Gly Arg Pro Cys Ile
850                 855                 860

Thr Met Gly Ser Val Ile Pro Asp Gly Ala Lys Trp Asp Asp Asp Cys
865                 870                 875                 880

Asn Thr Cys Gln Cys Leu Asn Gly Arg Ile Ala Cys Ser Lys Val Trp
            885                 890                 895

Cys Gly Pro Arg Pro Cys Leu Leu His Lys Gly His Ser Glu Cys Pro
        900                 905                 910

Ser Gly Gln Ser Cys Ile Pro Ile Leu Asp Asp Gln Cys Phe Val His
    915                 920                 925

Pro Cys Thr Gly Val Gly Glu Cys Arg Ser Ser Leu Gln Pro Val
930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
            965                 970                 975

Glu His Ile Cys Ser Glu Leu Arg Asn Leu Asn Ile Leu Lys Asn Val
        980                 985                 990

Ser Ala Glu Tyr Ser Ile Tyr Ile Ala Cys Glu Pro Ser Pro Ser Ala
    995                 1000                1005

Asn Asn
    1010
```

(2) INFORMATION FOR SEQ ID NO: 8:

(i) SEQUENCE CHARACTERISTICS:

(A) LENGTH: 63 amino acids
        (B) TYPE: amino acid
        (D) TOPOLOGY: linear (ii) MOLECULE TYPE: peptide (xi) SEQUENCE DESCRIPTION: SEQ ID NO: 8:

His Phe Glu Tyr Gln Ile Arg Val Thr Cys Asp Asp Tyr Tyr Gly
1               5                  10                  15

Phe Gly Cys Asn Lys Phe Cys Arg Pro Arg Asp Asp Phe Phe Gly His
            20                  25                  30

Tyr Ala Cys Asp Gln Asn Gly Asn Lys Thr Cys Met Glu Gly Trp Met
        35                  40                  45

Gly Pro Glu Cys Asn Arg Ala Ile Cys Arg Gln Gly Cys Ser Pro
    50                  55                  60

(2) INFORMATION FOR SEQ ID NO: 9:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO: 9:

Cys Asp Asp Tyr Tyr Tyr Gly Phe Gly Cys Asn Lys Phe Cys Arg Pro
1               5                  10                  15

Arg (2) INFORMATION FOR SEQ ID NO: 10:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO: 10:

Cys Arg Gln Gly Cys Ser Pro Lys His Gly Ser Cys Lys Leu Pro Gly
1               5                  10                  15

Asp Cys Arg Cys Gln Tyr Gly
            20

(2) INFORMATION FOR SEQ ID NO: 11:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO: 11:

Lys Arg Arg Lys Pro Gly Ser His Thr His Ser Ala Ser Glu Asp Asn
1               5                  10                  15

Thr Thr Asn (2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single (D) TOPOLOGY: linear (xi) SEQUENCE DESCRIPTION: SEQ ID NO: 12:

GAWGAWTTWT TWGGNCAWTA                                                    20

(2) INFORMATION FOR SEQ ID NO: 13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 13:

SCANGTNCCN CCSTASTGSC ANGG                                               24

(2) INFORMATION FOR SEQ ID NO: 14:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO: 14:

Gly Gly Ala Arg Asn Pro Gly Asp Arg
1               5

(2) INFORMATION FOR SEQ ID NO: 15:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO: 15:

Ala Glu Pro Gly Thr Leu Val Arg Pro Tyr
1               5                   10

(2) INFORMATION FOR SEQ ID NO: 16:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 16:

Asp Asp Phe Phe Gly His Tyr
1               5

(2) INFORMATION FOR SEQ ID NO: 17:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO: 17:

Pro Cys His Tyr Gly Gly Thr Cys Arg Asp Leu Val Asn Asp
1               5                   10

(2) INFORMATION FOR SEQ ID NO: 18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 18:

AGATCCTGTC CATGCAGAAC GT                                            22

(2) INFORMATION FOR SEQ ID NO: 19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 19:

ATACTCAAAG TGGGCAACGC C                                             21

(2) INFORMATION FOR SEQ ID NO: 20:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 20:

CCGCTCGAGA CCATGCGTTC CCCACGGA                                      28

(2) INFORMATION FOR SEQ ID NO: 21:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO: 21:

CGGAATTCTC AGTGGTGGTG GTGGTGGTGT TCATTGTTCG CTGAA                   45

(2) INFORMATION FOR SEQ ID NO: 22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 22:

CGCGGATCCT CAGCCTTGTC GGCAAATAGC                                    30

(2) INFORMATION FOR SEQ ID NO: 23:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 23:

CCCAAGCTTG CCCACTTTGA GTATCAGA                                      28

(2) INFORMATION FOR SEQ ID NO: 24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 24:

GGTCTTTTGC CACTGTTT                                      18

(2) INFORMATION FOR SEQ ID NO: 25:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 25:

GAATAGGGAG GAGAAAAC                                      18

(2) INFORMATION FOR SEQ ID NO: 26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 26:

GTCTTTTGCC ACTGTTTG                                      18

(2) INFORMATION FOR SEQ ID NO: 27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 27:

GAATAGGGAG GAGAAAAC                                      18

(2) INFORMATION FOR SEQ ID NO: 28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: intron
        (B) LOCATION: 1..10

(ix) FEATURE:
        (A) NAME/KEY: exon
        (B) LOCATION: 11..20

(xi) SEQUENCE DESCRIPTION: SEQ ID NO: 28:

GTTCGTGCAG AGGTCCTACA                                    20

(2) INFORMATION FOR SEQ ID NO: 29:

(i) SEQUENCE CHARACTERISTICS:
        (A) LENGTH: 20 base pairs
        (B) TYPE: nucleic acid
        (C) STRANDEDNESS: single (D) TOPOLOGY: linear (ix) FEATURE:
            (A) NAME/KEY: exon
            (B) LOCATION: 1..10

(ix) FEATURE:
            (A) NAME/KEY: intron
            (B) LOCATION: 11..20

(xi) SEQUENCE DESCRIPTION: SEQ ID NO: 29:

GACACCGTTC GTCAGTATCG                                                       20

(2) INFORMATION FOR SEQ ID NO: 30:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ix) FEATURE:
            (A) NAME/KEY: intron
            (B) LOCATION: 1..10

(ix) FEATURE:
            (A) NAME/KEY: exon
            (B) LOCATION: 11..20

(xi) SEQUENCE DESCRIPTION: SEQ ID NO: 30:

TTGTCTCTAG AACCTGACAG                                                       20

(2) INFORMATION FOR SEQ ID NO: 31:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ix) FEATURE:
            (A) NAME/KEY: exon
            (B) LOCATION: 1..10

(ix) FEATURE:
            (A) NAME/KEY: intron
            (B) LOCATION: 11..20

(xi) SEQUENCE DESCRIPTION: SEQ ID NO: 31:

TGTAACAGAG GTATGTGTGT                                                       20

(2) INFORMATION FOR SEQ ID NO: 32:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ix) FEATURE:
            (A) NAME/KEY: intron
            (B) LOCATION: 1..10

(ix) FEATURE:
            (A) NAME/KEY: exon
            (B) LOCATION: 11..20

(xi) SEQUENCE DESCRIPTION: SEQ ID NO: 32:

TTTTTTACAG CTATTTGCCG                                                       20

(2) INFORMATION FOR SEQ ID NO: 33:

(i) SEQUENCE CHARACTERISTICS:
           (A) LENGTH: 11 base pairs
           (B) TYPE: nucleic acid
           (C) STRANDEDNESS: single
           (D) TOPOLOGY: linear (ix) FEATURE:
           (A) NAME/KEY: exon
           (B) LOCATION: 1..10

(ix) FEATURE:
           (A) NAME/KEY: intron
           (B) LOCATION: 11

(xi) SEQUENCE DESCRIPTION: SEQ ID NO: 33:

GTGACTGCAG G                                                                11

(2) INFORMATION FOR SEQ ID NO: 34:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ix) FEATURE:
           (A) NAME/KEY: intron
           (B) LOCATION: 1..10

(ix) FEATURE:
           (A) NAME/KEY: exon
           (B) LOCATION: 11..20

(xi) SEQUENCE DESCRIPTION: SEQ ID NO: 34:

GTGTCTCCAG GTGCCAGTAT                                                       20

(2) INFORMATION FOR SEQ ID NO: 35:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ix) FEATURE:
           (A) NAME/KEY: exon
           (B) LOCATION: 1..10

(ix) FEATURE:
           (A) NAME/KEY: intron
           (B) LOCATION: 11..20

(xi) SEQUENCE DESCRIPTION: SEQ ID NO: 35:

TGTGACAAAG GTATGGCCCT                                                       20

(2) INFORMATION FOR SEQ ID NO: 36:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ix) FEATURE:
           (A) NAME/KEY: intron
           (B) LOCATION: 1..10

(ix) FEATURE:
           (A) NAME/KEY: exon
           (B) LOCATION: 11..20

(xi) SEQUENCE DESCRIPTION: SEQ ID NO: 36:

```
TTTTTGGCAG ATCTCAATTA                                              20

(2) INFORMATION FOR SEQ ID NO: 37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: exon
        (B) LOCATION: 1..10

(ix) FEATURE:
        (A) NAME/KEY: intron
        (B) LOCATION: 11..20

(xi) SEQUENCE DESCRIPTION: SEQ ID NO: 37:

TGTGAAATTG GTAAGTGGTC                                              20

(2) INFORMATION FOR SEQ ID NO: 38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: intron
        (B) LOCATION: 1..10

(ix) FEATURE:
        (A) NAME/KEY: exon
        (B) LOCATION: 11..20

(xi) SEQUENCE DESCRIPTION: SEQ ID NO: 38:

GTTTTTGCAG CTGAGCACGC                                              20

(2) INFORMATION FOR SEQ ID NO: 39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: exon
        (B) LOCATION: 1..10

(ix) FEATURE:
        (A) NAME/KEY: intron
        (B) LOCATION: 11..20

(xi) SEQUENCE DESCRIPTION: SEQ ID NO: 39:

TGCTCTACAA GTAAGTCCAA                                              20

(2) INFORMATION FOR SEQ ID NO: 40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: intron
        (B) LOCATION: 1..10
```

(ix) FEATURE:
        (A) NAME/KEY: exon
        (B) LOCATION: 11..20

(xi) SEQUENCE DESCRIPTION: SEQ ID NO: 40:

TGTTGACCAG ACATTGATGA                     20

(2) INFORMATION FOR SEQ ID NO: 41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: exon
        (B) LOCATION: 1..10

(ix) FEATURE:
        (A) NAME/KEY: intron
        (B) LOCATION: 11..20

(xi) SEQUENCE DESCRIPTION: SEQ ID NO: 41:

TGCCAGTTAG GTAAGAACAT                     20

(2) INFORMATION FOR SEQ ID NO: 42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: intron
        (B) LOCATION: 1..10

(ix) FEATURE:
        (A) NAME/KEY: exon
        (B) LOCATION: 11..20

(xi) SEQUENCE DESCRIPTION: SEQ ID NO: 42:

CTCCTTTCAG ATGCAAATGA                     20

(2) INFORMATION FOR SEQ ID NO: 43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: exon
        (B) LOCATION: 1..10

(ix) FEATURE:
        (A) NAME/KEY: intron
        (B) LOCATION: 11..20

(xi) SEQUENCE DESCRIPTION: SEQ ID NO: 43:

TGTGACATAA GTGAGTGACT                     20

(2) INFORMATION FOR SEQ ID NO: 44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: intron
        (B) LOCATION: 1..10

(ix) FEATURE:
        (A) NAME/KEY: exon
        (B) LOCATION: 11..20

(xi) SEQUENCE DESCRIPTION: SEQ ID NO: 44:

TATTTTTTAG ATATTAATGA                                                  20

(2) INFORMATION FOR SEQ ID NO: 45:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: exon
        (B) LOCATION: 1..10

(ix) FEATURE:
        (A) NAME/KEY: intron
        (B) LOCATION: 11..20

(xi) SEQUENCE DESCRIPTION: SEQ ID NO: 45:

CTCCTGTCGG GTATGTAAAT                                                  20

(2) INFORMATION FOR SEQ ID NO: 46:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: intron
        (B) LOCATION: 1..10

(ix) FEATURE:
        (A) NAME/KEY: exon
        (B) LOCATION: 11..20

(xi) SEQUENCE DESCRIPTION: SEQ ID NO: 46:

CCTCTTCTAG GATTTGGTTA                                                  20

(2) INFORMATION FOR SEQ ID NO: 47:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:

(A) NAME/KEY: exon
            (B) LOCATION: 1..10

(ix) FEATURE:
            (A) NAME/KEY: intron
            (B) LOCATION: 11..20

(xi) SEQUENCE DESCRIPTION: SEQ ID NO: 47:

CCTCTGTCAG GTGAGTGGTG                                               20

(2) INFORMATION FOR SEQ ID NO: 48:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: intron
            (B) LOCATION: 1..10

(ix) FEATURE:
            (A) NAME/KEY: exon
            (B) LOCATION: 11..20

(xi) SEQUENCE DESCRIPTION: SEQ ID NO: 48:

ATATTTGCAG CTGGACATCG                                               20

(2) INFORMATION FOR SEQ ID NO: 49:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: exon
            (B) LOCATION: 1..10

(ix) FEATURE:
            (A) NAME/KEY: intron
            (B) LOCATION: 11..20

(xi) SEQUENCE DESCRIPTION: SEQ ID NO: 49:

CCCTGTGAAG GTACCTCCCT                                               20

(2) INFORMATION FOR SEQ ID NO: 50:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: intron
            (B) LOCATION: 1..10

(ix) FEATURE:
            (A) NAME/KEY: exon
            (B) LOCATION: 11..20

(xi) SEQUENCE DESCRIPTION: SEQ ID NO: 50:

TATCTTCTAG TGATTGACAG                                               20

(2) INFORMATION FOR SEQ ID NO: 51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: exon
        (B) LOCATION: 1..10

(ix) FEATURE:
        (A) NAME/KEY: intron
        (B) LOCATION: 11..20

(xi) SEQUENCE DESCRIPTION: SEQ ID NO: 51:

TGCCATGAAA GTAAGACTCC                                        20

(2) INFORMATION FOR SEQ ID NO: 52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: intron
        (B) LOCATION: 1..10

(ix) FEATURE:
        (A) NAME/KEY: exon
        (B) LOCATION: 11..20

(xi) SEQUENCE DESCRIPTION: SEQ ID NO: 52:

TGTTTCATAG ATATTAATGA                                        20

(2) INFORMATION FOR SEQ ID NO: 53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: exon
        (B) LOCATION: 1..10

(ix) FEATURE:
        (A) NAME/KEY: intron
        (B) LOCATION: 11..20

(xi) SEQUENCE DESCRIPTION: SEQ ID NO: 53:

TGTGAAACCA AAGAGTGTGC                                        20

(2) INFORMATION FOR SEQ ID NO: 54:

(i) SEQUENCE CHARACTERISTICS:
        (A) LENGTH: 20 base pairs
        (B) TYPE: nucleic acid
        (C) STRANDEDNESS: single
        (D) TOPOLOGY: linear

```
        (ii) MOLECULE TYPE: cDNA (ix) FEATURE:
              (A) NAME/KEY: intron
              (B) LOCATION: 1..10

(ix) FEATURE:
              (A) NAME/KEY: exon
              (B) LOCATION: 11..20

(xi) SEQUENCE DESCRIPTION: SEQ ID NO: 54:

TTGATTCTAG ATATTAATGA                                                    20

(2) INFORMATION FOR SEQ ID NO: 55:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (ix) FEATURE:
              (A) NAME/KEY: exon
              (B) LOCATION: 1..10

(ix) FEATURE:
              (A) NAME/KEY: intron
              (B) LOCATION: 11..20

(xi) SEQUENCE DESCRIPTION: SEQ ID NO: 55:

GGCCACTCAC GTAAGTGGTA                                                    20

(2) INFORMATION FOR SEQ ID NO: 56:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (ix) FEATURE:
              (A) NAME/KEY: intron
              (B) LOCATION: 1..10

(ix) FEATURE:
              (A) NAME/KEY: exon
              (B) LOCATION: 11..20

(xi) SEQUENCE DESCRIPTION: SEQ ID NO: 56:

TTTCCTCCAG GTGACAGTCA                                                    20

(2) INFORMATION FOR SEQ ID NO: 57:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (ix) FEATURE:
              (A) NAME/KEY: exon
              (B) LOCATION: 1..10

(ix) FEATURE:
              (A) NAME/KEY: intron
              (B) LOCATION: 11..20
```

(xi) SEQUENCE DESCRIPTION: SEQ ID NO: 57:

TGTAACATAG GTAACTTTAT                           20

(2) INFORMATION FOR SEQ ID NO: 58:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: intron
        (B) LOCATION: 1..10

(ix) FEATURE:
        (A) NAME/KEY: exon
        (B) LOCATION: 11..20

(xi) SEQUENCE DESCRIPTION: SEQ ID NO: 58:

TCTTTTATAG CCCGAAACAG                           20

(2) INFORMATION FOR SEQ ID NO: 59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: exon
        (B) LOCATION: 1..10

(ix) FEATURE:
        (A) NAME/KEY: intron
        (B) LOCATION: 11..20

(xi) SEQUENCE DESCRIPTION: SEQ ID NO: 59:

TGTGCTCAGA GTGAGTGTCC                           20

(2) INFORMATION FOR SEQ ID NO: 60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: intron
        (B) LOCATION: 1..10

(ix) FEATURE:
        (A) NAME/KEY: exon
        (B) LOCATION: 11..20

(xi) SEQUENCE DESCRIPTION: SEQ ID NO: 60:

TTCTTTGCAG ATACCAATGA                           20

(2) INFORMATION FOR SEQ ID NO: 61:

(i) SEQUENCE CHARACTERISTICS:
        (A) LENGTH: 20 base pairs
        (B) TYPE: nucleic acid

```
            (C) STRANDEDNESS: single
            (D) TOPOLOGY: linear (ii) MOLECULE TYPE: cDNA (ix) FEATURE:
            (A) NAME/KEY: exon
            (B) LOCATION: 1..10

(ix) FEATURE:
            (A) NAME/KEY: intron
            (B) LOCATION: 11..20

(xi) SEQUENCE DESCRIPTION: SEQ ID NO: 61:

CTCATCCCTG GTAAGTGTGA                                                   20

(2) INFORMATION FOR SEQ ID NO: 62:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: intron
            (B) LOCATION: 1..10

(ix) FEATURE:
            (A) NAME/KEY: exon
            (B) LOCATION: 11..20

(xi) SEQUENCE DESCRIPTION: SEQ ID NO: 62:

GCTTTCTTAG TTACAACAGC                                                   20

(2) INFORMATION FOR SEQ ID NO: 63:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: exon
            (B) LOCATION: 1..10

(ix) FEATURE:
            (A) NAME/KEY: intron
            (B) LOCATION: 11..20

(xi) SEQUENCE DESCRIPTION: SEQ ID NO: 63:

TGCAGAATAA GTAAGGACTG                                                   20

(2) INFORMATION FOR SEQ ID NO: 64:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: intron
            (B) LOCATION: 1..10

(ix) FEATURE:
```

(A) NAME/KEY: exon
        (B) LOCATION: 11..20

(xi) SEQUENCE DESCRIPTION: SEQ ID NO: 64:

TTTCTCCTAG ACATCAATGA                                               20

(2) INFORMATION FOR SEQ ID NO: 65:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: exon
        (B) LOCATION: 1..10

(ix) FEATURE:
        (A) NAME/KEY: intron
        (B) LOCATION: 11..20

(xi) SEQUENCE DESCRIPTION: SEQ ID NO: 65:

TGCCAGGAAG GTATGTGTGC                                               20

(2) INFORMATION FOR SEQ ID NO: 66:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: intron
        (B) LOCATION: 1..10

(ix) FEATURE:
        (A) NAME/KEY: exon
        (B) LOCATION: 11..20

(xi) SEQUENCE DESCRIPTION: SEQ ID NO: 66:

CACCTGTCAG TTTCAGGGAG                                               20

(2) INFORMATION FOR SEQ ID NO: 67:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: exon
        (B) LOCATION: 1..10

(ix) FEATURE:
        (A) NAME/KEY: intron
        (B) LOCATION: 11..20

(xi) SEQUENCE DESCRIPTION: SEQ ID NO: 67:

CTGCTCAAAG GTAGGACATG                                               20

(2) INFORMATION FOR SEQ ID NO: 68:

```
     (i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: intron
         (B) LOCATION: 1..10

(ix) FEATURE:
         (A) NAME/KEY: exon
         (B) LOCATION: 11..20

(xi) SEQUENCE DESCRIPTION: SEQ ID NO: 68:

TTTTCTCCAG GTCTGGTGTG                                                   20

(2) INFORMATION FOR SEQ ID NO: 69:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: exon
         (B) LOCATION: 1..10

(ix) FEATURE:
         (A) NAME/KEY: intron
         (B) LOCATION: 11..20

(xi) SEQUENCE DESCRIPTION: SEQ ID NO: 69:

GATGTCACCA GTATGTAACA                                                   20

(2) INFORMATION FOR SEQ ID NO: 70:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: intron
         (B) LOCATION: 1..10

(ix) FEATURE:
         (A) NAME/KEY: exon
         (B) LOCATION: 11..20

(xi) SEQUENCE DESCRIPTION: SEQ ID NO: 70:

ATCGTTTTAG GGTCTTACTA                                                   20

(2) INFORMATION FOR SEQ ID NO: 71:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: exon
```

(B) LOCATION: 1..10

(ix) FEATURE:
            (A) NAME/KEY: intron
            (B) LOCATION: 11..20

(xi) SEQUENCE DESCRIPTION: SEQ ID NO: 71:

TGTGGCCATT GTAAGTATAA                                           20

(2) INFORMATION FOR SEQ ID NO: 72:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: intron
            (B) LOCATION: 1..10

(ix) FEATURE:
            (A) NAME/KEY: exon
            (B) LOCATION: 11..20

(xi) SEQUENCE DESCRIPTION: SEQ ID NO: 72:

GTTTTTCCAG TCTGCTGAAG                                           20

(2) INFORMATION FOR SEQ ID NO: 73:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: exon
            (B) LOCATION: 1..10

(ix) FEATURE:
            (A) NAME/KEY: intron
            (B) LOCATION: 11..20

(xi) SEQUENCE DESCRIPTION: SEQ ID NO: 73:

AACAGAACAG GTAGGTGTCA                                           20

(2) INFORMATION FOR SEQ ID NO: 74:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: intron
            (B) LOCATION: 1..10

(ix) FEATURE:
            (A) NAME/KEY: exon
            (B) LOCATION: 11..20

(xi) SEQUENCE DESCRIPTION: SEQ ID NO: 74:

TGCCTTACAG ATTTCCTTGT                                           20

(2) INFORMATION FOR SEQ ID NO: 75:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 75:

TAACAGGTAT GTGTGTGT                                      18

(2) INFORMATION FOR SEQ ID NO: 76:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 76:

TAACAGAGGT ATGTGTGT                                      18

(2) INFORMATION FOR SEQ ID NO: 77:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO: 77:

TGTGGCGTGG CCC                                                13

(2) INFORMATION FOR SEQ ID NO: 78:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO: 78:

TGTGGCCCTC GAC                                                13

(2) INFORMATION FOR SEQ ID NO: 79:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO: 79:

CAGTGTGATG AG                                                  12

(2) INFORMATION FOR SEQ ID NO: 80:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO: 80:

CAGTCAGTGT GA                                                  12

(2) INFORMATION FOR SEQ ID NO: 81:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 81:

AGTGCCCGAG GACT                                                       14

(2) INFORMATION FOR SEQ ID NO: 82:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 82:

AGTGCCCCGA GGAC                                                       14

(2) INFORMATION FOR SEQ ID NO: 83:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 83:

AGATCCTGTC CATGCAGAAC GT                                              22

(2) INFORMATION FOR SEQ ID NO: 84:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 84:

CATCCAGCCT TCCATGCAA                                                  19

(2) INFORMATION FOR SEQ ID NO: 85:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 85:

CTTTGAGTAT CAGATCCGCG TGA                                             23

(2) INFORMATION FOR SEQ ID NO: 86:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 86:

CGATGTCCAG CTGACAGA                                                   18

(2) INFORMATION FOR SEQ ID NO: 87:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 87:

CGGGATTTGG TTAATGGTTA T                                              21

(2) INFORMATION FOR SEQ ID NO: 88:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 88:

GGTACCAGTT GTCTCCAT                                                  18

(2) INFORMATION FOR SEQ ID NO: 89:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 89:

GGAACAACCT GTAACATAGC                                                20

(2) INFORMATION FOR SEQ ID NO: 90:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 90:

GGCCACATGT ATTTCATTGT T                                              21

(2) INFORMATION FOR SEQ ID NO: 91:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 91:

GAATATTCAA TCTACATCGC TT                                             22

(2) INFORMATION FOR SEQ ID NO: 92:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 92:

CTCAGACTCG AGTATGACAC GA                                             22

(2) INFORMATION FOR SEQ ID NO: 93:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 93:

AAAGTGCCCA GAGCTTAAAC CG                                                    22

(2) INFORMATION FOR SEQ ID NO: 94:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 94:

GGTGTTTTAA ACATCTGACG TCGTA                                                 25

(2) INFORMATION FOR SEQ ID NO: 95:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 95:

CAGGGAAGAA GGCTGCAATG T                                                     21

(2) INFORMATION FOR SEQ ID NO: 96:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 96:

TGGTGGGGTG ATAAATGGAC AC                                                    22

(2) INFORMATION FOR SEQ ID NO: 97:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 97:

GTTTTACTCT GATCCCTC                                                         18

(2) INFORMATION FOR SEQ ID NO: 98:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 98:

CAAGGGGCAG TGGTAGTAAG T                                                     21

(2) INFORMATION FOR SEQ ID NO: 99:

(i) SEQUENCE CHARACTERISTICS:

```
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 99:

GCTATCTCTG GGACCCTT                                                  18

(2) INFORMATION FOR SEQ ID NO: 100:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 100:

CCACGTGGGG CATAAAGTT                                                 19

(2) INFORMATION FOR SEQ ID NO: 101:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 101:

ATGGCTGCCG CAGTTCA                                                   17

(2) INFORMATION FOR SEQ ID NO: 102:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 102:

CAAGCAGACA TCCACCAT                                                  18

(2) INFORMATION FOR SEQ ID NO: 103:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 103:

Cys Asn Arg Ala Ile Cys Arg Gln Gly Cys Ser
1               5                   10

(2) INFORMATION FOR SEQ ID NO: 104:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 104:

Cys Asn Ser Tyr Leu Pro Thr Arg Leu Gln Ser
1               5                   10
```

(2) INFORMATION FOR SEQ ID NO: 105:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 105:

Trp Cys Gly Pro Arg Pro Cys Leu
1               5

(2) INFORMATION FOR SEQ ID NO: 106:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 106:

Trp Cys Gly Val Ala Leu Asp Leu
1               5

(2) INFORMATION FOR SEQ ID NO: 107:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 107:

Asp Ser Gln Cys Asp
1               5

(2) INFORMATION FOR SEQ ID NO: 108:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 108:

Asp Ser Val Met Arg
1               5

(2) INFORMATION FOR SEQ ID NO: 109:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 109:

Phe Cys Lys Cys Pro Glu Asp
1               5

(2) INFORMATION FOR SEQ ID NO: 110:

(i) SEQUENCE CHARACTERISTICS:
        (A) LENGTH: 7 amino acids

```
        (B) TYPE: amino acid
        (D) TOPOLOGY: linear (ii) MOLECULE TYPE: peptide (xi) SEQUENCE DESCRIPTION: SEQ ID NO: 110:

Phe Cys Lys Cys Pro Arg Thr
1               5
```